US007747391B2

(12) United States Patent
Gustafsson et al.

(10) Patent No.: US 7,747,391 B2
(45) Date of Patent: Jun. 29, 2010

(54) METHODS, SYSTEMS, AND SOFTWARE FOR IDENTIFYING FUNCTIONAL BIOMOLECULES

(75) Inventors: Claes Gustafsson, Belmont, CA (US); Sridhar Govindarajan, Redwood City, CA (US); Robin A. Emig, Redwood City, CA (US); Richard John Fox, Redwood City, CA (US); Ajoy K. Roy, Redwood City, CA (US); Jeremy S. Minshull, Los Altos, CA (US); S. Christopher Davis, San Francisco, CA (US); Anthony R. Cox, Mountain View, CA (US); Phillip A. Patten, Portola Valley, CA (US); Linda A. Castle, Mountain View, CA (US); Daniel L. Siehl, Menlo Park, CA (US); Rebecca Lynne Gorton, Irvine, CA (US); Teddy Chen, Belmont, CA (US)

(73) Assignee: Maxygen, Inc., Redwood City, CA (US)

( * ) Notice: Subject to any disclaimer, the term of this patent is extended or adjusted under 35 U.S.C. 154(b) by 345 days.

(21) Appl. No.: 10/629,351

(22) Filed: Jul. 29, 2003

(65) Prior Publication Data
US 2004/0161796 A1 Aug. 19, 2004

Related U.S. Application Data

(63) Continuation-in-part of application No. 10/379,378, filed on Mar. 3, 2003, and a continuation-in-part of application No. PCT/US03/06551, filed on Mar. 3, 2003.

(60) Provisional application No. 60/360,982, filed on Mar. 1, 2002.

(51) Int. Cl.
G01N 33/48 (2006.01)
G06F 19/00 (2006.01)
(52) U.S. Cl. .......................................... 702/19; 702/20
(58) Field of Classification Search ....................... None
See application file for complete search history.

(56) References Cited

U.S. PATENT DOCUMENTS

| 6,537,776 | B1 | 3/2003 | Short | 435/69.1 |
|---|---|---|---|---|
| 6,605,449 | B1 | 8/2003 | Short | 435/69.1 |
| 7,315,786 | B2 | 1/2008 | Dahiyat et al. | |
| 2001/0051855 | A1* | 12/2001 | Wang et al. | 702/19 |
| 2002/0045175 | A1 | 4/2002 | Wang et al. | |
| 2002/0048772 | A1 | 4/2002 | Dahiyat et al. | |
| 2002/0155460 | A1* | 10/2002 | Schellenberger et al. | 435/6 |
| 2003/0032059 | A1 | 2/2003 | Wang et al. | |
| 2004/0072245 | A1 | 4/2004 | Gustafsson et al. | |
| 2004/0161796 | A1 | 8/2004 | Gustafsson et al. | |
| 2005/0084907 | A1 | 4/2005 | Fox | |
| 2006/0205003 | A1 | 9/2006 | Gustafsson et al. | |
| 2007/0239364 | A1 | 10/2007 | Fox | |
| 2008/0132416 | A1 | 6/2008 | Fox | |
| 2008/0133143 | A1 | 6/2008 | Gustafsson et al. | |
| 2008/0147369 | A1 | 6/2008 | Fox | |
| 2008/0220990 | A1 | 9/2008 | Fox | |

FOREIGN PATENT DOCUMENTS

| WO | WO01/59066 | 8/2001 |
|---|---|---|
| WO | WO01/61344 | 8/2001 |
| WO | WO03/055978 | 7/2003 |
| WO | WO03/075129 | 8/2003 |
| WO | WO2006/002267 | 1/2006 |

OTHER PUBLICATIONS

Moore et al., "Computational Challenges in Combinatorial Library Design in Protein Engineering," AIChE Journal, vol. 50, No. 2, Feb. 2004, pp. 262-272.
Hu et al., "Developing Optimal Non-Linear Scoring Function for Protein Design," Bioinformatics, vol. 20, Issue 17, 2004, pp. 3080-3098.
Richard Fox, "Directed Molecular Evolution by Machine Learning and the Influence of Nonlinear Interactions," Journal of Theoretical Biology 234, 2005, pp. 187-199.
Zhang et al., "Genome Shuffling Leads to Rapid Phenotypic Improvement in Bacteria," Nature, vol. 415, Feb. 2002, pp. 644-646.
PCT Search Report for Int'l Application No. PCT/US2005/022119, dated Nov. 24, 2005.
PCT Written Opinion for Int'l Application No. PCT/US2005/022119, dated Nov. 24, 2005.
Voigt et al., "Rational Evolutionary Design: The Theory of In Vitro Protein Evolution," Advances in Protein Chemistry, Academic Press, vol. 55, pp. 79-160, 2001.
Dahiyat et al., "De Novo Protein Design: Fully Automated Sequence Selection," Science, American Assoc fro the Advancement of Science, vol. 278, No. 5335, p. 82-87, 1997.
Fox et al., "Optimizing the Search Algorithm for Protein Engineering by Directed Evolution," Protein Engineering, Oxford Univ Press, vol. 16, No. 8, pp. 589-597, 2003.
Supplemental Partial EPO Search Report for Int'l Application No. PCT/US03/06551, dated Nov. 28, 2005, 6 pages.
International Search Report for Int'l Application No. PCT/US03/06551, Completed Sep. 5, 2003, 4 pages.

(Continued)

Primary Examiner—John S Brusca
Assistant Examiner—Anna Skibinsky
(74) Attorney, Agent, or Firm—Weaver Austin Villeneuve & Sampson LLP; Norman J. Kruse

(57) ABSTRACT

The present invention generally relates to methods of rapidly and efficiently searching biologically-related data space. More specifically, the invention includes methods of identifying bio-molecules with desired properties, or which are most suitable for acquiring such properties, from complex bio-molecule libraries or sets of such libraries. The invention also provides methods of modeling sequence-activity relationships. As many of the methods are computer-implemented, the invention additionally provides digital systems and software for performing these methods.

21 Claims, 17 Drawing Sheets

OTHER PUBLICATIONS

Ness et al., "Synthetic Shuffling Expands Functional Protein Diversity by Allowing Amino Acids to Recombine Independently," Nature Biotechnology, vol. 20, 1251-1255 (2002).

Kolkman et al., "Directed Evolution of Proteins by Exon Shuffling," Nature Biotechnology, vol. 19, 423-428 (2001).

Voigt et al., "Computationally Focusing the Directed Evolution of Proteins," Journal of Cellular Biochemistry Supplement 37:58-63 (2001).

Goodacre et al., "Detection of the Dipicolinic Acid Biomarker in *Bacillus* Spores Using Curie-Point Pyrolysis Mass Spectrometry and Fourier Transform Infrared Spectroscopy," *Anal. Chem.* (2000), 72, 119-127.

Geladi et al., "Partial Least-Squares Regression: A Tutorial," *Analytica Chimica Acta*, 185 (1986) 1-17.

The GMAX: printed from website http://www.abergc.com, prior to Jul. 21, 2003, 3 pages.

Steve R. Gunn, "Support Vector Machines for Classification and Regression," Technical Report, Department of Electronics and Computer Science, University of Southampton, 1998, 57 Pages.

U.S. Office Action mailed Mar. 13, 2006, from U.S. Appl. No. 10/379,378.

U.S. Office Action mailed Jan. 27, 2006, from U.S. Appl. No. 10/386,903.

Skibinsky, "Office Action for U.S. Appl. No. 10/379,378" mailed Sep. 28, 2006.

Eroshkin et al., "PROANAL version 2: Multifunctional Program for Analysis of Multiple Protein Sequence Alignments and for Studying the Structure-Activity Relationships in Protein Families," Comput. Appl. Biosci., vol. 11, No. 1, pp. 39-44, 1995.

Eroshkin et al., "Algortihm and Computer Program Pro_Anal for Analysis of Relationship Between Structure and Activity in a Family of Proteins or Peptides," Comput. Appl. Biosci., vol. 9, No. 5, pp. 491-497, 1993.

Ivanisenko,V.A. and Eroshkin,A.M, "Search for Sites With Functionally Important Substitutions in Sets of Related or Mutant Protein," Mol. Biol. (Moskow), 31, pp. 749-755, 1997.

Berglund et al. (1997) "INLR, Implicit Non-Linear Latent Variable Regression," *Journal of Chemometrics*, 11:141-156.

Cho et al., (1998) "Rational Combinatorial Library Design. 2. Rational Design of Targeted Combinatorial Peptide Libraries Using Chemical Similarity Probe and the Inverse QSAR Approachcs," *J. Chem. Inf. Comput. Sci.* 38(2):259-268.

Dahiyat et al., (1996) "Protein Design Automation," *Protein Science* 5:895-903.

Ginalski et al., (2005)"Practical Lessons From Protein Structure Prediction," *Nucleic Acids Research*, 33( 6):1874-1891.

Gribskov, et al. (Jul. 1987) "Profile analysis: Detection of distantly related proteins" *Proc. Natl. Acad. Sci. USA, Biochemistry* 84:4355-4358.

Hellberg et al., (1987) "Peptide Quantitative Structure-Activity Relationships, a Multivariate Approach," Research Group for Chemometrics, Umca University, S-901 87 Umca, Sweden. Received Mar. 3, 1986, *Journal of Medicinal Chemistry*, 30(7):1126-1135.

Krogh, Anders (1998) "An Introduction to Hidden Markov Models for Biological Sequences," *Computational Methods in Molecular Biology*, edited by S.L. Salzberg, D.B. Searls and S. Kasif, pp. 45-63.

International Preliminary Report on Patentability dated Jun. 25, 2007 issued in PCT/US03/06551.

US Office Action dated Apr. 18, 2007 issued in U.S. Appl. No. 10/379,378.

US Office Action dated Feb. 21, 2008 issued in U.S. Appl. No. 10/379,378..

US Final Office Action dated Sep. 17, 2008 issued in U.S. Appl. No. 10/379,378.

US Final Office Action (Supplementary) dated Oct. 15, 2008 issued in U.S. Appl. No. 10/379,378.

US Office Action (Advisory Action) dated Mar. 2, 2009 issued in U.S. Appl. No. 10/379,378.

US Office Action dated Mar. 13, 2007 issued in U.S. Appl. No. 10/874,802.

Hellberg et al., "The Prediction of Bradykinin Potentiating Potency of Pentapeptides. An Example of a Peptide Quantitative Structure-Activity Relationship," Acia Chemica Scandinaviea B 40, pp. 135-140, 1988.

Bucht et al., "Optimising the Signal Peptide for Glycosyl Phosphatidylinositol Modification of Human Acetylcholinesterase Using Mutational Analysis and Peptide-Quantitative Structure-Activity Relationships," Biochimica et Biophysica Acta 1431, pp. 471-482, 1999.

Sandberg et al., "Engineering Multiple Properties of a Protein by Combinatorial Mutagenesis," Proc. Natl. Acad. Sci. USA, vol. 90, pp. 8367-8371, Sep. 1993.

Wrede et al., "Peptide Design Aided by Neural Networks: Biological Activity of Artificial Signal Peptidase I Cleavage Sites," Biochemistry, 37, pp. 3588-3593, 1998.

Jill Damborsky, "Quantitative Structure-Function and Structure-Stability Relationships of Purposely Modified Proteins," Protein Engineering, vol. 11, No. 1, pp. 21-30, 1998.

Hellberg, et al., "Peptide Quantitative Structure—Activity Relationships, a Multivariate Approach," J. Med Chem, 30: pp. 1126-1195, 1987.

Sandberg et al., "New Chemical Descriptors Relevant for the Design of Biologically Active Peptides. A Multivariate Characterization of 87 Amino Acids," J. Med Chem., 41, pp. 2481-2491, 1998.

Casari et al., "A Method to Predict Functional Residues in Proteins," Nat. Struct Biol., 2, pp. 171-178, 1995.

Suzuki et al., "A Method for Detecting Positive Selection at Single Amino Acid Sites," Mol. Biol. Evol. 16 (10): pp. 1315-1328, 1999.

Benner et al., "Amino Acid Substitution During Functionally Constrained Divergent Evolution of Protein Sequences," Protein Engineering, vol. 7, No. 11, pp. 1323-1332, 1994.

Wu et al., "Discovering Empirically Conserved Amino Acid Substitution Groups in Databases of Protein Families," Proc. Int. Conf. Intell. Syst. Mol. Biol., 4, pp. 230-240, 1996.

Adenot et al., "Peptides Quantitative Structure-Function Relationships: An Automated Mutation Strategy to Design Peptides and Pseudopeptides from Substitution Matrices," Journal of Molecular Graphics and Modelling, 17, pp. 292-309, 1999.

Norinder et al., "A Quantitative Structure-Activity Relationship Study of Some Substance P-Related Peptides," J. Peptide Res., 49, pp. 155-162, 1997.

Sandberg, "Deciphering Sequence Data a Multivariate Approach," Ph.D Thesis, Umea: Umea University, 78 pages, 1997.

Eriksson et al., "Peptide QSAR on Substance P Analogues, Enkephalins and Bradykinins Containing L-and D-Amino Acids," Acta Chemica Scandinavica, 44, pp. 50-56, 1990.

Ufkes eta l., "Further Studies on the Structure-Activity Relationships of Bradykinin-Potentiating Peptides," European Journal of Pharmacology, 79, pp. 155-158, 1982.

Dobrynin et al., "Synthesis of Model Promoter for Gene Expression in *Escherichia coli*," Symposium Series No. 7, pp. 365-376, 1980.

Skinner et al., "Potential Use of Additivity of Mutational Effects in Simplifying Protein Engineering," Proc. Natl. Acad. Sci., vol. 93, pp. 10753-10757, 1996.

Lathrop et al., "Global Optimum Protein Threading with Gapped Alignment and Empirical Pair Score Functions," J. Mol. Biol., 255, pp. 641-665, 1996.

Hellberg et al., "A Multivariate Approach to QSAR," Ph.D. Thesis, Umea, Sweden: University of Umea: 1986.

Nambier et al., "Total Synthesis and Cloning of a Gene Coding for the Ribonuclease S Protein," Science, 223: 1299-1301, 1984.

Lin et al., "Functional Expression of Horseradish Peroxidase in *E. coli* by Directed Evolution," Biotechnol. Prog, 15: 467-471, 1999.

Lathrop R.H., "The Protein Threading Problems with Sequence Amino Acids Interaction Preference is NP-Complete," Protein Eng., 7:1059-1068, 1994.

Hanes et al., "In Vitro Selection and Evolution of Functional Proteins by Using Ribosomes Display," Proc. Natl. Acad. Sci. USA, 94: 4937-4942, 1997.

Wells et al., "Rapid Evolution of Peptide and Protein Binding Properties in vitro," Curr Opin Biotechnol, 3:355-362, 1992.

Johnson et al., "The Traveling Salesman Problem: A Case Study in Local Optimization," In Local Search in Combinatorial Optimization, Edited by Aarts et al., John Wiley & Sons Ltd., 21-310, 1997.

Jonsson et al., "Quantitative Sequence-Activity Models (QSAM)—Tools for Sequence Design," Nucleic Acids Res., 21:733-739, 1993.

Geladi et al., "Partial Least Squares Regression: A Tutorial," Anal Chim Acta, 168: 1-17, 1986.

Holowachuk et al., "Efficient Gene Synthesis by Klenow Assembly/Extension-Pfu Polymerase Amplification (KAPPA) of Overlapping Olingonucleotides," PCR Methods Appl, 4:299-302, 1995.

Hellberg et al., "Minimum Analogue Peptide Sets (MAPS) for Quantitative Structure-Activity Relationships," Int J Pept Protein Res, 37:414-424, 1991.

Mee et al., "Design of Active Analogues of a 15-Residue Peptide Using D-Optimal Design, QSAR and a Combinatorial Search Algorithm," J Pept Res, 49:89-102, 1997.

Schneider et al., "Peptide Design by Artificial Neural Networks and Compouter-Based Evolutionary Search," Proc Natl Acad Sci USA, 95:12179-12184, 1998.

Sjostrom et al.,"Signal Peptide Amino Acid Sequences in *Escharichla coli* Contain Information Related to Final Protein Localization, A Multivariate Data Analysis," EMBO, 6:823-891, 1987.

Patel et al., "Patenting Computer-Designed Peptides," Journal of Computer-Aided Molecular Design, 12:543-556, 1998.

Aita et al., "Theory of Evolutionary Molecular Engineering Through Simultaneous Accumulation of Advantageous Mutations," J. Theor. Biol., 207:543-556, 2000.

Darius et al., "Simulated Molecular Evolution of Computer Generated Artifacts?," Biophysical Journal, 67:2120-2122, 1994.

Singh et al., "Application of Genetic Algorithms to Combinatorial Synthesis: A Computational Approach to Lead Identification and Lead Optimization," J.Am. Chem. Soc., 118:1669-1676, 1996.

Aita et al., "Analysis of Local Fitness Landscape with a Model of the Rough Mt. Fuji-Type Landscape: Application to Prolyl Endopeptidase and Thermolysin," Biopolymers. vol. 54, pp. 64-79, Accepted Jan. 14, 2000.

Gogos et al., "Assignment of Enzyme Substrate Specificity by Principal Component Analysis of Aligned Protein Sequences: An Experimental Test Using DNA Glycosylase Homologs," Proteins: Structure, Function, and Genetics, 40, pp. 98-105, 2000.

Vector NTI Suite 7.0 User's Manual (portion) describing software believed to be available prior to Feb. 1, 2000.

Tobin et al., "Directed Evolution: The 'Rational' Bases for 'Irrational' Design," Curr. Opin Struct Biol., 10:421-427, 2000.

van Regenmortel, M.H., "Are There Two Distinct Research Strategies for Developing Biologically Active Molecules: Rational Design and Empirical Selection?", J. Mol. Recognit, 13:1-4, 2000.

Ryu DD et all, "Recent Progress in Biomolecular Engineering," Biotechnol Prog., 16:2-16, 2000.

Gustafsson et al., "Exploration of Sequence Space for Protein Engineering," J. Mol. Recognit, 14:308-314, 2001.

Glieder et al., "Laboratory Evolution of a Soluble, Self-Sufficient, Highly Active Alkaline Hydroxylase," Nat Biotechnol, 20:1135-1139, 2002.

Lehman et al., "Exchanging the Active Site Between Phytases for Altering the Functional Properties of the Enzyme," Protein Sci, 9:1866-1872, 2000.

Kwasigroch et all, "PoPMuSiC, Rationally Designing Point Mutations in Protein Structures," Bioinformatics, 16:1701-1702, 2002.

Tangri et al., "Rationally Engineered Proteins or Antibodies with Absent or Reduced Immunogenicity," Curr Med Chem, 9:2191-2199, 2002.

Pierce et al., "Protein Design is NP-Hard," Protein Eng, 15:779-782, 2002.

Ness et al., "Molecular Breeding: The Natural Approach to Protein Design," Adv Protein Chem, 55:261-292, 2000.

Lehmann et al., "The Consensus Concept for Thermostability Engineering of Proteins: Further Proof of Concept," Protein Eng., 15:403-411, 2002.

Dimmic et al., "rtREV: An Amino Acid Substitution Matrix for Inference of Retrovirus and Reverse Transcriptase Phylogeny," J. Mol Evol, 55:65-73, 2002.

Aita et al., "A Cross-Section of the Fitness Landscape of Dihydrofolate Reductase," Protein Eng, 14:633-638, 2001.

Strom et al., "Important Structural Features of 15-Residue Lactoferricin Derivatives and Methods for Improvement of Antimicrobial Activity," Biochem Cell Biol, 80:65-74, 2002.

Choulier et al., "QSAR Studies Applied to the Prediction of Antigen-Antibody Interaction Kinetics as Measured by BIACORE," Protein Eng, 15(5):378-382, (2002).

Hoover et al., "DNA Works: an Automated Method for Designing Oligonucleotides for PCR-Based Gene Synthesis," Nucleic Acids Res, 30:E43, 2002.

Abecassis et all, "High Efficiency Family Shuffling Based on Multi-Step PCR and In vivo DNA Recombination in Yeast: Statistical and Functional Analysis of a Combinatorial Library Between Human Cytochrome P460 1A1 and 1A2," Nucleic Acids Res., 28:E88, 2000.

Aita et al., "Surveying a Local Fitness Landscape of a Protein with Epistatic Altee for the Study of Directed Evolution," Biopolymers, 64:95-106, 2002.

Prusis et al., "Proteo-chemometrics Analysis of MSH Peptide Binding to Melancortin Receptors," Protein Eng, 15:305-311, 2002.

Prusis et al., "PLS Modeling of Chimeric MS04/MSH-Peptide and MC1/MC3-Receptor Interaction Reveals a Novel Method for the Analysis of Ligand-Receptor Interactions," Biochim Biophys Acta, 1544(1-2):350-357, 2001.

Lu et al., "Predicting the Reactivity of Proteins from Their Sequence Alone: Kazal Family of Protein Inhibitors of Serine Proteinases," Proc Natl Acad Sci USA, 98(4):1410-1415, 2001.

Schein et al., "Chloroplast Transit Peptide Prediction: A Peek Inside the Black Box," Nucleic Acids Res, 29:E82, 2001.

Fariselli et al., "Prediction of Protein-Protein Interaction Sites in Heterocomplexes with Neural Networks," Eur J Biochem, 269:1356-1361, 2002.

Fariselli et al., "Prediction of Contact Maps with Neural Networks and Correlated Mutations," Protein Eng, 14(11): 835-843, 2001.

Marvanova et al., "Biochemical Characterization of Broad-Specificity Enzymes Using Multivariate Experimental Design and a Colorimetric Microplate Assay: Characterization of the Haloalkane Dehalogenase Mutants," J. Microbiol Methods, 44:14-157, 2001.

Looger et al., Computational Design of Receptor and Sensor Proteins with Novel Functions, Nature, 423:185-190, 2003.

Govindarajan et al., "Systematic Variation of Amino Acid Substitutions for Stringent Assessment of Pairwise Covariation," J. Mol. Biol, 328:1061-1069, 2003.

del Sol Mesa et al., "Automatic Methods for Predicting Functionality Important Residues," J Mol Biol, 326:1289-1302, 2003.

Benos et al., "Additivity in Protein-DNA Interactions: How Good an Approximation is it?" Nucleic Acids Res 30(20): 4442-51, 2002.

Bogarad et al., "A Hierarchical Approach to Protein Molecular Evolution," Proc Natl Acad Sci USA, 96:2591-2595, 0666, (1999).

Carlsen et al., "QSAR's Based on Partial Order Ranking," SAR QSAR Environ Res, 13(1): 153-165, 2002.

Crameri et al., "DNA Shuffling of a Family of Genes from Diverse Species Accelerates Directed Evolution," Nature, 391:288-291, 1998.

Dill K.A., "Additivity Principles in Biochemistry," J Biol Chem, 272(2): 701-704, 1997.

Distefano et al., "Quantifying Beta-Sheet Stability by Phage Display," J Mol Biol, 322(1):179-188, 2002.

Hayes et al., "Combining Computational and Experimental Screening for Rapid Optimization of Protein Properties," Proc Natl Acad Sci USA, 99(25):15926-15931, 2002.

Kell, D.B., "Metabolomics and Machine Learning: Explanatory Analysis of Complex Metabolome Data Using Genetic Programming to Produce Simple, Robust Rules," Mol Biol Rep, 29(1-2): 237-241, 2002.

Koshi et al., "Context-Dependent Optimal Substitution Matrices," Protein Eng, 8:641-645, 1995.

Koshi et al., "Mutation Matrices and Physical-Chemical Properties: Correlations and Implications," Proteins 27(3):336-344, 1997.

Lahr et al., "Patterned Library Analysis: A Method for the Quantitative Assessement of Hypotheses Concerning the Determinants of Protein Structure," Proc Natl Acad Sci USA, 96(26):14860-14865, 1999.

Lapinsh et al., "Classification of G-Protein Coupled Receptors by Alignment Independent Extraction of Principal Chemical Properties of Primary Amino Acid Sequences," Protein Sci 11(4):795-805, (2002).

Lapinsh et al., "Development of Proteo-Chemometrics: A Novel Technology for the Analysis of Drug-Receptor Interactions," Biochim Biophys Acata, 1525(1-2): 180-190, (2002).

Lapinsh et al., "Protechemometrics Modeling of the Interaction of Amine G-Protein Coupled Receptors with a Diverse Set of Ligands," Mol Pharmacol 61(6): 1465-1475, 2002.

Lapinsh et al., "QSAR and Proteo-Chemometric Analysis of the Interaction of a Series of Organic Compounds with Melanocortin Receptor Subtypes," J Med Chem, 46(13): 2572-2579, 2003.

Lee et al., "Mathematical Modelling of Inset Neuropeptide Potencies. Are Quantitatively Predictive Models Possible," Insect Biochem Mol Biol, 30(10): 899-907, 2000.

Lehman et al., "Engineering Proteins Thermostability: the Use of sequence Alignments Versus Rational Design and Directed Evolution," Current Opinion in Biotechnology 12:371-375, 2001.

Linusson et al., Statistical Molecular Design of Building Blocks for Combinatorial Chemistry, J Med Chem, 43(7): 1320-1328, 2000.

Matsuura et al., "Nonaddivity of Mutational Effects on the Properties of Catalasa I and its Application to Efficient Directed Evolution," Protein Eng, 11(9): 789-795, 1998.

Nakai et al., "Structure Modification and Functionality of Why Proteins: Quantitative Structure-Activity Relationship Approach," J Dairy Sci, 68(10):2763-2772, 1985.

Nakai et al., "Recent Advances in Structure and Function of Food Proteins: QSAR Approach," Crit Rev Food Sci Nutr, 33(6):477-499, (1993).

Ness et al., "Synthetic Shuffling Expands Functional Protein Diversity by Allowing Amino Acids to Recombine Independently," Nat Biotechnol, 20(12):1251-1255, 2002.

Niggemann et al., "Exploring Local and Non-Local Interactions for Protein Stability by Structural Motif Engineering," J Mol Biol, 296(1):181-195, 2000.

Nikolova et al., "Semirational Design of Active Tumor Suppressor p53 DNA Binding Domain with Enhanced Stability," Proc Natl Acad Sci USA, 95(25): 14675-14680, 1998.

Reymond et al., "Substrate Arrays as Enzyme Fingerprinting Tools," Chembiochem, 3(8):701-708, 2002.

Sadowski et al., "Automated Generation and Refinement of Protein Signatures: Case Study with G-Protein Coupled Receptors," Bioinformatics, 19(6(: 727-734, 2003.

Shaw et al., "Predicting Amino Acid Residues Responsible for Enzyme Specificity Solely from Protein Sequences," Biotechnol Bioeng, 79(3): 295-300, 2002.

Sheridan et al., "Designing Targeted Libraries with Genetic Algorithms," J Mol Graph Model, 18(4-5): 320-345, 525, 2000.

Siebert, K.J., "Quantitative Structure-Activity Relationship Modeling of Peptide and Protein Behavior as a Function of Amino Acid Composition," J Agric Food Chem, 49(2): 851-858, 2001.

Siebert, K.J., "Modeling Protein Function Properties from Amino Acid Composition," J Agric Food Chem, 51(26): 7792-7797, 2003.

Soyer et al., "Using Evolutionary Methods to Study G-Protein Coupled Receptors," Pac Symp Biocomput: 625-636, 2002.

Steipe, B., "Evolutionary Approaches to Protein Engineering," Curr Top Microbiol Immunol, 243: 55-86, 1999.

Umeno et al., "Evolution of the C30 Carotenoid Synthase CrtM for Function in a C40 Pathway," J Bacteriold 184(23): 6690-6699, 2002.

Veraverbeke et al., "Wheat Protein Composition and Properties of Wheat Glutenin in Relation to Breadmaking Functionality," Crit Rev Food Sci Nutr, 42(3): 179-208, 2002.

Wahler et al., "Enzyme Fingerprints by Fluorogenic and Chromogenic Substrate Arrays," Angew Chem Int Ed Engl,, 40(23): 4457-4460, 2001.

Wahler et al., "Enzyme Fingerprints of Activity, and Stereo and Enantioselectivity from Fluorogenic and Chromogenic Substrate Arrays," Chemistry, 8(14): 3211-3228, 2002.

Wang et al., "Designing Gene Libraries from Protein Profiles for Combinatorial Protein Experiments," Nucleic Acids Res, 30(21): e120, 2002.

Wells, J.A., "Additivity of Mutational Effects in Proteins," Biochemistry, 29(37): 8509-8517, 1990.

Wikberg et al., "Melanocortin Receptors: Ligands and Protechemometrics Modeling," Ann NY Acad Sci, 994:21-26, 2003.

Martin et al., "Measuring Diversity: Experimental Design of Combinatorial Libraries for Drug Discovery," J. Med. Chem. 38, 1431-1436, 1995.

Sheridan et al., "Using a Genetic Algorithm to Suggest Combinatorial Libraries," J. Chem. Inf. Compu. Sci., 35, 310-320, 1995.

D.K. Agrafiotis, "Multiobjective Optimization of Combinatorial Libraries," IBM J. Res & Dev., vol. 45, No. 3, 545-566, 2001.

US Office Action dated Jun. 12, 2009 issued in U.S. Appl. No. 10/379,378.

US Office Action dated May 27, 2009 issued in U.S. Appl. No. 11/981,577.

US Office Action dated Jun. 10, 2009 issued in U.S. Appl. No. 11/706,034.

US Office Action dated May 29, 2009 issued in 11/981,567.

European Search Report (Supplemental) dated Feb. 13, 2006 issued in EP 03 743 748.0-2201.

European Examination Report dated Jul. 31, 2008 issued in EP 03 743 748.0-2405.

European Communication dated Jan. 13, 2010 issued in EP 03 743 748.0-2405.

JP Office Action dated Feb. 26, 2009 issued in JP 2003-573522.

PCT International Preliminary Report on Patentability and Written Opinion dated Dec. 28, 2006 issued in PCT/US2005/022119.

European Examination Report dated Dec. 23, 2008 issued in EP 05 779 687.2-2405.

Atchley et al., (2000) "Correlations Among Amino Acid Sites in bHLH Protein Domains: An Information Theoretic Analysis", *Mol. Biol. Evol.* 17(1):164-178.

Perelson et al., (1995) "Protein evolution on partially correlated landscapes", *PNAS USA* 92:9657-9661.

Japanese Final Office Action mailed Feb. 24, 2010 issued in 2003-573522.

* cited by examiner

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

His Gly Pro Val Phe Ser Thr Gly Gly Ala
 1               5                   10

METHODS, SYSTEMS, AND SOFTWARE FOR IDENTIFYING FUNCTIONAL BIOMOLECULES

CROSS-REFERENCE TO RELATED APPLICATIONS

This application is a continuation in part of U.S. patent application Ser. No. 10/379,378, filed Mar. 3, 2003, naming Gustafsson et al. as inventors, and titled "Methods, Systems, and Software for Identifying Functional Bio-Molecules," and it is also a continuation in part of International Application No. PCT/US03/06551 filed Mar. 3, 2003, naming Gustafsson et al. as inventors, both of which in turn claim the benefit under 35 U.S.C. §119(e) of U.S. Ser. No. 60/360,982, filed Mar. 1, 2002. Each of these documents are incorporated herein by reference in their entireties.

COPYRIGHT NOTIFICATION

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to the fields of molecular biology, molecular evolution, bioinformatics, and digital systems. More specifically, the invention relates to methods of identifying biomolecule targets with desired properties and methods for computationally predicting the activity of a biomolecule. Systems, including digital systems, and system software for performing these methods are also provided. Methods of the present invention have utility in the optimization of proteins for industrial and therapeutic use.

BACKGROUND

Protein design has long been known to be a difficult task if for no other reason than the combinatorial explosion of possible molecules that constitute searchable sequence space. The protein design problem was recently shown to belong to a class of problems known as NP-hard (Pierce, et al. (2002) "Protein Design is NP-hard," *Prot. Eng.* 15(10):779-782), indicating that there is no algorithm known that can solve such problems in polynomial time. Because of this complexity, many approximate methods have been used to design better proteins; chief among them is the method of directed evolution. Directed evolution of proteins is today dominated by various high throughput screening and recombination formats, often performed iteratively.

Sequence space can be described as a space where all possible protein neighbors can be obtained by a series of single point mutations. Smith (1970) "Natural selection and the concept of a protein space," *Nature,* 225(232):563-4. For example, a 100 residue long protein would be a 100 dimensional object with 20 possible values, i.e., the 20 naturally occurring amino acids, in each dimension. Each one of these proteins has a corresponding fitness on some complex landscape. Models of such "fitness landscapes" were first studied by Sewall Wright (Wright (1932) "The roles of mutation, inbreeding, crossbreeding and selection in evolution," *Proceedings of 6th International Conference on Genetics,* 1:356-366) but have since been expanded on by others (Eigen, M. (1971) "Self organization of matter and the evolution of biological macromolecules," *Naturwissenschaften,* 58(10):465-523; Kauffman, S. et al. (1987) "Towards a general theory of adaptive walks on rugged landscapes," *J. Theor. Biol.,* 128(1):11-45; Kauffman, E. S., et al. (1989) "The NK model of rugged fitness landscapes and its application to maturation of the immune response," *J. Theor. Biol.,* 141(2):211-45; Schuster, P., et al. (1994) "Landscapes: complex optimization problems and biopolymer structures," *Comput. Chem.,* 18(3):295-324; Govindarajan, S. et al. (1997) "Evolution of model proteins on a foldability landscape," *Proteins,* 29(4):461-6). The sequence space of proteins is immense and is impossible to explore exhaustively. Accordingly, new ways to efficiently search sequence space to identify functional proteins would be highly desirable.

SUMMARY

One aspect of the present invention pertains to methods, apparatus, and software for identifying amino acid residues for variation in a protein variant library. These residues are then varied in the sequences of protein variants in the library in order to affect a desired activity such as stability, catalytic activity, therapeutic activity, resistance to a pathogen or toxin, toxicity, etc. The method of this aspect may be described by the following sequence of operations: (a) receiving data characterizing a training set of a protein variant library; (b) from the data, developing a sequence activity model that predicts activity as a function of amino acid residue type and corresponding position in the sequence; and (c) using the sequence activity model to identify one or more amino acid residues at specific positions in the systematically varied sequences that are to be varied in order to impact the desired activity. In this method, the protein variants in the library may have systematically varied sequences. Further, the data provides activity and sequence information for each protein variant in the training set.

In some embodiments, the method also includes (d) using the sequence activity model to identify one or more amino acid residues that are to remain fixed (as opposed to being varied) in new protein variant library.

The protein variant library may include proteins from various sources. In one example, the members include naturally occurring proteins such as those encoded by members of a single gene family. In another example, the members include proteins obtained by using a recombination-based diversity generation mechanism. Classical DNA shuffling (i.e., DNA fragmentation-mediated recombination) or synthetic DNA shuffling (i.e., synthetic oligonucleotide-mediated recombination) may be performed on nucleic acids encoding all or part of one or more naturally occurring parent proteins for this purpose. In still another example, the members are obtained by performing DOE to identify the systematically varied sequences.

Generally, the sequence activity model may be of any form that does a good job of predicting activity from sequence information. In a preferred embodiment, the model is a regression model such as a partial least squares model or a principal component regression model. In another example, the model is a neural network.

Using the sequence activity model to identify residues for fixing or variation may involve any of many different possible analytical techniques. In some cases, a "reference sequence" is used to define the variations. Such sequence may be one predicted by the model to have a highest value (or one of the highest values) of the desired activity. In another case, the reference sequence may be that of a member of the original protein variant library. From the reference sequence, the method may select subsequences for effecting the variations. In addition or alternatively, the sequence activity model ranks residue positions (or specific residues at certain positions) in order of impact on the desired activity.

One goal of the method may be to generate a new protein variant library. As part of this process, the method may identify sequences that are to be used for generating this new library. Such sequences include variations on the residues identified in (c) above or are precursors used to subsequently introduce such variations. The sequences may be modified by performing mutagenesis or a recombination-based diversity generation mechanism to generate the new library of protein variants. This may form part of a directed evolution procedure. The new library may also be used in developing a new sequence activity model.

In some embodiments, the method involves selecting one or more members of the new protein variant library for production. One or more of these may then be synthesized and/or expressed in an expression system.

Another aspect of the invention pertains to methods for defining a library of biological molecules. Such methods may be characterized by the following sequence of operations: (a) receiving an original set of data points representing the activity and sequence of multiple biological molecules in a training set; (b) constructing a bootstrap set of data points selected, with replacement, from the original set of data points; (c) generating a model from the bootstrap set, which model comprises indicators of the relative importance of individual residues or other units in biological molecules represented by the data points in the bootstrap set; (d) repeating (b) and (c) multiple times to generate multiple values of each indicator from the models generated in (c); (e) for each indicator, determining (i) an average or mean value of the multiple values and (ii) a statistical indication of the distribution of the multiple values; (f) ranking the individual residues or other units on basis of their respective values of (i) and (ii) determined in (e); and (g) toggling particular ones of the individual residues or other units based on rankings produced in (f) to thereby define the library of biological molecules.

Yet another aspect of the invention pertains to apparatus and computer program products including machine-readable media on which are provided program instructions and/or arrangements of data for implementing the methods and software systems described above. Frequently, the program instructions are provided as code for performing certain method operations. Data, if employed to implement features of this invention, may be provided as data structures, database tables, data objects, or other appropriate arrangements of specified information. Any of the methods or systems of this invention may be represented, in whole or in part, as such program instructions and/or data provided on machine-readable media.

These and other features of the present invention will be described in more detail below in the detailed description of the invention and in conjunction with the following figures.

DETAILED DISCUSSION OF THE INVENTION

I. Definitions

Figure 1A:
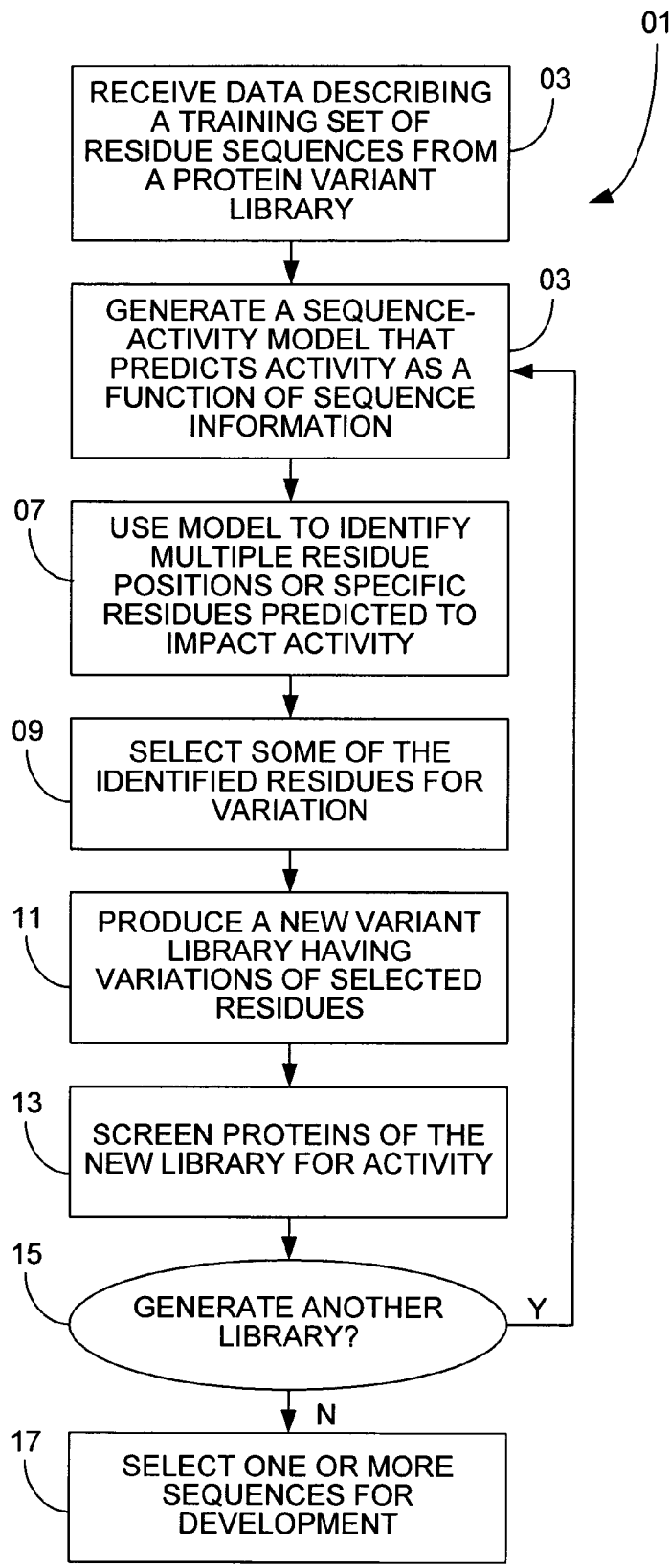
FIG. 1A is a flow chart depicting a sequence of operations, including identifying particular residues for variation, that may be used to generate one or more generations of protein variant libraries.

Before describing the present invention in detail, it is to be understood that this invention is not limited to particular compositions or systems, which can, of course vary. It is also to be understood that the terminology used herein is for the purpose of describing particular embodiments only, and is not intended to be limiting. As used in this specification and appended claims, the singular forms "a", "an", and "the" include plural referents unless the content and context clearly dictates otherwise. Thus, for example, reference to "a device" includes a combination of two or more such devices, and the like. Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected).

The following definitions and those included throughout this disclosure supplement those known to persons of skill in the art.

A "bio-molecule" refers to a molecule that is generally found in a biological organism. Preferred biological molecules include biological macromolecules that are typically polymeric in nature being composed of multiple subunits (i.e., "biopolymers"). Typical bio-molecules include, but are not limited to molecules that share some structural features with naturally occurring polymers such as an RNAs (formed from nucleotide subunits), DNAs (formed from nucleotide subunits), and polypeptides (formed from amino acid subunits), including, e.g., RNAs, RNA analogues, DNAs, DNA analogues, polypeptides, polypeptide analogues, peptide nucleic acids (PNAs), combinations of RNA and DNA (e.g., chimeraplasts), or the like. Bio-molecules also include, e.g., lipids, carbohydrates, or other organic molecules that are made by one or more genetically encodable molecules (e.g., one or more enzymes or enzyme pathways) or the like.

The term "nucleic acid" refers to deoxyribonucleotides or ribonucleotides and polymers (e.g., oligonucleotides, polynucleotides, etc.) thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with, e.g., oligonucleotide, polynucleotide, gene, cDNA, and mRNA encoded by a gene.

A "nucleic acid sequence" refers to the order and identity of the nucleotides comprising a nucleic acid.

A "polynucleotide" is a polymer of nucleotides (A, C, T, U, G, etc. or naturally occurring or artificial nucleotide analogues) or a character string representing a polymer of nucleotides, depending on context. Either the given nucleic acid or the complementary nucleic acid can be determined from any specified polynucleotide sequence.

The term "gene" is used broadly to refer to any segment of DNA associated with a biological function. Thus, genes include coding sequences and optionally, the regulatory sequences required for their expression. Genes also optionally include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Two nucleic acids are "recombined" when sequences from each of the two nucleic acids are combined in a progeny nucleic acid. Two sequences are "directly" recombined when both of the nucleic acids are substrates for recombination.

The terms "polypeptide" and "protein" are used interchangeably herein to refer to a polymer of amino acid residues. Typically, the polymer has at least about 30 amino acid residues, and usually at least about 50 amino acid residues. More typically, they contain at least about 100 amino acid residues. The terms apply to amino acid polymers in which one or more amino acid residues are analogs, derivatives or mimetics of corresponding naturally occurring amino acids, as well as to naturally occurring amino acid polymers. For example, polypeptides can be modified or derivatized, e.g., by the addition of carbohydrate residues to form glycoproteins. The terms "polypeptide," and "protein" include glycoproteins, as well as non-glycoproteins.

A "motif" refers to a pattern of subunits in or among biological molecules. For example, the motif can refer to a subunit pattern of the unencoded biological molecule or to a subunit pattern of an encoded representation of a biological molecule.

"Screening" refers to the process in which one or more properties of one or more bio-molecule is determined. For example, typical screening processes include those in which one or more properties of one or more members of one or more libraries is/are determined.

"Selection" refers to the process in which one or more bio-molecules are identified as having one or more properties of interest. Thus, for example, one can screen a library to determine one or more properties of one or more library members. If one or more of the library members is/are identified as possessing a property of interest, it is selected. Selection can include the isolation of a library member, but this is not necessary. Further, selection and screening can be, and often are, simultaneous.

The term "covariation" refers to the correlated variation of two or more variables (e.g., amino acids in a polypeptide, etc.).

"Genetic algorithms" are processes which mimic evolutionary processes. Genetic algorithms (GAs) are used in a wide variety of fields to solve problems which are not fully characterized or too complex to allow full characterization, but for which some analytical evaluation is available. That is, GAs are used to solve problems which can be evaluated by some quantifiable measure for the relative value of a solution (or at least the relative value of one potential solution in comparison to another). In the context of the present invention, a genetic algorithm is a process for selecting or manipulating character strings in a computer, typically where the character string corresponds to one or more biological molecules (e.g., nucleic acids, proteins, PNAs, or the like).

"Directed evolution" or "artificial evolution" refers to a process of artificially changing a character string by artificial selection, recombination, or other manipulation, i.e., which occurs in a reproductive population in which there are (1) varieties of individuals, with some varieties being (2) heritable, of which some varieties (3) differ in fitness (reproductive success determined by outcome of selection for a predetermined property (desired characteristic). The reproductive population can be, e.g., a physical population or a virtual population in a computer system.

"Genetic operators" are user-defined operations, or sets of operations, each including a set of logical instructions for manipulating character strings. Genetic operators are applied to cause changes in populations of individuals in order to find interesting (useful) regions of the search space (populations of individuals with predetermined desired properties) by predetermined means of selection. Predetermined (or partially predetermined) means of selection include computational tools (operators comprising logical steps guided by analysis of information describing libraries of character strings), and physical tools for analysis of physical properties of physical objects, which can be built (synthesized) from matter with the purpose of physically creating a representation of information describing libraries of character strings. In a preferred embodiment, some or all of the logical operations are performed in a digital system.

When referring to operations on strings (e.g., recombinations, hybridizations, elongations, fragmentations, segmentations, insertions, deletions, transformations, etc.) it will be appreciated that the operation can be performed on the encoded representation of a biological molecule or on the "molecule" prior to encoding so that the encoded representation captures the operation.

A "data structure" refers to the organization and optionally associated device for the storage of information, typically multiple "pieces" of information. The data structure can be a simple recordation of the information (e.g., a list) or the data structure can contain additional information (e.g., annotations) regarding the information contained therein, can establish relationships between the various "members" (i.e., information "pieces") of the data structure, and can provide pointers or links to resources external to the data structure. The data structure can be intangible but is rendered tangible when stored or represented in a tangible medium (e.g., paper, computer readable medium, etc.). The data structure can represent various information architectures including, but not limited to simple lists, linked lists, indexed lists, data tables, indexes, hash indices, flat file databases, relational databases, local databases, distributed databases, thin client databases, and the like. In preferred embodiments, the data structure provides fields sufficient for the storage of one or more character strings. The data structure is optionally organized to permit alignment of the character strings and, optionally, to store information regarding the alignment and/or string similarities and/or string differences. In one embodiment, this information is in the form of alignment "scores" (e.g., similarity indices) and/or alignment maps showing individual subunit (e.g., nucleotide in the case of nucleic acid) alignments. The term "encoded character string" refers to a representation of a biological molecule that preserves desired sequence/structural information regarding that molecule. As noted throughout, non-sequence properties of bio-molecules can be stored in a data structure and alignments of such non-sequence properties, in a manner analogous to sequence based alignment can be practiced.

It is generally assumed that two nucleic acids have common ancestry when they demonstrate sequence similarity. However, the exact level of sequence similarity necessary to establish homology varies in the art. In general, for purposes of this disclosure, two nucleic acid sequences are deemed to be homologous when they share enough sequence identity to permit direct recombination to occur between the two sequences.

A "phylogenetic family" refers to organisms, nucleic acid sequences, polypeptides sequences, or the like that share a common evolutionary relationship or lineage pattern.

A "subsequence" or "fragment" is any portion of an entire sequence of nucleic acids or amino acids.

A "library" or "population" refers to a collection of at least two different molecules and/or character strings, such as nucleic acid sequences (e.g., genes, oligonucleotides, etc.) or expression products (e.g., enzymes) therefrom. A library or population generally includes a number of different molecules. For example, a library or population typically includes at least about 10 different molecules. Large libraries typically include at least about 100 different molecules, more typically at least about 1000 different molecules. For some applications, the library includes at least about 10000 or more different molecules.

"Classification And Regression Trees" or "CART" refers to a classification tree program that uses an exhaustive grid search of all possible univariate splits to find the splits for a classification tree.

"Systematic variance" refers to different descriptors of an item or set of items being changed in different combinations.

"Systematically varied data" refers to data produced, derived, or resulting from different descriptors of an item or set of items being changed in different combinations. Many different descriptors can be changed at the same time, but in different combinations. For example, activity data gathered from polypeptides in which combinations of amino acids have been changed is systematically varied data.

A "descriptor" refers to something that serves to describe or identify an item. For example, characters in a character string can be descriptors of amino acids in a polypeptide being represented by the character string.

A "hyperbox" refers to a selected region in the objective space (e.g., sequence space) that includes at least one individual (e.g., a scored bio-molecule or chracter string representation of the bio-molecule) that lies at least proximate to a Pareto front in a given set of data.

The terms "sequence" and "character strings" are used interchangeably herein to refer to the order and identity of amino acid residues in a protein (i.e., a protein sequence or protein character string) or to the order and identity of nucleotides in a nucleic acid (i.e., a nucleic acid sequence or nucleic acid character string).

II. Generating Improved Protein Variant Libraries

In accordance with the present invention, various methods are provided for generating new protein variant libraries that can be used to explore protein sequence and activity space. A feature of many such methods is a procedure for identifying amino acid residues in a protein sequence that are predicted to impact a desired activity. As one example, such procedure includes the following operations:

(a) receiving data characterizing a training set of a protein variants, wherein the data provides activity and sequence information for each protein variant in the training set;

(b) from the data, developing a sequence activity model that predicts activity as a function of amino acid residue type and corresponding position in the sequence;

(c) using the sequence activity model to identify one or more amino acid residues at specific positions in one or more protein variants that are to be varied in order to impact the desired activity.

Other methods including slight variations of this method are within the scope of the present invention as set forth herein.

FIG. 1A presents a flow chart showing various operations that may be performed in the order depicted or in some other order. As shown, a process 01 begins at a block 03 with receipt of data describing a training set comprising residue sequences for a protein variant library. In other words, the training set data is derived from a protein variant library. Typically that data will include, for each protein in the library, a complete or partial residue sequence together with an activity value. In some cases, multiple types of activities (e.g., rate constant and thermal stability) are provided together in the training set.

In many embodiments, the individual members of the protein variant library represent a wide range of sequences and activities. This allows one to generate a sequence-activity model having applicability over a broad region of sequence space. Techniques for generating such diverse libraries include systematic variation of protein sequences and directed evolution techniques. Both of these are described in more detail elsewhere herein.

Activity data may be obtained by assays or screens appropriately designed to measure activity magnitudes. Such techniques are well known and are not central to this invention. The principles for designing appropriate assays or screens are widely understood. Techniques for obtaining protein sequences are also well known and are not central to this invention. The activity used with this invention may be protein stability (e.g., thermal stability). However, many important embodiments consider other activities such as catalytic activity, resistance to pathogens and/or toxins, therapeutic activity, toxicity, and the like.

After the training set data has been generated or acquired, the process uses it to generate a sequence-activity model that predicts activity as a function of sequence information. See block 05. Such model is an expression, algorithm or other tool that predicts the relative activity of a particular protein when provided with sequence information for that protein. In other words, protein sequence information is an input and activity prediction is an output. For many embodiments of this invention, the model can also rank the contribution of various residues to activity. Methods of generating such models (e.g., partial least squares regression (PLS), principal component regression (PCR), and multiple linear regression (MLR)) will be discussed below, along with the format of the independent variables (sequence information), the format of the dependent variable(s) (activity), and the form of the model itself (e.g., a linear first order expression).

A model generated at block 05 is employed to identify multiple residue positions (e.g., position 35) or specific residue values (e.g. glutamine at position 35) that are predicted to impact activity. See block 07. In addition to identifying such positions, it may "rank" the residue positions or residue values based on their contributions to activity. For example, the model may predict that glutamine at position 35 has the most pronounced effect on activity, phenylalanine at position 208 has the second most pronounced effect, and so on. In a specific approach described below, PLS or PCR regression coefficients are employed to rank the importance of specific residues. In another specific approach, a PLS load matrix is employed to rank the importance of specific residue positions.

After the process has identified residues that impact activity, some of them are selected for variation as indicated at a block 09. This is done for the purpose of exploring sequence space. Residues are selected using any of a number of different selection protocols, some of which will be described below. In one example, specific residues predicted to have the biggest beneficial impact on activity are preserved; in other words, they are not varied. A certain number of other residues predicted to have a lesser impact are, however, selected for variation. In another example, the residue positions found to have the biggest impact on activity are selected, but only if they are found to vary in high performing members of the training set. For example, if the model predicts that residue position 197 has the biggest impact on activity, but all or most of the proteins with high activity have leucine at this position, then position 197 would not be selected for variation—in this approach. All proteins in a next generation library would have leucine at position 197. However, if some "good" proteins had valine at this position and others had leucine, then the process would choose to vary the amino acid at this position.

After the residues for variation have been identified, the method next generates a new variant library having the specified residue variation. See block 11. Various methodologies are available for this purpose. In one example, an in vitro or in vivo recombination-based diversity generation mechanism is performed to generate the new variant library. Such procedures may employ oligonucleotides containing sequences or subsequences for encoding the proteins of the parental variant library. Some of the oligonucleotides will be closely related, differing only in the choice of codons for alternate amino acids selected for variation at 09. The recombination-based diversity generation mechanism may be performed for one or multiple cycles. If multiple cycles are used, each involves a screening step to identify which variants have acceptable performance to be used in a next recombination cycle. This is a form of directed evolution.

In a different example, a "reference" protein sequence is chosen and the residues selected at 09 are "toggled" to identify individual members of the variant library. The new proteins so identified are synthesized by an appropriate technique to generate the new library. In one example, the reference sequence may be a top-performing member of the training set or a "best" sequence predicted by a PLS or PCR model.

In another approach, the sequence activity model is used as a "fitness function" in a genetic algorithm for exploring sequence space. After one or more rounds of the genetic algorithm (with each round using the fitness function to select one or more possible sequences for a genetic operation), a next generation library is identified for use as described in this flow chart.

After the new library has been produced, it is screened for activity, as indicated in a block 13. Ideally, the new library will present one or more members with better activity than was observed in the previous library. However, even without such advantage, the new library can provide beneficial information. Its members may be employed for generating improved models that account for the effects of the variations selected in 09, and thereby more accurately predict activity across wider regions of sequence space. Further, the library may represent a passage in sequence space from a local maximum toward a global maximum (in activity).

Depending on the goal of process 01, it may be desirable to generate a series of new protein variant libraries, with each one providing new members of a training set. The updated training set is then used to generate an improved model. To this end, process 01 is shown with a decision operation 15, which determines whether yet another protein variant library should be produced. Various criteria can be used to make this decision. Examples include the number of protein variant libraries generated so far, the activity of top proteins from the current library, the magnitude of activity desired, and the level of improvement observed in recent new libraries.

Assuming that the process is to continue with a new library, the process returns to operation 05 where a new sequence-activity model is generated from sequence and activity data obtained for the current protein variant library. In other words, the sequence and activity data for the current protein variant library serves as part of the training set for the new model (or it may serve as the entire training set). Thereafter, operations 07, 09, 11, 13, and 15 are performed as described above, but with the new model.

At some point, in process 01, this cycle will end and no new library will be generated. At that point, the process may simply terminate or one or more sequences from one or more of the libraries may be selected for development and/or manufacture. See block 17.

A. Choosing Protein Variant Libraries

Protein variant libraries are groups of multiple proteins generated by methods of this invention. Protein variant libraries also provide the data for training sets used to generate sequence-activity models. The number of proteins included in a protein variant library depends on the application and the cost.

In one example, the protein variant library is generated from one or more naturally occurring proteins. In one example, these are protein members encoded by a single gene family. Other starting points for the library may be used. From these seed or starting proteins, the library may be generated by various techniques. In one case, the library is generated by classical DNA shuffling (i.e., DNA fragmentation-mediated recombination as described in Stemmer (1994) Proc. Natl. Acad. Sci. USA 10747-10751 and WO 95/22625) or synthetic DNA shuffling (i.e., synthetic oligonucleotide-mediated recombination as described in Ness et al. (2002) Nature Biotechnology 20:1251-1255 and WO 00/42561) on nucleic acids encoding part or all of one or more parent proteins. In another case, a single starting sequence is modified in various ways to generate the library. Preferably, the library is generated by systematically varying the individual residues. In one example, a design of experiment (DOE) methodology is employed to identify the systematically varied sequences. In another example, a "wet lab" procedure such as oligonucleotide-mediated recombination is used to introduce some level of systematic variation.

As used herein, the term "systematically varied sequences" refers to a set of sequences in which each residue is seen in multiple contexts. In principle, the level of systematic variation can be quantified by the degree to which the sequences are orthogonal from one another (maximally different compared to the mean). In practice, the process does not depend on having maximally orthogonal sequences, however, the quality of the model will be improved in direct relation to the orthogonality of the sequence space tested. In a simple example, a peptide sequence is systematically varied by identifying two residue positions, each of which can have one of two different amino acids. A maximally diverse library includes all four possible sequences. Such maximal systematic variation increases exponentially with the number of variable positions; e.g., by $2^N$, when there are 2 options at each of N residue positions. Those having ordinary skill in the art will readily recognize that maximal systematic variation, however, is not required by the invention methods. Systematic variation provides a mechanism for identifying a relatively small set of sequences for testing that provides a good sampling of sequence space.

Protein variants having systematically varied sequences can be obtained in a number of ways using techniques that are well known to those having ordinary skill in the art. Suitable methods include recombination-based methods that generate variants based on one or more "parental" polynucleotide sequences. Polynucleotide sequences can be recombined using a variety of techniques, including, for example, DNAse digestion of polynucleotides to be recombined followed by ligation and/or PCR reassembly of the nucleic acids. These methods include those described in, for example, Stemmer (1994) *Proc. Natl. Acad. Sci. USA*, 91:10747-10751, U.S. Pat. No. 5,605,793, "Methods for In Vitro Recombination," U.S. Pat. No. 5,811,238, "Methods for Generating Polynucleotides having Desired Characteristics by Iterative Selection and Recombination," U.S. Pat. No. 5,830,721, "DNA Mutagenesis by Random Fragmentation and Reassembly," U.S. Pat. No. 5,834,252, "End Complementary Polymerase Reaction," U.S. Pat. No. 5,837,458, "Methods and Compositions for Cellular and Metabolic Engineering," "WO/42832, "Recombination of Polynucleotide Sequences Using Random or Defined Primers," WO 98/27230, "Methods and Compositions for Polypeptide Engineering," WO 99/29902, "Method for Creating Polynucleotide and Polypeptide Sequences," and the like.

Synthetic recombination methods are also particularly well suited for generating protein variant libraries with systematic variation. In synthetic recombination methods, a plurality of oligonucleotides are synthesized which collectively encode a plurality of the genes to be recombined. Typically the oligonucleotides collectively encode sequences derived from homologous parental genes. For example, homologous genes of interest are aligned using a sequence alignment program such as BLAST (Atschul, et al., *J. Mol. Biol.*, 215:403-410 (1990). Nucleotides corresponding to amino acid variations between the homologues are noted. These variations are optionally further restricted to a subset of the total possible variations based on covariation analysis of the parental sequences, functional information for the parental sequences, selection of conservative or non-conservative changes between the parental sequences, or other like criteria. Variations are optionally further increased to encode additional amino acid diversity at positions identified by, for example, covariation analysis of the parental sequences, functional information for the parental sequences, selection of conservative or non-conservative changes between the parental sequences, or apparent tolerance of a position for variation. The result is a degenerate gene sequence encoding a consensus amino acid sequence derived from the parental gene sequences, with degenerate nucleotides at positions encoding amino acid variations. Oligonucleotides are designed which contain the nucleotides required to assemble the diversity present in the degenerate gene. Details regarding such approaches can be found in, for example, Ness et al. (2002), *Nature Biotechnology* 20:1251-1255, WO 00/42561, "Oligonucleotide Mediated Nucleic Acid Recombination," WO 00/42560, "Methods for Making Character Strings, Polynucleotides and Polypeptides having Desired Characteristics," WO 01/75767, "In Silico Cross-Over Site Selection," and WO 01/64864, "Single-Stranded Nucleic Acid Template-Mediated Recombination and Nucleic Acid Fragment Isolation."

The polynucleotide variant sequences are then transcribed and translated, either in vitro or in vivo, to create a set or library of protein variant sequences.

The set of systematically varied sequences can also be designed a priori using design of experiment (DOE) methods to define the sequences in the data set. A description of DOE methods can be found in Diamond, W. J. (2001) *Practical Experiment Designs: for Engineers and Scientists*, John Wiley & Sons and in "Practical Experimental Design for engineers and scientists" by William J Drummond (1981)Van Nostrand Reinhold Co New York, "Statistics for experimenters" George E. P. Box, William G Hunter and J. Stuart Hunter (1978) John Wiley and Sons, New York, or, e.g., on the world wide web at itl.nist.gov/div898/handbook/. There are several computational packages available to perform the relevant mathematics, including Statistics Toolbox (MatLab), JMP, Statistica and Statease Design expert. The result is a systematically varied and orthogonal dispersed data set of sequences that is suitable for building the sequence activity model of the present invention. DOE-based data sets can be readily generated using either Plackett-Burman or Fractional Factorial designs. Id.

In engineering or chemical sciences, fractional factorial designs, for example, are used to define fewer experiments (than in full factorial designs) in which a factor is varied (toggled) between two or more levels. Optimization techniques are used to ensure that the experiments chosen are maximally informative in accounting for factor space variance. The same design approaches (e.g., fractional factorial, D-optimal design) can be applied in protein engineering to construct fewer sequences where a given number of positions are toggled between two or more residues. This set of sequences would be an optimal description of systematic variance present in the protein sequence space in question. Once activities for the corresponding molecules (e.g., polynucleotides can be constructed via gene synthesis in accordance with a reverse translation of the sequence designs, then expressed as polypeptides) are measured, a regression model which tends to be an optimal solution, is developed. It should be mentioned that there is no restriction on the number of sequences to be constructed.

An example of the DOE approach applied to protein engineering includes the following operations:

1) Identify positions to toggle based on the principles described earlier (present in parental sequences, level of conservation, etc.)
2) Create a DOE experiment using one of the commonly available statistical packages by defining the number of factors (variable positions), the number of levels (choices at each position), and the number of experiments to run. The information content of the output matrix (typically consisting of 1s and 0s that represent residue choices at each position) depends directly on the number of experiments to run (the more the better).
3) Use the output matrix to construct a protein alignment that codes the 1s and 0s back to specific residue choices at each position.
4) Synthesize the genes encoding the proteins represented in the protein alignment.
5) Test the proteins encoded by the synthesized genes in relevant assay(s).
6) Build a model on the tested genes/proteins.
7) Follow the steps described before to identify positions of importance and to build a subsequent library with improved fitness.

For example purposes, consider a protein in which the functionally best amino acid residues at 20 positions are to be determined, e.g., where there are 2 possible amino acids available at each position. In this case, a resolution IV factorial design would be appropriate. A resolution IV design is defined as one which is capable of elucidating the effects of all single variables, with no two-factor effects overlapping them. The design would then specify a set of 40 specific amino acid sequences that would cover the total diversity of $2^{20}$ (~1 million) possible sequences. These sequences are then generated by a standard gene synthesis protocol and the function and fitness of these clones is determined.

An alternative to the above approaches is to employ all available sequences, e.g., the GenBank® database and other public sources, to provide the protein variant library. Although this entails massive computational power, current technologies make the approach feasible. Mapping all available sequences provides an indication of sequence space regions of interest.

B. Generating a Sequence Activity Model & Using that Model to Identify Residue Positions for Variation As indicated above, a sequence-activity model used with the present invention relates protein sequence information to protein activity. The protein sequence information used by the model may take many forms. Frequently, it is a complete sequence of the amino acid residues in a protein; e.g., HGPVFSTGGA (SEQ ID NO: 1) . . . . In some cases, however, it may be unnecessary to provide the complete amino acid sequence. For example, it may be sufficient to provide only those residues that are to be varied in a particular research effort. At later stages in research, for example, many residues may be fixed and only limited regions of sequence space remain to be explored. In such situations, it may be convenient to provide sequence activity models that require, as inputs, only the identification of those residues in the regions of the protein where the exploration continues. Still further, some models may not require exact identities of residues at the residue positions, but instead identify one or more physical or chemical properties that characterize the amino acid at a particular residue position. For example, the model may require specification of residue positions by bulk, hydrophobicity, acidity, etc. In some models, combinations of such properties are employed.

The form of the sequence-activity model can vary widely, so long as it provides a vehicle for correctly approximating the relative activity of proteins based on sequence information. Generally, it will treat activity as a dependent variable and sequence/residue values as independent variables. Examples of the mathematical/logical form of models include linear and non-linear mathematical expressions of various orders, neural networks, classification and regression trees/graphs, clustering approaches, recursive partitioning, support vector machines, and the like. In one preferred embodiment, the model form is a linear additive model in which the products of coefficients and residue values are summed. In another preferred embodiment, the model form is a non-linear product of various sequence/residue terms, including certain residue cross-products (which represent interaction terms between residues).

Models are developed from a training set of activity versus sequence information to provide the mathematical/logical relationship between activity and sequence. This relationship is typically validated prior to use for predicting activity of new sequences or residue importance.

Various techniques for generating models are available. Frequently, such techniques are optimization or minimization techniques. Specific examples include partial least squares, various other regression techniques, as well as genetic programming optimization techniques, neural network techniques, recursive partitioning, and support vector machine techniques. Generally, the technique should produce a model that can distinguish residues that have a significant impact on activity from those that do not. Preferably, the model should also rank individual residues or residue positions based on their impact on activity.

In one important class of techniques, models are generated by a regression technique that identifies covariation of independent and dependent variables in a training set. Various regression techniques are known and widely used. Examples include multiple linear regression (MLR), principal component regression (PCR) and partial least squares regression (PLS).

MLR is the most basic of these techniques. It simply solves a set of coefficient equations for members of a training set. Each equation relates to the activity of a training set member (dependent variable) with the presence or absence of a particular residue at a particular position (independent variables). Depending upon the number of residue options in the training set, these expressions can be quite large.

Like MLS, PLS and PCR generate models from equations relating sequence activity to residue values. However, these techniques do so in a different manner. They first perform a coordinate transformation to reduce the number of independent variables. They then perform the regression on the transformed variables. In MLR, there are a potentially very large number of independent variables: two or more for each residue position that varies within the training set. Given that proteins and peptides of interest are often quite large and the training set may provide many different sequences, the number of independent variables can quickly become very large. By reducing the number of variables to focus on those that provide the most variation in the data set, PLS and PCR generally require fewer samples and simplify the problem of generating a model.

PCR is similar to PLS regression in that the actual regression is done on a relatively small number of latent variables obtained by coordinate transformation of the raw independent variables (residue values). The difference between PLS and PCR is that the latent variables in PCR are constructed by maximizing covariation between the independent variables (residue values). In PLS regression, the latent variables are constructed in such a way as to maximize the covariation between the independent variables and the dependent variables (activity values). Partial Least Squares regression is described in Hand, D. J., et al. (2001) *Principles of Data Mining (Adaptive Computation and Machine Learning)*, Boston, Mass., MIT Press, and in Geladi, et al. (1986) "Partial Least-Squares Regression: a Tutorial," *Anal. Chim. Acta*, 198:1-17. Both of these references are incorporated herein by reference for all purposes.

In PCR and PLS, the direct result of the regression is an expression for activity that is a function of the weighted latent variables. This expression can be transformed to an expression for activity as a function of the original independent variables by performing a coordinate transformation that converts the latent variables back to the original independent variables.

In essence, both PCR and PLS first reduce the dimensionality of the information contained in the training set and then perform a regression analysis on a transformed data set; which has been transformed to produce new independent variables, but preserves the original dependent variable values. The transformed versions of the data sets may result in only a relatively few expressions for performing the regression analysis. Compare this with a situation where no dimension reduction is performed. In that situation, each separate residue for which there can be a variation must be considered. This can be a very large set of coefficients; $2^N$ coefficients, where N is the number of residue positions that may vary in the training set. In a typical principal component analysis, only 3, 4, 5, 6 principal components are employed.

Another class of tools that can be used to generate models in accordance with this invention is the support vector machines. These mathematical tools take as inputs training sets of sequences that have been classified into two or more groups based on activity. Support vector machines operate by weighting different members of a training set differently depending upon how close they are to a hyperplane interface separating "active" and "inactive" members of the training set. This technique requires that the scientist first decide which training set members to place in the active group and which training set members to place in the inactive group. This may be accomplished by choosing an appropriate numerical value of activity to serve as the boundary between active and inactive members of the training set. From this classification, the support vector machine will generate a vector, W, that can provide coefficient values for individual ones of the independent variables defining the sequences of the active and inactive group members in the training set. These coefficients can be used to "rank" individual residues as described elsewhere herein. The technique attempts to identify a hyperplane that maximizes the distance between the closest training set members on opposite sides of that plane. In another variation, support vector regression modeling is carried out. In this case, the dependent variable is a vector of continuous activity values. The support vector regression model will generate a coefficient vector, W, which can be used to rank individual residues.

SVMs have been used to look at large data sets in many studies and have been quite popular in the DNA microarray field. Their potential strengths include the ability to finely discriminate (by weighting) which factors separate samples from each other. To the extent that an SVM can tease out precisely which residues contribute to function, it can be a particularly useful tool for ranking residues in accordance with this invention. SVMs are described in S. Gunn (1998) "Support Vector Machines for Classification and Regressions," Technical Report, Faculty of Engineering and Applied Science, Department of Electronics and Computer Science, University of Southampton, which is incorporated herein by reference for all purposes.

Another model generation technique of interest is genetic programming. This technique employs a Darwinian style evolution to discover the formulae and rules that characterize the data of a training set. It can be used in regression problems of the types described herein. The underlying effect can be linear or non-linear. Genetic programming is described in R. Goodacre et al. (2000) "Detection of the Dipicolinic Acid Biomarker in *Bacillus* Spores Using Curie-Point Pyrolysis Mass Spectrometry and Fourier Transform Infrared Spectroscopy," *Anal. Chem.*, 72, 119-127, which is incorporated herein by reference for all purposes. Examples of software tools for performing genetic programming include the "GMAX" and the "GMAX-Bio" available from Aber Genomic Computing Ltd of Wales, UK.

In general, a regression model employed in the practice of the present invention has the following form:

$$y = \sum_{i=1}^{N} \sum_{j=1}^{M} c_{ij} x_{ij} \tag{1}$$

In this expression, y is predicted response, while $c_{ij}$ and $x_{ij}$ are the regression coefficient and bit value (i.e., residue choice) respectively at position i in the sequence. There are N residue positions in the sequences of the protein variant library and each of these may be occupied by one or more residues. At any given position, there may be j=1 through M separate residue types. This model assumes a linear (additive) relationship between the residues at every position. An expanded version of equation 1 follows:

$$y = c_0 + c_{11}x_{11} + c_{12}x_{12} + \ldots c_{1M}x_{1M} + c_{21}x_{21} + c_{22}x_{22} + \ldots c_{2M}x_{2M} + \ldots + c_{NM}x_{NM}$$

As indicated, data in the form of activity and sequence information is derived from the initial protein variant library and used to determine the regression coefficients of the model. The bit values are first identified from an alignment of the protein variant sequences. Amino acid residue positions are identified from among the protein variant sequences in which the amino acid residues in those positions differ between sequences. Amino acid residue information in some or all of these variable residue positions may be incorporated in the sequence activity model.

Table I contains sequence information in the form of variable residue positions and residue type for 10 illustrative variant proteins, along with activity values corresponding to each variant protein. Understand, that these are representative members of a larger set that is required to generate enough equations to solve for all the coefficients. Thus, for example, for the illustrative protein variant sequences in Table I, positions 10, 166, 175, and 340, are variable residue positions and all other positions, i.e., those not indicated in the Table, contain residues that are identical between Variants 1-10.

TABLE I

Illustrative Sequence and Activity Data

| | Variable Positions: | | | | |
|---|---|---|---|---|---|
| | 10 | 166 | 175 | 340 | y (activity) |
| Variant 1 | Ala | Ser | Gly | Phe | $y_1$ |
| Variant 2 | Asp | Phe | Val | Ala | $y_2$ |
| Variant 3 | Lys | Leu | Gly | Ala | $y_3$ |
| Variant 4 | Asp | Ile | Val | Phe | $y_4$ |
| Variant 5 | Ala | Ile | Val | Ala | $y_5$ |
| Variant 6 | Asp | Ser | Gly | Phe | $y_6$ |
| Variant 7 | Lys | Phe | Gly | Phe | $y_7$ |
| Variant 8 | Ala | Phe | Val | Ala | $y_8$ |
| Variant 9 | Lys | Ser | Gly | Phe | $y_9$ |
| Variant 10 | Asp | Leu | Val | Ala | $y_{10}$ |
| and so on. | | | | | |

Thus, based on equation 1, a regression model can be derived from the systematically varied library in Table I, i.e.,:

$$y = c_0 + c_{10Ala}x_{10Ala} + c_{10Asp}x_{10Asp} + c_{10Lys}x_{10Lys} + c_{166Ser}x_{166Ser} + c_{166Phe}x_{166Phe} + c_{166Leu}x_{166Leu} + c_{166Ile}x_{166Ile} + c_{175Gly}x_{175Gly} + c_{175Val}x_{175Val} + c_{340Phe}x_{340Phe} + c_{340Ala}x_{340Ala} \quad (2)$$

The bit values (x variables) can be represented as either 1 or 0 reflecting the presence or absence of the designated amino acid residue or alternatively, 1 or –1. For example, using the 1 or 0 designation, $x_{10Ala}$ would be "1" for Variant 1 and "0" for Variant 2. Using the 1 or –1 designation, $x_{10Ala}$ would be "1" for Variant 1 and "–1" for Variant 2. The regression coefficients can thus be derived from regression equations based on the sequence activity information for all variants in library. Examples of such equations for Variants 1-10 (using the 1 or 0 designation for x) follow:

$$y_1 = c_0 + c_{10Ala}(1) + c_{10Asp}(0) + c_{10Lys}(0) + c_{166Ser}(1) + c_{166Phe}(0) + c_{166Leu}(0) + c_{166Ile}(0) + c_{175Gly}(1) + c_{175Val}(0) + c_{340Phe}(1) + c_{340Ala}(0)$$

$$y_2 = c_0 + c_{10Ala}(0) + c_{10Asp}(1) + c_{10Lys}(0) + c_{166Ser}(0) + c_{166Phe}(1) + c_{166Leu}(0) + c_{166Ile}(0) + c_{175Gly}(0) + c_{175Val}(1) + c_{340Phe}(0) + c_{340Ala}(1)$$

$$y_3 = c_0 + c_{10Ala}(0) + c_{10Asp}(0) + c_{10Lys}(1) + c_{166Ser}(0) + c_{166Phe}(0) + c_{166Leu}(1) + c_{166Ile}(0) + c_{175Gly}(1) + c_{175Val}(0) + c_{340Phe}(0) + c_{340Ala}(1)$$

$$y_4 = c_0 + c_{10Ala}(0) + c_{10Asp}(1) + c_{10Lys}(0) + c_{166Ser}(0) + c_{166Phe}(0) + c_{166Leu}(0) + c_{166Ile}(1) + c_{175Gly}(0) + c_{175Val}(1) + c_{340Phe}(1) + c_{340Ala}(0)$$

$$y_5 = c_0 + c_{10Ala}(1) + c_{10Asp}(0) + c_{10Lys}(0) + c_{166Ser}(0) + c_{166Phe}(0) + c_{166Leu}(0) + c_{166Ile}(1) + c_{175Gly}(0) + c_{175Val}(1) + c_{340Phe}(0) + c_{340Ala}(1)$$

$$y_6 = c_0 + c_{10Ala}(0) + c_{10Asp}(1) + c_{10Lys}(0) + c_{166Ser}(1) + c_{166Phe}(0) + c_{166Leu}(0) + c_{166Ile}(0) + c_{175Gly}(1) + c_{175Val}(0) + c_{340Phe}(1) + c_{340Ala}(0)$$

$$y_7 = c_0 + c_{10Ala}(0) + c_{10Asp}(0) + c_{10Lys}(1) + c_{166Ser}(0) + c_{166Phe}(1) + c_{166Leu}(0) + c_{166Ile}(0) + c_{175Gly}(1) + c_{175Val}(0) + c_{340Phe}(1) + c_{340Ala}(0)$$

$$y_8 = c_0 + c_{10Ala}(1) + c_{10Asp}(0) + c_{10Lys}(0) + c_{166Ser}(0) + c_{166Phe}(1) + c_{166Leu}(0) + c_{166Ile}(0) + c_{175Gly}(0) + c_{175Val}(1) + c_{340Phe}(0) + c_{340Ala}(1)$$

$$y_9 = c_0 + c_{10Ala}(0) + c_{10Asp}(0) + c_{10Lys}(1) + c_{166Ser}(1) + c_{166Phe}(0) + c_{166Leu}(0) + c_{166Ile}(0) + c_{175Gly}(1) + c_{175Val}(1) + c_{340Phe}(1) + c_{340Ala}(0)$$

$$y_{10} = c_0 + c_{10Ala}(0) + c_{10Asp}(1) + c_{10Lys}(0) + c_{166Ser}(0) + c_{166Phe}(0) + c_{166Leu}(1) + c_{166Ile}(0) + c_{175Gly}(0) + c_{175Val}(1) + c_{340Phe}(0) + c_{340Ala}(1)$$

The complete set of equations can be readily solved using a regression technique (e.g., PCR, PLS, or MLR) to determine the value for regression coefficients corresponding to each residue and position of interest. In this example, the relative magnitude of the regression coefficient correlates to the relative magnitude of contribution of that particular residue at the particular position to activity. The regression coefficients may then be ranked or otherwise categorized to determine which residues are more likely to favorably contribute to the desired activity. Table II provides illustrative regression coefficient values corresponding to the systematically varied library exemplified in Table I:

TABLE II

Illustrative Rank Ordering of Regression Coefficients

| REGRESSION COEFFICIENT | VALUE |
|---|---|
| $c_{166Ile}$ | 62.15 |
| $c_{175Gly}$ | 61.89 |
| $c_{10Asp}$ | 60.23 |
| $c_{340Ala}$ | 57.45 |
| $c_{10Ala}$ | 50.12 |
| $c_{166Phe}$ | 49.65 |
| $c_{166Leu}$ | 49.42 |
| $c_{340Phe}$ | 47.16 |
| $c_{166Ser}$ | 45.34 |
| $c_{175Val}$ | 43.65 |
| $c_{10Lys}$ | 40.15 |

The rank ordered list of regression coefficients can be used to construct a new library of protein variants that is optimized with respect to a desired activity (i.e., improved fitness). This can be done in various ways. In one case, it is accomplished by retaining the amino acid residues having coefficients with the highest observed values. These are the residues indicated by the regression model to contribute the most to desired activity. If negative descriptors are employed to identify residues (e.g., 1 for leucine and –1 for glycine), it becomes necessary to rank residue positions based on absolute value of the coefficient. Note that in such situations, there is typically only a single coefficient for each residue. The absolute value of the coefficient magnitude gives the ranking of the corresponding residue position. Then, it becomes necessary to consider the signs of the individual residues to determine whether each of them is detrimental or beneficial in terms of the desired activity.

Residues are generally considered in the order in which they are ranked. For each residue under consideration, the process determines whether to "toggle" that residue. The term "toggling" refers to the introduction of multiple amino acid residue types into a specific position in the sequences of protein variants in the optimized library. For example, serine may appear in position 166 in one protein variant, whereas phenylalanine may appear in position 166 in another protein variant in the same library. Amino acid residues that did not vary between protein variant sequences in the training set typically remain fixed in the optimized library.

An optimized protein variant library can be designed such that all of the identified "high" ranking regression coefficient residues are fixed, and the remaining lower ranking regression coefficient residues are toggled. The rationale for this being that one should search the local space surrounding the 'best' predicted protein. Note that the starting point "backbone" in which the toggles are introduced may be the best protein predicted by a model or an already validated 'best' protein from a screened library.

In an alternative approach, at least one or more, but not all of the high-ranking regression coefficient residues identified may be fixed in the optimized library, and the others toggled. This approach is recommended if it is desired not to drastically change the context of the other amino acid residues by incorporating too many changes at one time. Again, the starting point for toggling may be the best set of residues as predicted by the model or a best validated protein from an existing library. Or the starting point may be an "average" clone that models well. In this case, it may be desirable to toggle the residues predicted to be of higher importance. The rationale for this being that one should explore a larger space in search for activity hills previously omitted from the sampling. This type of library is typically more relevant in early rounds as it generates a more refined picture for subsequent rounds.

Alternatives to the above methodology involve different procedures for using residue importance (rankings) in determining which residues to toggle. In one such alternative, higher ranked residue positions are favored for toggling. The information needed in this approach includes the sequence of a best protein from the training set, a PLS or PCR predicted best sequence, and a ranking of residues from the PLS or PCR model. The "best" protein is a wet-lab validated "best" clone in the dataset (clone with the highest measured function that still models well, i.e., falls relatively close to the predicted value in cross validation). The method compares each residue from this protein with the corresponding residue from a "best predicted" sequence having the highest value of the desired activity. This is accomplished using, e.g., the loads matrix (described below), starting with the residue having the highest load. Alternatively, another measure of the PLS or PCR best-predicted sequence such as highest value of regression coefficient for each position is used. If the residue with the highest load or regression coefficient is not present in the 'best' clone, the method introduces that position as a toggle position for the subsequent library. If the residue is present in the best clone, the method will not treat the position as a toggle position, and it will move the next position in succession. The process is repeated for various residues, moving through successively lower load values, until the library is of sufficient size is generated.

The number of regression coefficient residues to retain, and number of regression coefficient residues to toggle, can be varied. Factors to consider include the desired library size, the magnitude of difference between regression coefficients, and the degree to which nonlinearity is thought to exist—retaining residues with small (neutral) coefficients may uncover important nonlinearities in subsequent rounds of evolution. Typical optimized protein variant libraries of the present invention contain about $2^N$ protein variants, where N represents the number of positions that are toggled between two residues. Stated another way, the diversity added by each additional toggle doubles the size of the library such that 10 toggle positions produces ~1,000 clones (1,024), 13 positions ~10,000 clones (8,192) and 20 positions ~1,000,000 clones (1,048,576). The appropriate size of library depends on factors such as cost of screen, ruggedness of landscape, preferred percentage sampling of space etc. In some cases, it has been found that a relatively large number of changed residues produces a library in which an inordinately large percentage of the clones are non-functional. Therefore for some applications, it may be recommended that the number of residues for toggling ranges from about 2 to about 13; i.e., the library size ranges from between about 4 and 10,000 clones.

In practice, one can pursue various subsequent round library strategies at the same time, with some strategies being more aggressive (fixing more "beneficial" residues) and other strategies being more conservative (fixing fewer "beneficial" residues in the hopes of exploring the space more thoroughly).

Optimized protein variant libraries can be generated using the recombination methods described herein, or alternatively, by gene synthesis methods, followed by in vivo or in vitro expression. The optimized protein variant libraries are then screened for desired activity, and sequenced. As indicated above in the discussion of FIG. 1A, the activity and sequence information from the optimized protein variant library can be employed to generate another sequence activity model from which a further optimized library can be designed, using the methods described herein. In one approach, all proteins from this new library are used as part of the dataset.

In varied approaches, a wet-lab validated 'best' (or one of the few best) protein in the current optimized library (i.e., a protein with the highest, or one of the few highest, measured function that still models well, i.e., falls relatively close to the predicted value in cross validation) may serve as a backbone where various schemes of changes are incorporated. In another approach, a wet-lab validated 'best' (or one of the few best) protein in the current library that may not model well may serve as a backbone where various schemes of changes are incorporated. In other approaches, a sequence predicted by the sequence activity model to have the highest value (or one of the highest values) of the desired activity may serve as the backbone. In these approaches, the dataset for the "next generation" library (and possibly a corresponding model) is obtained by changing residues in one or a few of the best proteins. In one embodiment, these changes comprise a systematic variation of the residues in the backbone. In some cases, the changes comprise various mutagenesis, recombination and/or subsequence selection techniques. Each of these may be performed in vitro, in vivo, or in silico.

Multiple other variations on the above approach are within the scope of this invention. As one example, the xij variables are representations of the physical or chemical properties of amino acids—rather than the exact identities of the amino acids themselves (leucine versus valine versus proline, ... ). Examples of such properties include lipophilicity, bulk, and electronic properties (e.g., formal charge, van der Waals surface area associated a partial charge, etc.). To implement this approach, the xij values representing amino acid residues can be presented in terms of their properties or principal components constructed from the properties.

In another variation, the xij variables represent nucleotides, rather than amino acid residues. The goal is to identify nucleic acid sequences that encode proteins for a protein variant library. By using nucleotides rather than amino acids, one can optimize on parameters other than merely specific activity. For example, protein expression in a particular host or vector may be a function of nucleotide sequence. Two different nucleotide sequences may encode a protein having one amino acid sequence, but one of the nucleotide sequences expresses greater quantities of protein and/or expresses the protein in a more active state. By using nucleotide sequences rather than amino acid sequences, the methods of this invention can optimize for expression properties, for example, as well as specific activity.

In a specific embodiment, the nucleotide sequence is represented as codons. Models may employ codons as the atomic unit of a nucleotide sequence such that the predicted activities are a function of various codons in the nucleotide sequence. Each codon together with its position in the overall nucleotide sequence serves as an independent variable for generating sequence activity models. Note that different codons for given amino acid express differently in a given organism. More specifically, each organism has a preferred codon, or distribution of codon frequencies, for a given amino acid. By using codons as the independent variables, the invention accounts for these preferences.

An outline of a particular method includes the following operations: (a) receiving data characterizing a training set of a protein variant library; (b) from the data, developing a sequence activity model that predicts activity as a function of nucleotide types and corresponding position in the nucleotide sequence; (c) using the sequence activity model to rank positions in a nucleotide sequence and/or nucleotide types at specific positions in the nucleotide sequence in order of impact on the desired activity; and (d) using the ranking to identify one or more nucleotides, in the nucleotide sequence, that are to be varied or fixed in order to impact the desired activity. As indicated, the nucleotides to be varied are preferably codons encoding particular amino acids.

Other variations of the above approach involve use of different techniques for ranking residues or otherwise characterizing them in terms of importance. In the above approach, the magnitudes of regression coefficients were used to rank residues. Residues having coefficients with large magnitudes (e.g., 166 Ile) were viewed as high-ranking residues. This characterization was used to decide whether or not to vary a particular residue in the generation of a new, optimized library of protein variants.

PLS and other techniques provide other information, beyond regression coefficient magnitude, that can be used to rank specific residues or residue positions. Techniques such as PLS and Principle Component Analysis (PCA) or PCR provide information in the form of principle components or latent vectors. These represent directions or vectors of maximum variation through multi-dimensional data sets such as the protein sequence-activity space employed in this invention. These latent vectors are functions of the various sequence dimensions; i.e., the individual residues or residue positions that comprise the protein sequences of the variant library used to construct the training set. A latent vector will therefore comprise a sum of contributions from each of the residue positions in the training set. Some positions will contribute more strongly to the direction of the vector. These will be manifest by relatively large "loads," i.e., the coefficients used to describe the vector. As a simple example, a training set may be comprised of tripeptides. The first latent vector will typically have contributions from all three residues.

Vector 1=$a1$(residue position 1)+$a2$(residue position 2)+$a3$(residue position 3)

The coefficients, a1, a2, and a3, are the loads. Because these reflect the importance of the corresponding residue positions to variation in the dataset, they can be used to rank the importance of individual residue positions for purposes of "toggling" decisions, as described above. Loads, like regression coefficients, may be used to rank residues at each toggled position. Various parameters describe the importance of these loads. Some such Variable Importance in Projection (VIP) make use of a load matrix, which is comprised of the loads for multiple latent vectors taken from a training set. In Variable Importance for PLS Projection, the importance of the ith variable (e.g., residue position) is computed by calculating VIP (variable importance in projection). For a given PLS dimension, a, $(VIN)_{ak}^2$ is equal to the squared PLS weight $(w_{ak})^2$ of a variable multiplied by the percent explained variability in y (dependent variable, e.g., certain function) by that PLS dimension. $(VIN)_{ak}^2$ is summed over all PLS dimensions (components). VIP is then calculated by dividing the sum by the total percent variability in y explained by the PLS model and multiplying by the number of variables in the model. Variables with large VIP, larger than 1, are the most relevant for correlating with a certain function (y) and hence highest ranked for purposes of making toggling decisions.

Another embodiment of the invention employs techniques that rank residues not simply by the magnitudes of their predicted contributions to activity, but by the confidence in those predicted contributions as well. In the methods described to this point, residues or nucleotides (including codons) are ranked based solely on the magnitude of the coefficients or principal components identified during model building. In many cases, this works well. But in some cases the researcher will be concerned with spurious values of the coefficients or principal components.

In a more statistically rigorous approach, the ranking is based on a combination of magnitude and distribution. Coefficients with both high magnitudes and tight distributions give the highest ranking. In some cases, one coefficient with a lower magnitude than another may be given a higher ranking by virtue of having less variation. Thus, some embodiments of the invention rank residues or nucleotides based on both magnitude and standard deviation or variance. Various techniques can be used to accomplish this. One of these, a bootstrap p-value approach, will now be described.

Figure 1B:
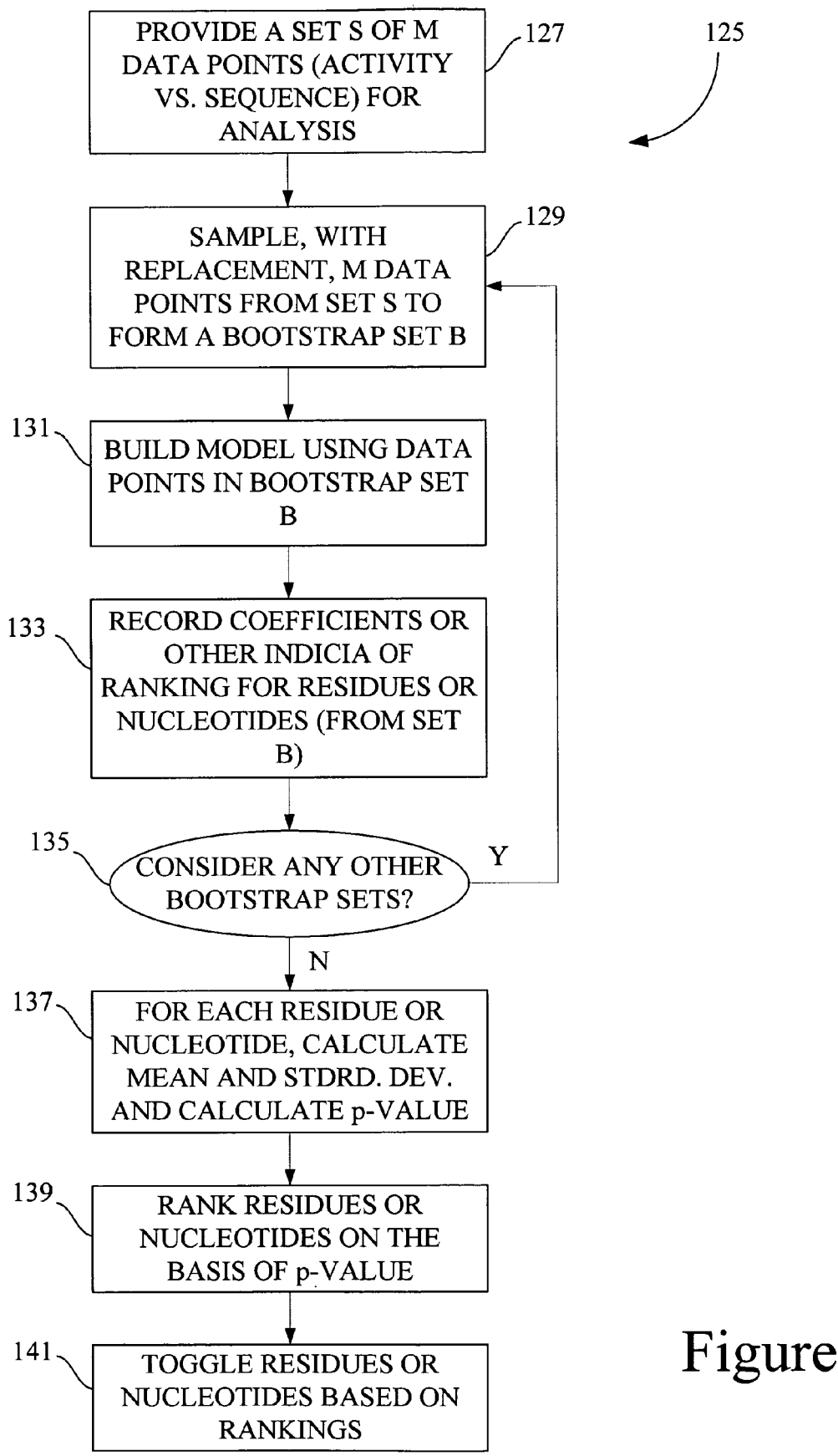
FIG. 1B is a flow chart depicting a bootstrap p-value method of generating protein variant libraries in accordance with an embodiment of this invention.

An example of a method that employs a bootstrap method is depicted in FIG. 1B. As shown there, a method 125 begins at a block 127 where an original data set S is provided. This may be a training set as described above. For example, it may be generated by systematically varying the individual residues of a starting sequence in any one of the manners described above. In the example of method 125, the data set S has M different data points (activity and sequence information collected from amino acid or nucleotide sequences) for use in the analysis.

From data set S, various bootstrap sets B are created. Each of these is obtained by sampling, with replacement, from set S to create a new set of M members—all taken from original set S. See block 129. The "with replacement" condition produces variations on the original set S. The new bootstrap set, B, will sometimes contain replicate samples from S. And, it may also lack certain samples originally contained in S.

As an example, consider a set S of 100 sequences. Each bootstrap set B used in the method contains itself 100 sequences. A bootstrap set B is created by randomly selecting each of the 100 member sequences from the 100 sequences in the original set S. Thus, it is possible that some sequences will be selected more than once and others will not be selected at all.

Using the bootstrap set B currently under consideration, the method next builds a model. See block 131. The model may be built as described above, using PLS, PCR, a SVM, genetic programming, etc. This model will provide coefficients or other indicia of ranking for the residues or nucleotides found in the various samples from set B. As shown at a block 133, these coefficients or other indicia are recorded for subsequent use.

Next, at a decision block 135, the method determines whether another bootstrap set should be created. If yes, the method returns to block 129 where a new bootstrap set B is created as described above. If no, the method proceeds to a block 137 discussed below. The decision at block 135 turns on how many different sets of coefficient values are to be used in assessing the distributions of those values. The number of sets B should be sufficient to generate accurate statistics. As an example, 100 to 1000 bootstrap sets are prepared and analyzed. This is represented as about 100 to 1000 passes through blocks 129, 131, and 133 of method 125.

After a sufficient number bootstrap sets B have been prepared and analyzed as described, decision 135 is answered in the negative. As indicated, the method then proceeds to block 137. There a mean and standard deviation of a coefficient (or other indicator generated by the model) is calculated for each residue or nucleotide (including codons) using the coefficient values (e.g., 100 to 1000 of them, one from each bootstrap set). From this information, the method can calculate the t-statistic and determine the confidence interval that the measured value is different from zero. From the t-statistic it calculates the p-value for the confidence interval. In this case, the smaller p-value the more confidence that the measured regression coefficient is different from zero.

Note that the p-value is but one of many different types of characterization that can account for the statistical variation in a coefficient or other indicator of residue importance. Examples include calculating 95 percent confidence intervals for regression coefficients and excluding any regression coefficient for consideration for which 95 percent confidence interval crosses zero line. Basically, any characterization that accounts for standard deviation, variance, or other statistically relevant measure of data distribution can be used. Such characterization preferably also accounts for the magnitude of the coefficients.

A large standard deviation can result from various sources. One source is poor measurements in the data set. Another is a limited representation of a particular residue or nucleotide in the original data set. In this latter case, some bootstrap sets will contain no occurrences of a particular residue or nucleotide. In such cases, the value of the coefficient for that residue will be zero. Other bootstrap sets will contain at least some occurrences of the residue or nucleotide and give a non-zero value of the corresponding coefficient. But the sets giving a zero value will cause the standard deviation of the coefficient to become relatively large. This reduces the confidence in the coefficient value and results in a lower rank. But this is to be expected, given that there is relatively little data on the residue or nucleotide in question.

Next, at a block 139, the method ranks the regression coefficients (or other indicators) from lower (best) p-value to highest (worst) p-value. This ranking correlates highly with the absolute value of the regression coefficients themselves, owing to the fact that the larger the absolute value, the more standard deviations removed from zero. Thus, for a given standard deviation, the p-value becomes smaller as the regression coefficient becomes larger. However, the absolute ranking will not always be the same with both p-value and pure magnitude methods, especially when relatively few data points are available to begin with in set S.

Finally, as shown at a block 141, the method fixes and toggles certain residues based on the rankings observed in the operation of block 139. This is essentially the same use of rankings described above for other embodiments. In one approach, the method fixes the best residues (now those with the lowest p-values) and toggles the others (those with highest p-values).

This method 125 has been shown in silico to perform well. Moreover, the p-value ranking approach naturally deals with single or few instance residues: the p-values will generally be higher (worse) because in the bootstrap process, those residues that did not appear often in the original data set will be less likely to get picked up at random. Even if their coefficients are large, their variability (measured in standard deviations) will be quite high as well. Intuitively, this is the desired result, since those residues that are not well represented (either have not seen with sufficient frequency or have lower regression coefficients) may be good candidates for toggling in the next round of library design.

III. Identification of Target Bio-Molecules with Desired Properties and/or for Artificial Evolution A. Library Design Using Pareto Front Optimization for Multiple Properties The present invention provides methods that utilize Pareto front optimization to select clones for carrying out future rounds of artificial evolution (e.g., DNA shuffling, etc.) in connection with the optimization of multiple polypeptide properties (i.e., multiple objectives). Pareto front optimization is a multi-objective evolutionary algorithm that simultaneously improves two or more desired objectives.

Figure 2:
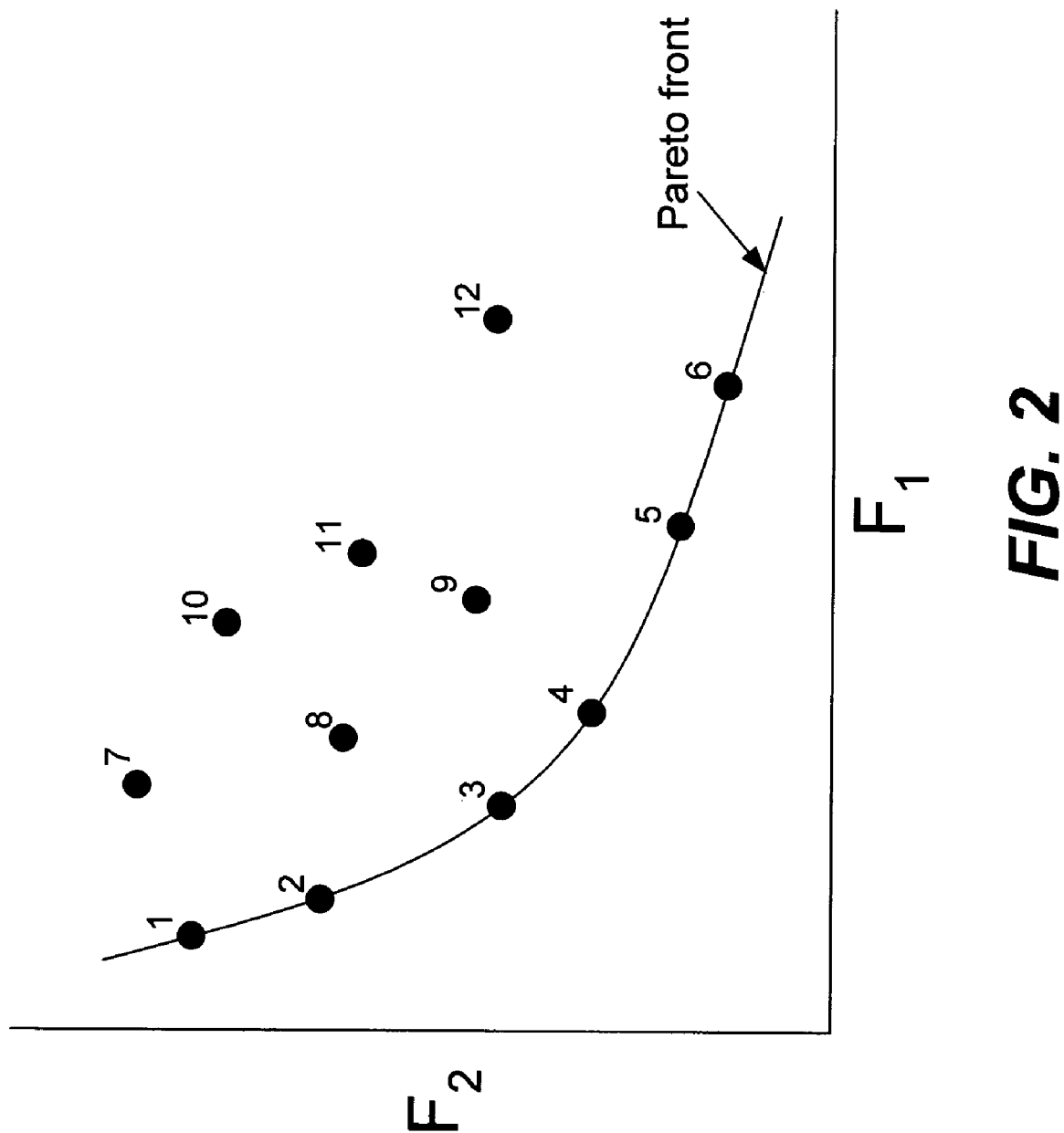
FIG. 2 is a graph that illustrates a convex Pareto front in a plot of a hypothetical set of data.

To illustrate, FIG. 2 provides a graph that illustrates a Pareto front in a plot of a hypothetical set of data, where function 2 (F2) is plotted as a function of function 1 (F1). Any optimization problem is optionally cast as a minimization problem, by, e.g., reversing the sign of the fitness or inverting the fitness. As shown in FIG. 2, for example, the axes represent different objectives to be simultaneously minimized. The solutions (represented by the numbered data points) that lie on the Pareto front represent trade-off solutions that are not "dominated" by any other solution. These non-dominated points are defined by the fact that no other solution exists in the hypothetical data set that is better (smaller in this case) than all solutions in both objectives. For example, solution 1 is part of the Pareto front because, even though solution 2 has a smaller value for objective F2, solution 1 has a smaller value for objective F1. In contrast, solution 7 is not part of the Pareto front because at least one solution is better in both objectives.

Figure 4:
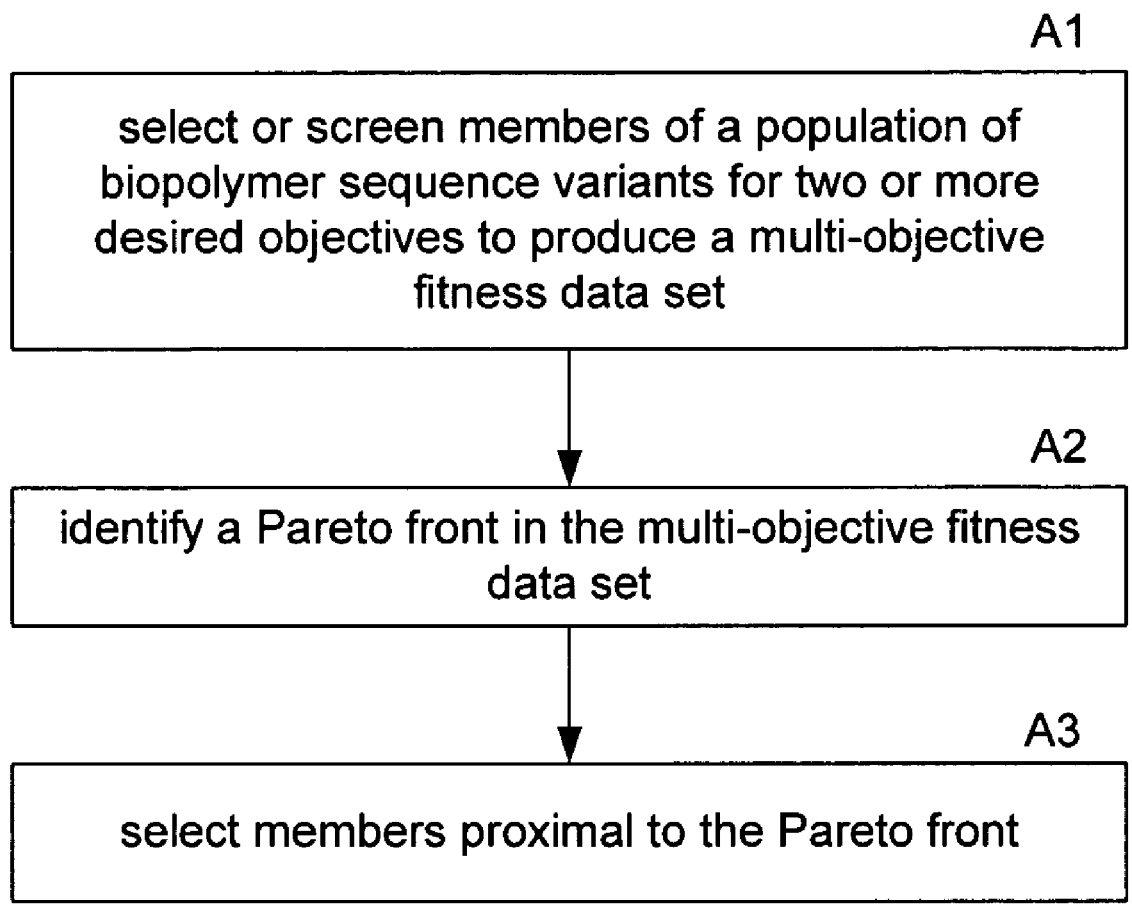
FIG. 4 is a chart that depicts certain steps performed in one embodiment of a method of identifying members of a population of biopolymer sequence variants most suitable for artificial evolution.

FIG. 4 is a chart that depicts certain steps performed in one embodiment of the invention method of identifying members of a population of biopolymer sequence variants most suitable for artificial evolution. The phrase "most suitable for artificial evolution" refers to those members of the variant population that lie at least proximal to a Pareto front, e.g., when the variants are scored (e.g., screened or selected) and plotted for desired objectives. These variants are generally the most suitable for artificial evolution, because they are not dominated by other variants (or at least most other variants) in at least one of the desired objectives.

As shown in A1 of FIG. 4, the method includes selecting or screening the members of the population of biopolymer sequence variants (e.g., character string variants, etc.) for two or more desired objectives to produce a multi-objective fitness data set. Desired objectives typically include, e.g., structural and/or functional properties, such as any of those described herein. The population of biopolymer sequence variants can be produced in accordance with the diversity generating procedures described herein, then screened for activities or other function (i.e., objectives). Thereafter, the method includes identifying a Pareto front (e.g., substantially convex, substantially non-convex, etc.) in the multi-objective fitness data set (A2), and selecting members proximal to the Pareto front (A3), thereby identifying the members of the population of biopolymer sequence variants most suitable for artificial evolution. In the context of the present invention, the "Pareto front" refers to biopolymer sequence variants that are non-dominated by other biopolymer sequence variants in at least one of two or more desired objectives. In some embodiments, the method further includes evolving the members selected in A3 using artificial evolution procedures to produce evolved biopolymer sequence variants. Various artificial evolution procedures that are optionally used to evolve these variants are described herein. At least one step, and in certain cases all steps, of these artificial evolution procedures may be performed in silico. These embodiments optionally also include repeating steps A1-A3 using the evolved biopolymer sequence variants as at least some of the members of the population of biopolymer sequence variants in a repeated step A1. Typically, at least one step, and some cases all steps, of the methods described herein are performed in a digital or web-based system. Digital and web-based systems are described in greater detail below.

In addition, to provide an optimal set of solutions from which to select, algorithms should generally attempt to evenly distribute or maximally spread the solutions in objective space along the Pareto front, because clustered solutions typically lack sufficient diversity. Accordingly, algorithms are typically designed to order individual solutions in a population based upon both fitness along each objective and according to their relative isolation in objective space. This approach generally results in a good spread of solutions along the Pareto front, even into non-convex regions of objective space. Non-convex Pareto fronts are discussed further below. One approach to selecting solutions based on their relative diversity is the technique of region-based selection, which is described further in, e.g., Come et al., "PESA-11: Region-based selection in evolutionary multiobjective optimization," in *Proceedings of the Genetic and Evolutionary Computation Conference (GECCO-2001)*, Morgan Kaufmann Publishers, (2001), pp. 283-290. Region-based selection generally involves partitioning the objective space into hyperboxes and preferentially selecting solutions from less populated hyperboxes. Other techniques for selecting solutions (e.g., binary tournament selection, etc.), which are generally known in the art are optionally utilized in practicing the methods described herein.

One significant advantage of Pareto front optimization is that the approach does not to reduce the problem at issue to one of single objective optimization (e.g., by a weighted sum approach or the like), rather the approach provides a set of optimal solutions from which to select. Although weighted measures are optionally used to select final solutions, not all solutions will be identified via this approach, e.g., if the Pareto front is non-convex. Accordingly, a simple weighted sum of objectives may restrict the ability of an algorithm to find viable solutions in these instances. The problem posed by non-convexity in the objective space is further illustrated in FIG. 3, which provides a graph that shows a plot of a hypothetical set of data. As shown and consistent with the definition, the set of solutions (represented by numbered data points) along the Pareto front are non-dominated. However, classical weight-based optimization, which is generally known in the art, would not yield solutions 3 and 4 for any weights on objectives F1 and F2, due to the existence of superior solutions based on the weighted sum. Furthermore, if an approximately equal trade-off for both objectives were sought, a whole class of solutions would be excluded using the classical methods.

Methods of the present invention include various embodiments for selecting sequence variants that are proximal to the Pareto front. For example, the methods optionally include applying one or more niching techniques to identify the members of the population of biopolymer sequence variants most suitable for artificial evolution. Additional details relating to various niching techniques are provided in, e.g., Darwen et al. (1997) "Speciation as automatic categorical modularization," *IEEE Transactions on Evolutionary Computation*, 1(2):101-108, Darwen et al. (1996), "Every niching method has its niche: fitness sharing and implicit sharing compared," Proc. of Parallel Problem Solving from Nature (PPSN) IV, Vol.1141, *Lecture Notes in Computer Science*, Springer-Verlag, (1996), pp.398-407, and Horn et al. (1994) "A niched pareto genetic algorithm for multiobjective optimization," In *Proceedings of the First IEEE Conference on Evolutionary Computation*, IEEE World Congress on Computational Computation, (1):82-87. In other embodiments, sequence variants are selected by, e.g., calculating a weighted sum of the two or more desired objectives for at least some of the members proximal to the Pareto front, and selecting at least one member that includes a higher weighted sum than other members proximal to the Pareto front. In still other embodiments, biopolymer sequence variants are selected by, e.g., ranking the one or more members according to relative proximity to the Pareto front and relative isolation in sequence space, and selecting at least one member that ranks higher than other members proximal to the Pareto front. Region-based selection techniques (described above) are also optionally used to select members proximal to the Pareto front. To illustrate, one region-based selection technique includes partitioning sequence space that includes the population of biopolymer sequence variants into one or more hyperboxes and selecting the members proximal to the Pareto front from at least one of the hyperboxes that is less populated than other regions of the sequence space.

Figure 3:
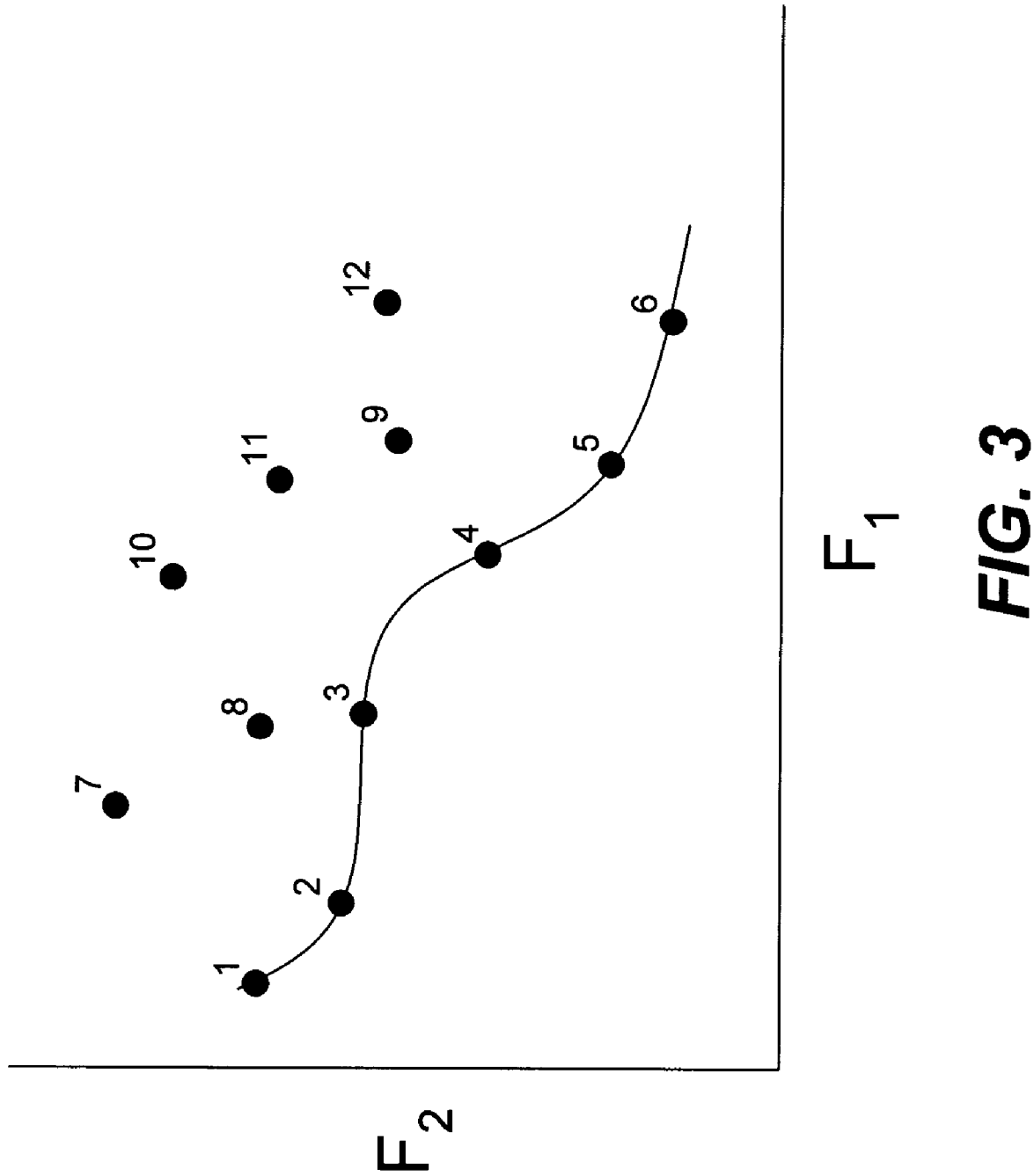
FIG. 3 is a graph that illustrates a non-convex Pareto front in a plot of a hypothetical set of data.
Figure 5:
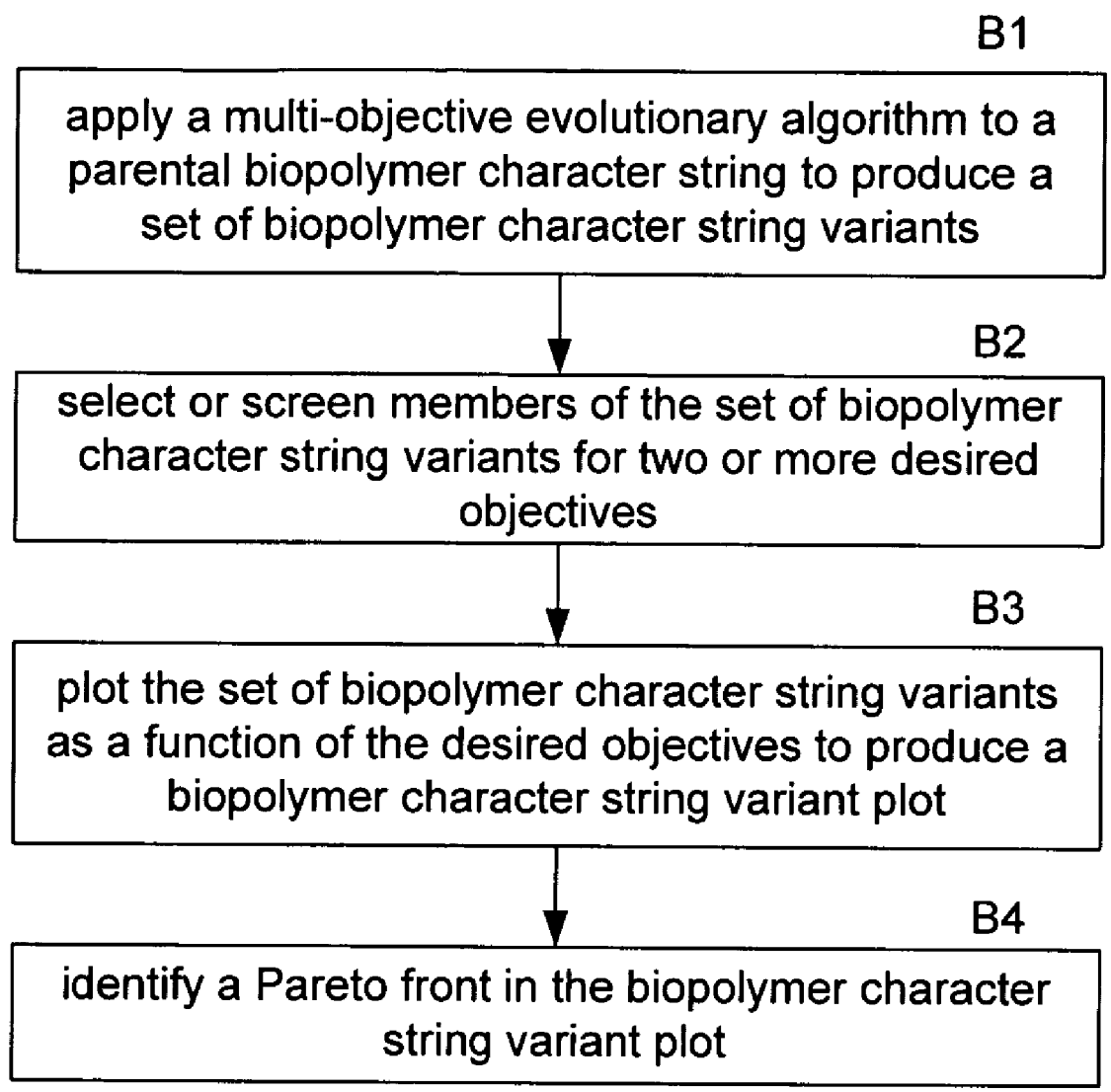
FIG. 5 is a chart that depicts certain steps performed in one embodiment of a method of identifying members of a set of biopolymer character string variants that include multiple improved objectives relative to other members of the set of biopolymer character string variants.

To further illustrate, FIG. 5 is a chart that depicts certain steps performed in one embodiment of a method of identifying members of a set of biopolymer character string variants that include multiple improved objectives relative to other members of the set of biopolymer character string variants. As shown, the method includes applying one or more multi-objective evolutionary algorithms to at least one parental biopolymer character string (e.g., a plurality of parental biopolymer character strings or the like) to produce the set of biopolymer character string variants (B1), and selecting or screening the members of the set of biopolymer character string variants for two or more desired objectives (B2). As further shown, the method also includes plotting the set of biopolymer character string variants as a function of the two or more desired objectives to produce a biopolymer character string variant plot (e.g., as depicted in FIG. 2 or 3)(B3), and identifying a Pareto front (e.g., substantially convex, substantially non-convex, etc.) in the biopolymer character string variant plot (B4), thereby identifying the members of the set of biopolymer character string variants that include the multiple improved objectives relative to the other members of the set of biopolymer character string variants. The method is optionally iteratively performed, e.g., repeating steps B1-B4 using at least one member of the set of biopolymer character string variants as a parental biopolymer character string in a repeated step B1. In some embodiments, the methods further include synthesizing polynucleotide or polypeptide sequence variants that correspond to members of the set of biopolymer character string variants identified in step B4.

In preferred embodiments, members proximal to the Pareto front in a given analysis are maximally spread apart (e.g., substantially evenly or uniformly distributed) from one another, e.g., to enhance diversity among identified solutions, as described above. In other embodiments, the sequence variants proximal to the Pareto front are substantially unevenly distributed (e.g., randomly or non-uniformly distributed). In addition, the biopolymer character string variant plots are optionally presented as, e.g., maximization or minimization plots.

Many different desired objectives are optionally screened or selected according to these methods. To illustrate, each of the two or more desired objectives typically independently include a physicochemical or functional property. In some embodiments, the two or more desired objectives include, e.g., constraints, values detailing distance from achieving constraints, a total number of constraints satisfied, and/or a relative number of constraints satisfied. Optionally, the two or more desired objectives include measures of fitness, competing or non-competing objectives, or the like. Furthermore, the two or more desired objectives are also optionally orthogonal to one another.

In other aspects, the invention provides systems for identifying members of a set of biopolymer character string variants that include multiple improved objectives relative to other members of the set of biopolymer character string variants. The systems include a computer having a database capable storing the set of biopolymer character string variants. The systems also include system software that includes logic instructions for applying multi-objective evolutionary algorithms to parental biopolymer character strings to produce the set of biopolymer character string variants, and selecting or screening the members of the set of biopolymer character string variants for two or more desired objectives. The system software also includes logic instructions for plotting the set of biopolymer character string variants as a function of the two or more desired objectives to produce a biopolymer character string variant plot, and identifying a Pareto front in the biopolymer character string variant plot. Systems are described in greater detail below.

The invention also provides a computer program product that includes a computer readable medium having logic instructions for applying multi-objective evolutionary algorithms to parental biopolymer character strings to produce a set of biopolymer character string variants, and selecting or screening the members of the set of biopolymer character string variants for two or more desired objectives. In addition, the computer program product includes logic instructions for plotting the set of biopolymer character string variants as a function of the two or more desired objectives to produce a biopolymer character string variant plot, and identifying a Pareto front in the biopolymer character string variant plot to identify the members of the set of biopolymer character string variants that include multiple improved objectives relative to other members of the set of biopolymer character string variants.

To assist in selecting clones from a given experiment to further develop, e.g., via the artificial evolution procedures described herein, systems and computer program products of the invention generally include logic instructions that rank clones in terms of, e.g., their proximity to the Pareto front, by their relative isolation, and/or the like. This provides for extensive diversity along the Pareto front with the concomitant benefits of such diversity, as described above. Further, the best clones along the most advanced Pareto front are optionally selected at sampling rates (e.g., DNA concentrations, etc.) based on their modified fitness values. This allows clones from less populated areas of objective space to be sampled more often, which again promotes diversity in subsequent rounds of artificial evolution. A weighted sum of the activities after evolution is optionally used to select the "best" clone. However, researchers have found that using a weighted sum of the activities during evolution results in a single objective optimization with low diversity along the Pareto front.

In addition, niching techniques (mentioned above) are optionally applied to select clones for development. For example, in multi-modal single-objective optimization, research has shown that niching can be beneficial under certain circumstances. The idea is simply to artificially evolve those individuals in the population that are similar genotypically and which occupy high fitness areas. The reasoning is that motifs brought together from different modes in fitness space may not lead to better function. Indeed, they often lead to noise and disruption. In the context of multi-objective optimizations, a simplified toy problem may be simulated (e.g., using Kauftnann's NK model, etc.) to determine whether niching assists or hinders evolution along the Pareto front. See, e.g., Kauffman, *The Origins of Order*, Oxford University Press (1993) and Kauftnann and Johnsen, "Co-Evolution to the Edge of Chaos: Coupled Fitness Landscapes, Poised States, and Co-Evolutionary Avalanches," in Langton et al., *Artificial Life II: Proceedings of the Second Artificial Life Workshop*, Addison-Wesley (1992), pp. 325-369. In particular, it may depend on the relative ruggedness of each objective's fitness space. For example, motifs that confer, e.g., thermostability may be additive, while motifs that confer, e.g., activity under different pH conditions may be competitive and attempts to make large jumps in multi-objective fitness space may lead to high dead rates.

B. In Silico Evolution

The present invention includes methods of optimizing library construction via in silico evolution of libraries using evolutionary search algorithms, including genetic algorithms and Monte Carlo methods, which are described herein. These methods maximize the successful in vivo and/or in vitro evolution of essentially any genetic material, including genes, operons, pathways, promoters, regulatory elements, genomes, or the like.

Figure 6:
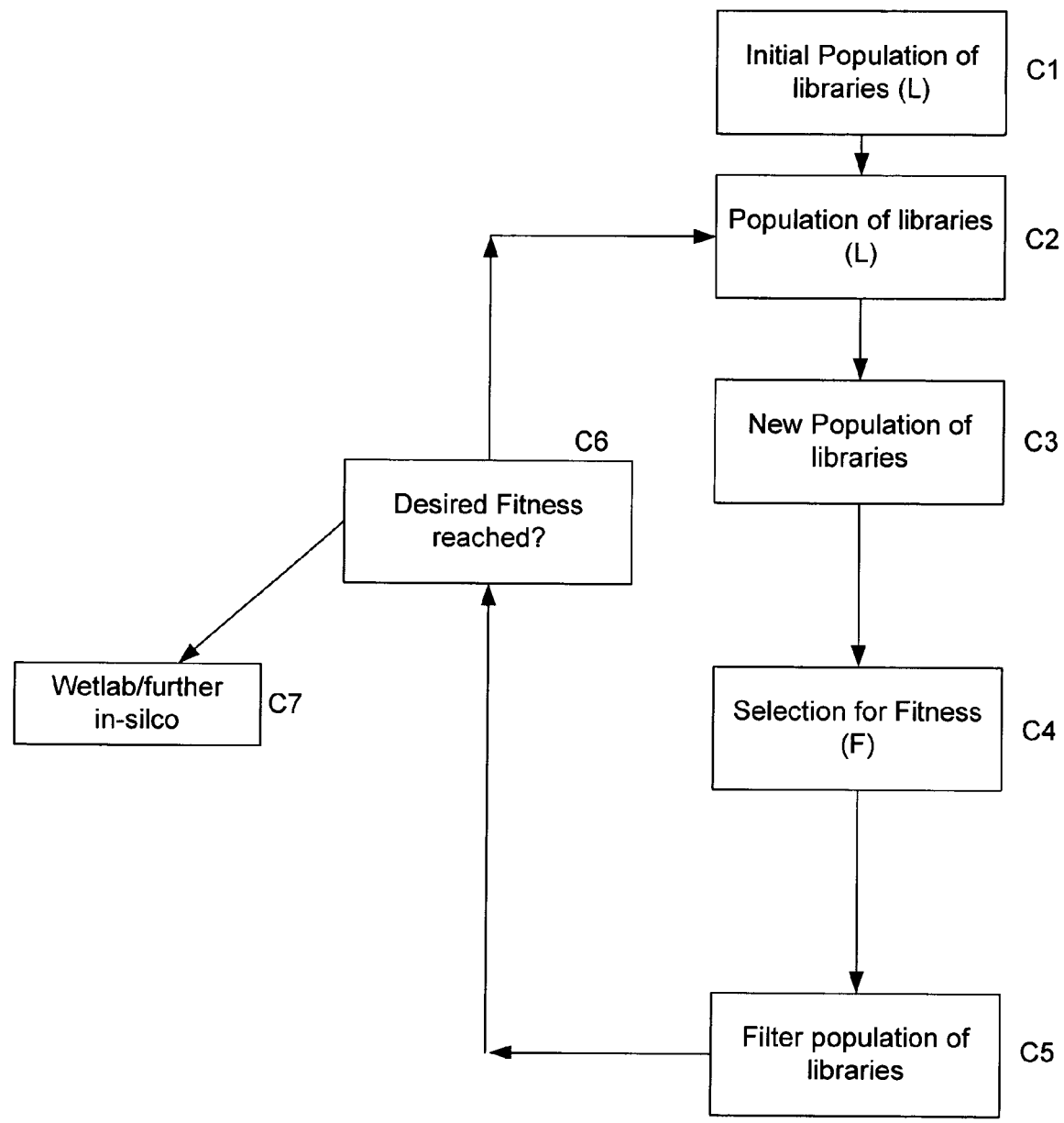
FIG. 6 is a chart that depicts steps performed in one embodiment of a method of evolving libraries for directed evolution.

More specifically, FIG. 6 provides a chart depicting certain steps performed in a method embodiment for evolving libraries for directed evolution in which the library (L) is the unit of evolution in the algorithm. Each library is described by parameters such as sequence diversity, recombination method, experimental conditions, and/or the like. Additional parameters are described herein. The parameters are typically changed or otherwise evolve during the evolution process. As shown in C2, the methods include providing a population of libraries (e.g., an initial population of libraries (C1)), such as populations of biopolymer character string variants. The algorithm includes a set of operators (O) that operates on the unit L to produce a new population of libraries (C3). For example, the operations include adding and deleting diversity, changing recombination rates and frequencies, and/or the like. Additional details regarding operators that are optionally used in these methods are provided herein. In particular, the operator acts on a population of libraries to create the next generation of the population. As shown in C4, this next generation is then selected for fitness (F) to produce a fitter population of libraries (C5) and this process is iterated (C6). This evolutionary algorithm is typically stopped when desired characteristics (e.g., levels of fitness) for the libraries are met. Optionally, the selection process involves designing oligonucleotides using algorithms for facilitating the identification of data sequences corresponding to biological polymers and enumerating/simulating the outcome of an experiment followed by in silico estimation of the activities of the clones. Each library is then typically characterized by a fitness function that involves determining, e.g., mean activity of the clones, standard deviation of the activities of the clones, genetic diversity among clones, experimental simplicity of the library, etc. The activities of the clones can also be characterized by neural networks, PCA or other prediction tools or by structural compatibility, dynamics simulation and other biophysical methods and/or by other techniques described herein.

Figure 7:
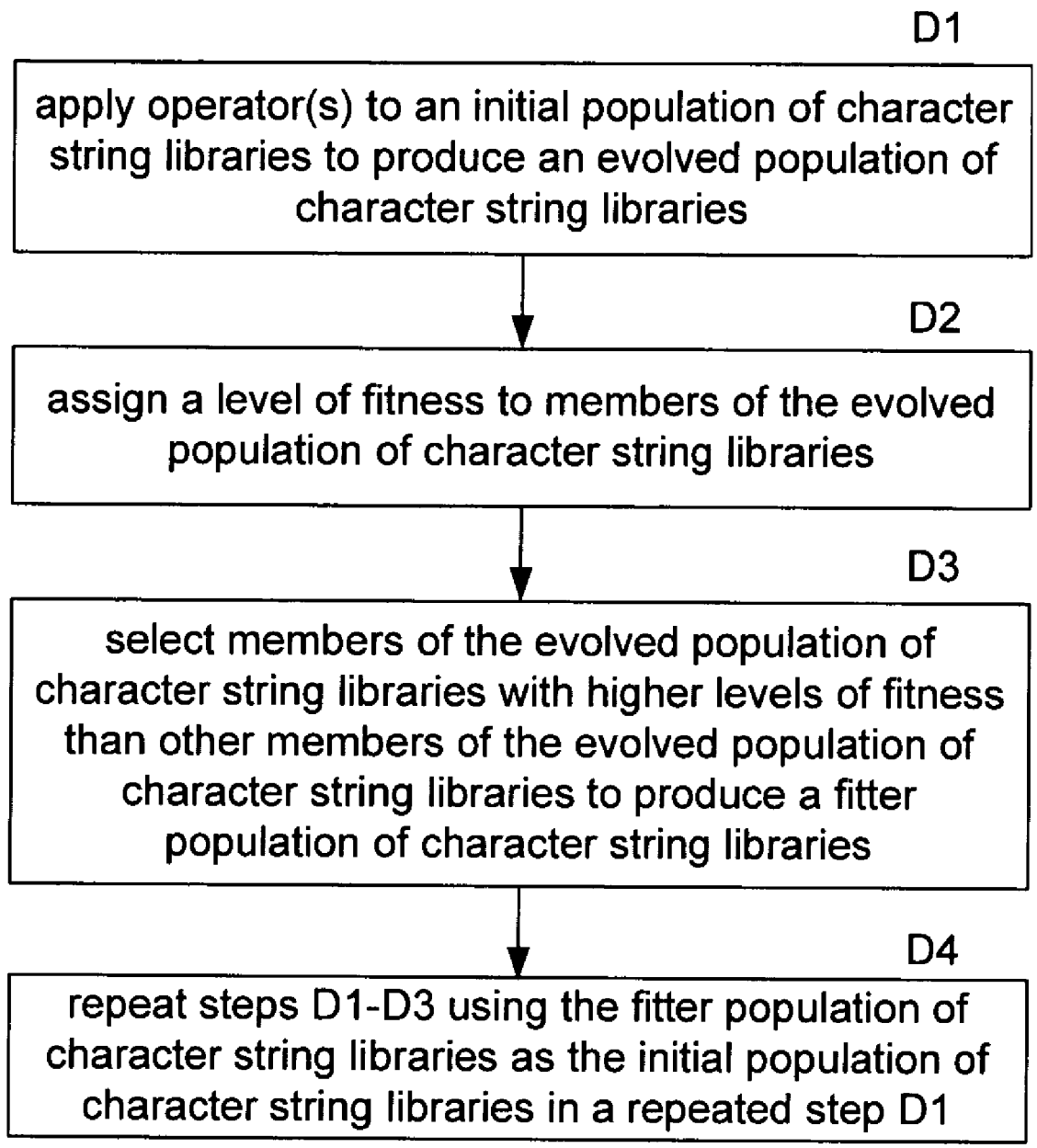
FIG. 7 is a chart that depicts certain steps performed in an embodiment of a method of producing a fitter population of character string libraries.

To further illustrate these aspects of the invention, FIG. 7 provides a chart that shows certain steps performed in an embodiment of a method of producing a fitter population of character string libraries that utilizes various operators. At least one step, and in certain cases all steps, of the method is/are typically performed in silico, e.g., in a digital system described herein. As shown, step D1 includes applying one or more operators to an initial population of character string libraries to produce an evolved population of character string libraries. Typically, one or more character strings in the initial population of character string libraries correspond to one or more polynucleotides or one or more polypeptides. After assigning a level of fitness (e.g., screening or selecting for, e.g., desired structural properties, desired functional properties, and/or the like) to members of the evolved population of character string libraries (D2), the method includes selecting members of the evolved population of character string libraries with higher levels of fitness than other members of the population to produce a fitter population of character string libraries (D3). The method further includes repeating steps D1-D3 using the fitter population of character string libraries as the initial population of character string libraries in a repeated step D1, e.g., until a desired level of fitness is reached in at least one character string library.

In certain embodiments, step D1 includes (i) providing sets of degenerate substrings based upon the initial population of character string libraries members, (ii) recombining the sets of degenerate substrings to produce desired systematically varied character strings, and (iii) estimating one or more activities of the desired systematically varied character strings to produce the evolved population of character string libraries. In some embodiments, one or more members of the initial population of character string libraries are defined by an algorithm that takes one or more parameters, which parameters evolve during step D1. Exemplary parameters include, e.g., character string diversity, modeled evolution method utilized, modeled experimental conditions utilized, PCA modeling, PLS modeling, mutation matrices, relative importance of, e.g., individual character strings or libraries, scoring systems for some or all parameters utilized, and/or the like. The initial population of character string libraries generally includes between about two and about $10^5$ libraries. In addition, each character string library of the initial population of character string libraries typically includes between about two and about $10^5$ members.

Many different operators are optionally used in practicing these methods. These include, e.g., a mutation of one or more members of the character string libraries, a multiplication of one or more members of the character string libraries, a fragmentation of one or more members of the character string libraries, a crossover between members of the character string libraries, a ligation of one or more members of the character string libraries or substrings of the one or more members of the character string libraries, an elitism calculation, a calculation of sequence homology or sequence similarity of aligned character strings, a recursive use of one or more genetic operators for evolution of one or more members of the character string libraries, an application of a randomness operator to one or more members of the character string libraries, a deletion mutation of one or more members of the character string libraries, an insertion mutation into one or more members of the character string libraries, subtraction of one or more members of the character string libraries, selection of one or more members of the character string libraries with desired activities, death of one or more members of the character string libraries, or the like. See e.g., WO 00/42560; WO 01/75767. The operators are generally included as components of evolutionary search algorithms. Preferred evolutionary search algorithms include genetic algorithms, Monte Carlo algorithms, and/or the like, which are also described further herein.

Levels of fitness are typically assigned to each member of the evolved population of character string libraries using fitness functions. Exemplary fitness functions optionally include, e.g., determining mean activities of members of each character string library, determining standard deviations of activities of members of each character string library, determining levels of character string diversity among members of each character string library, modeling an experimental simplicity of each character string library, determining a level of confidence in measured or predicted values, and/or the like. In preferred embodiments, the activities of the members are determined using multivariate analysis techniques and/or biophysical analysis techniques. For example, multivariate analysis techniques optionally include, e.g., neural network training techniques, principal components analyses, partial least squares analyses, and/or the like. Typical biophysical analysis techniques include one or more of, e.g., structural compatibility analyses, dynamics simulations, hydrophobicity analyses, solubility analyses, immunogenicity analyses, binding assays, enzymatic characterizations, or the like. Multivariate analysis and biophysical analyses are described further herein.

Members of the fitter population of character string libraries generally correspond to polynucleotides or polypeptides. Although the steps of these methods are typically performed in silico (e.g., using a digital system, a web-based system, etc.), the methods optionally further include synthesizing, e.g., one or more of the polynucleotides or polypeptides corresponding to one or more members of the fitter population of character string libraries to produce synthesized polynucleotides or polypeptides. In addition, the methods also optionally include, e.g., selecting or screening the synthesized polynucleotides or polypeptides for at least one desired property to produce screened or selected polynucleotides or polypeptides. Typically, the synthesized polynucleotides or polypeptides are screened in vitro or in vivo. Various screening techniques used in practicing these methods are described herein. The methods optionally further include subjecting the screened or selected polynucleotides or polypeptides to one or more artificial evolution procedures. At least one step of the one or more artificial evolution procedures is optionally performed in silico, e.g., using character string representations of the polynucleotides or polypeptides.

In another aspect, the invention relates to a system for producing a fitter population of character string libraries. The system includes (a) at least one computer that includes a database capable of storing at least one population of character string libraries, and (b) system software including one or more logic instructions. The logic instructions are typically for, e.g., (i) applying one or more operators to an initial population of character string libraries to produce an evolved population of character string libraries, (ii) assigning a level of fitness to at least one member of the evolved population of character string libraries, (iii) selecting one or more members of the evolved population of character string libraries with higher levels of fitness than other members of the evolved population of character string libraries to produce the fitter population of character string libraries, and (iv) repeating steps (i)-(iii) using the fitter population of character string libraries as the initial population of character string libraries in a repeated step (i). The system typically further includes a polynucleotide or a polypeptide synthesis device capable of synthesizing polynucleotides or polypeptides that correspond to members of the fitter population of character string libraries. Systems are described in greater detail below.

The invention also provides a computer program product that includes a computer readable medium having one or more logic instructions for (a) applying one or more operators to an initial population of character string libraries to produce an evolved population of character string libraries, and (b) assigning a level of fitness to at least one member of the evolved population of character string libraries. The computer program product also include logic instructions for (c) selecting one or more members of the evolved population of character string libraries with higher levels of fitness than other members of the evolved population of character string libraries to produce the fitter population of character string libraries, and (d) repeating steps (a)-(c) using the fitter population of character string libraries as the initial population of character string libraries in a repeated step (a).

C. Making Libraries from Heuristically-Derived Models

The following discussion supplements the above described aspect of the invention presented in FIG. 1A. It also presents some alternative embodiments and elaborates on some previously introduced concepts. It does not limit the above discussion.

As described herein, having access to data sets of systematically varied sequences with measured activities enables the generation of various models. This description illustrates how to implement these models in the construction of preferred libraries. Although other modeling techniques, many of which are described herein, are optionally also used to construct/score libraries, PLS models are emphasized in this section for purposes of clarity. In particular, one alternative to decide on the sequence space to search involves isolating the loads (e.g., relationships to function) for each amino acid residue in a given alignment. For example, loads are typically found stored as a matrix in the model generated by, e.g., any standard PLS modeling tool and can be retrieved, e.g., from a File_Name.loads matrix.

In overview, the importance for each residue and best, for example, 5% of residue pairs (defined as cross products in the matrix) is optionally determined using PLS or the like, and the relative importance is given as load (if one component is used), regression coefficient, VIP (variable importance for projection), etc. Optionally, loads are subsequently sorted, e.g., according to numerical value. The preferred amino acid in each position in the particular protein having two or more optional amino acids will be determined by the corresponding amino acid having the highest load, regression coefficient, VIP, etc. A "hero" clone having the theoretically best sequence (i.e., encodes the amino acid option having the highest load in each position) is thus determined. Further, for models generating more than one latent variable, regression coefficients or similar parameters can also be used.

As explained, these approaches may initially include identifying the wet-lab validated "best" clone in a particular data set, which is typically the clone with the highest measured function that still models well (i.e., falls relatively close to the predicted value in PLS cross validation). Each residue in the best clone is typically compared with those from the loads matrix, e.g., starting with the residue having the highest load. If the residue with the highest load is not present in the "best" clone, that position is introduced as a toggle in the subsequent library. In some embodiments, the residues to toggle are determined by sorting each residue by increasing VIP and omitting those that are well characterized in the model (i.e., exist in the data set as many instances and are systematically varied). This can most easily be done by retaining only those that occur as single (and double if the data set is large enough) instances. A library of two would thus encode the "hero" clone and toggle of the residue having VIP closest to zero and only present in a single instance in the data set. A library of 4 ($2^2$) would toggle the two lowest VIP residues with single instances, etc. These processes are repeated until the library reaches a selected or sufficient size. Each added diversity represented by a toggle, doubles the size of the library such that 10 positions equal approximately 1,000 clones (1,024), 13 positions equal approximately 10,000 clones (8,192), 20 positions equal approximately 1,000,000 clones (1,048,576), etc. The appropriate library size depends on factors such as cost of screen, ruggedness of landscape, preferred percentage sampling of space, and the like. Optionally, residues having small loads are toggled, e.g., to search the local space surrounding an already validated "best" clone. An additional option includes starting with an average clone that models well and toggling the high loads, e.g., to explore larger space in search for activity hills previously omitted from the sampling. This type of library is generally more relevant at the early rounds, because it generates a more refined picture for subsequent rounds. As an additional filter, one can omit residues that are originally derived from non-natural diversity. The rationale being that naturally existing diversity has a higher probability of encoding functionality than does randomly occurring diversity, which may or may not be true.

Figure 8:
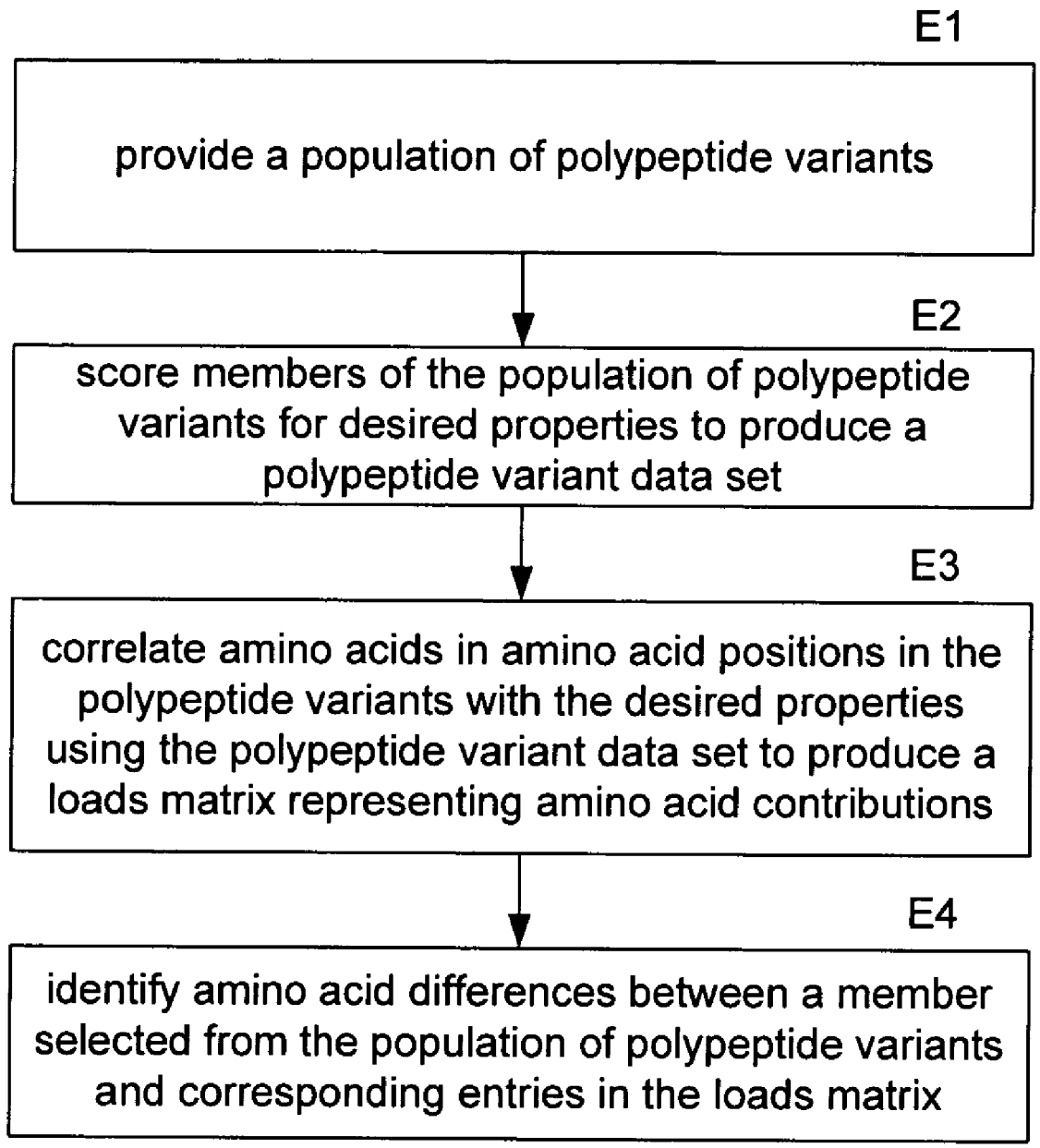
FIG. 8 is a chart that shows certain steps performed in an embodiment of a method of selecting amino acid positions in a polypeptide variant to artificially evolve.

To further illustrate, FIG. 8 is a chart that shows certain steps performed in an embodiment of a method of selecting amino acid positions in a polypeptide variant to artificially evolve, which steps are typically performed in a digital or web-based system. As shown, the methods include providing a population of polypeptide variants (E1) and scoring (e.g., in silico) members of the population of polypeptide variants (e.g., character string variants, etc.) for one or more desired properties (e.g., structural and/or functional properties) to produce a polypeptide variant data set (E2). The population of polypeptide variants is generally provided by one or more artificial evolution procedures. In addition, at least one step (and often more) of the artificial evolution procedures is typically performed in silico. Populations of polypeptide variants typically include, e.g., between about two and about $10^6$ members. In preferred embodiments, members of the population of polypeptide variants are systematically varied sequences.

The methods further include correlating amino acids in amino acid positions in the polypeptide variants with the one or more desired properties using the polypeptide variant data set to produce a loads matrix (e.g., a qualitative matrix (e.g., including amino acid identities, etc.), a quantitative matrix (e.g., including physicochemical properties, such as hydrophobicity measures, etc.), a categorical matrix (e.g., whether amino acids are charged, bulky, etc.), and/or the like), e.g., representing amino acid contributions to the desired properties (E3). For example, if two polypeptide sequences are identical except for a single amino acid residue, and the sequences have different activities, then all difference in function is typically assumed to correlated only with that amino acid difference. Accordingly, essentially any way that the relative importance for a given variable towards a functional parameter Y can be scored is optionally used in these methods. To illustrate, the matrix is optionally based on regression-based algorithms, e.g., PLS, regression coefficients, VIP (Variable Importance for Projection)(one preferred algorithm), MLR (multiple linear regression), ILS (inverse least square), PCR (principal component regression), and/or the like. Additional alternatives include basing the loads matrix on pattern-based algorithms, such as neural networks, CART (classification and regression trees), MARS (multivariate adaptive regression splines), and/or the like. The methods also typically include sorting entries in the loads matrix, e.g., according to numerical value, etc.

As shown in step E4, the methods also include identifying one or more amino acid differences between at least one member selected from the population of polypeptide variants and corresponding entries in the loads matrix, thereby selecting the amino acid positions in the polypeptide variant to artificially evolve (e.g., toggle with variable amino acid residues). For example, the preferred solution is to pick a member that is "best" or highest scoring in the preferred function or set of functions (e.g., as long as it fits the model reasonably well) and pick residues to evolve on that member. Typically, between about two and about 100 amino acid positions in the polypeptide variant are selected to artificially evolve. Optionally, all amino acid positions in a given variant are selected. In certain embodiments, the at least one member selected from the population of polypeptide variants in E4 includes a highest scoring member from E2. The methods typically further include artificially evolving one or more of the amino acid positions selected in E4 to produce an evolved polypeptide library. In addition, the methods optionally also include repeating E1-E4 using the evolved polypeptide library as the population of polypeptide variants in a repeated E1. Evolved polypeptide libraries optionally include physical or computational libraries. Physical libraries typically include, e.g., between about two and about $10^6$ members. In contrast, computational libraries typically include, e.g., between about two and about $10^{20}$ members.

As referred to above, in preferred embodiments, loads matrices are generated from polypeptide variant data sets using various heuristically-derived modeling techniques, including regression-based algorithms, pattern-based algorithms, and/or the like. Exemplary regression-based algorithms include, e.g., partial least squares regression, multiple linear regression, inverse least squares regression, principal component regression, variable importance for projection, etc. Exemplary pattern-based algorithms include, e.g., neural networks, classification and regression trees, multivariate adaptive regression splines, and/or the like. In certain preferred embodiments, E3 includes generating a partial least squares model from the polypeptide variant data set to produce the loads matrix. The partial least squares model typically generates more than one latent variable. The methods also typically further include using regression coefficients.

In preferred embodiments, step E4 includes comparing one or more amino acid positions in the at least one member with one or more corresponding amino acid positions from the loads matrix to identify at least one amino acid in the loads matrix that is absent in the member to select the amino acid positions in the polypeptide variant to artificially evolve. Generally, each amino acid position in the at least one member is compared with each corresponding amino acid position from the loads matrix. Selected amino acid positions are optionally artificially evolved by substituting one or more corresponding amino acids from the loads matrix. In addition, the member selected from the population of polypeptide variants typically includes a higher scoring member (e.g., the highest scoring member) of the polypeptide variant data set than other members of the polypeptide variant data set. For example, the higher scoring member is typically proximal to a predicted score in a partial least squares cross validation. The amino acid positions from the loads matrix that include higher loads are typically compared prior to the amino acid positions from the loads matrix that include lower loads. Optionally, the amino acid positions from the loads matrix that include lower loads are compared prior to the amino acid positions from the loads matrix that include higher loads. In some embodiments, the member selected from the population of polypeptide variants includes a substantially average scoring member of the polypeptide variant data set. In these embodiments, the amino acid positions from the loads matrix that include higher loads are typically compared prior to the amino acid positions from the loads matrix that include lower loads.

Figure 9:
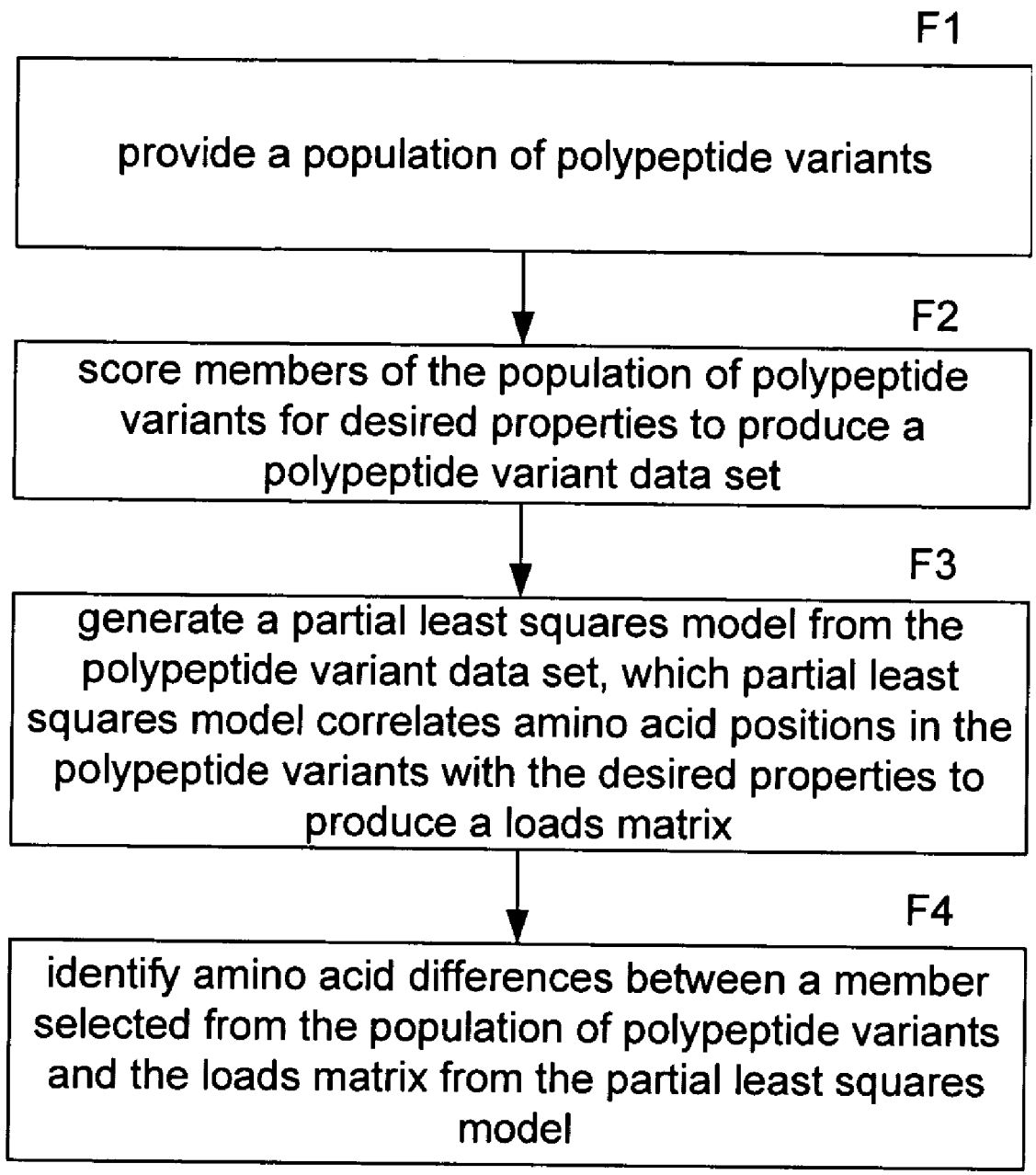
FIG. 9 is a chart that shows certain steps performed in another embodiment of a method of selecting amino acid positions in a polypeptide variant to artificially evolve.

FIG. 9 is a chart that shows certain steps performed in another embodiment of these methods of selecting amino acid positions in a polypeptide variant to artificially evolve. As shown, the method includes providing a population of polypeptide variants (F1), and scoring members of the population of polypeptide variants for one or more desired properties to produce a polypeptide variant data set (F2). In step F3, a partial least squares model is generated from the polypeptide variant data set, which partial least squares model correlates amino acid positions in the polypeptide variants with the one or more desired properties to produce a loads matrix. The methods also include identifying one or more amino acid differences between at least one member selected from the population of polypeptide variants and the loads matrix from the partial least squares model, thereby selecting amino acid positions in the polypeptide variant to artificially evolve (F4).

The invention also provides a system for selecting amino acid positions in a polypeptide character string variant to artificially evolve. The system includes (a) a computer that includes a database capable of storing at least one population of polypeptide character string variants, and (b) system software. The system software includes one or more logic instructions for (i) providing one or more populations of polypeptide character string variants, and (ii) scoring members of the one or more populations of polypeptide character string variants for one or more desired properties to produce a polypeptide character string variant data set. The software also includes instructions for (iii) correlating amino acids in amino acid positions in the polypeptide character string variants with the one or more desired properties using the polypeptide character string variant data set to produce a loads matrix representing amino acid contributions to the one or more desired properties, and (iv) identifying one or more amino acid differences between at least one member selected from the one or more populations of polypeptide character string variants and corresponding entries in the loads matrix. Additional details relating to various aspects of the systems of the present invention are provided below.

In addition, the invention relates to a computer program product for selecting amino acid positions in a polypeptide character string variant to artificially evolve. The computer program product includes a computer readable medium having one or more logic instructions for (a) providing one or more populations of polypeptide character string variants, and (b) scoring members of the one or more populations of polypeptide character string variants for one or more desired properties to produce a polypeptide character string variant data set. The program also includes instructions for (c) correlating amino acids in the amino acid positions in the polypeptide character string variants with the one or more desired properties using the polypeptide character string variant data set to produce a loads matrix representing amino acid contributions to the one or more desired properties, and (d) identifying one or more amino acid differences between at least one member selected from the one or more populations of polypeptide character string variants and corresponding entries in the loads matrix.

D. Using Cross Products in Heuristically-Derived Models for Sequence Space Exploration Interactions (e.g., second order, third order, etc.) among amino acid residues are important for protein sequence-activity (function) relationships (PSAR (PSFR)). Another aspect of the invention involves calculating cross product terms, i.e., co-varying residues, among various columns corresponding to amino acid residue positions in a matrix. A detailed description of covariation phenomena is provided in the Examples below. The cross product terms are then typically added to the linear terms, which correspond to amino acid residues, and an expanded X predictor matrix is generated. Heuristically-derived models are generated with the expanded predictor matrix to identify important cross terms along with linear terms. This cross product and linear term information is then typically utilized in the construction of subsequent libraries. For example, two amino acid residues alone may not be important, e.g., as manifested by weights of linear terms in PLS or PCR modeling, but their cross product term may be important. Accordingly, the corresponding amino acid positions may be good candidates for exploration in subsequent rounds of artificial evolution to ensure optimal sequence space searching.

Figure 10:
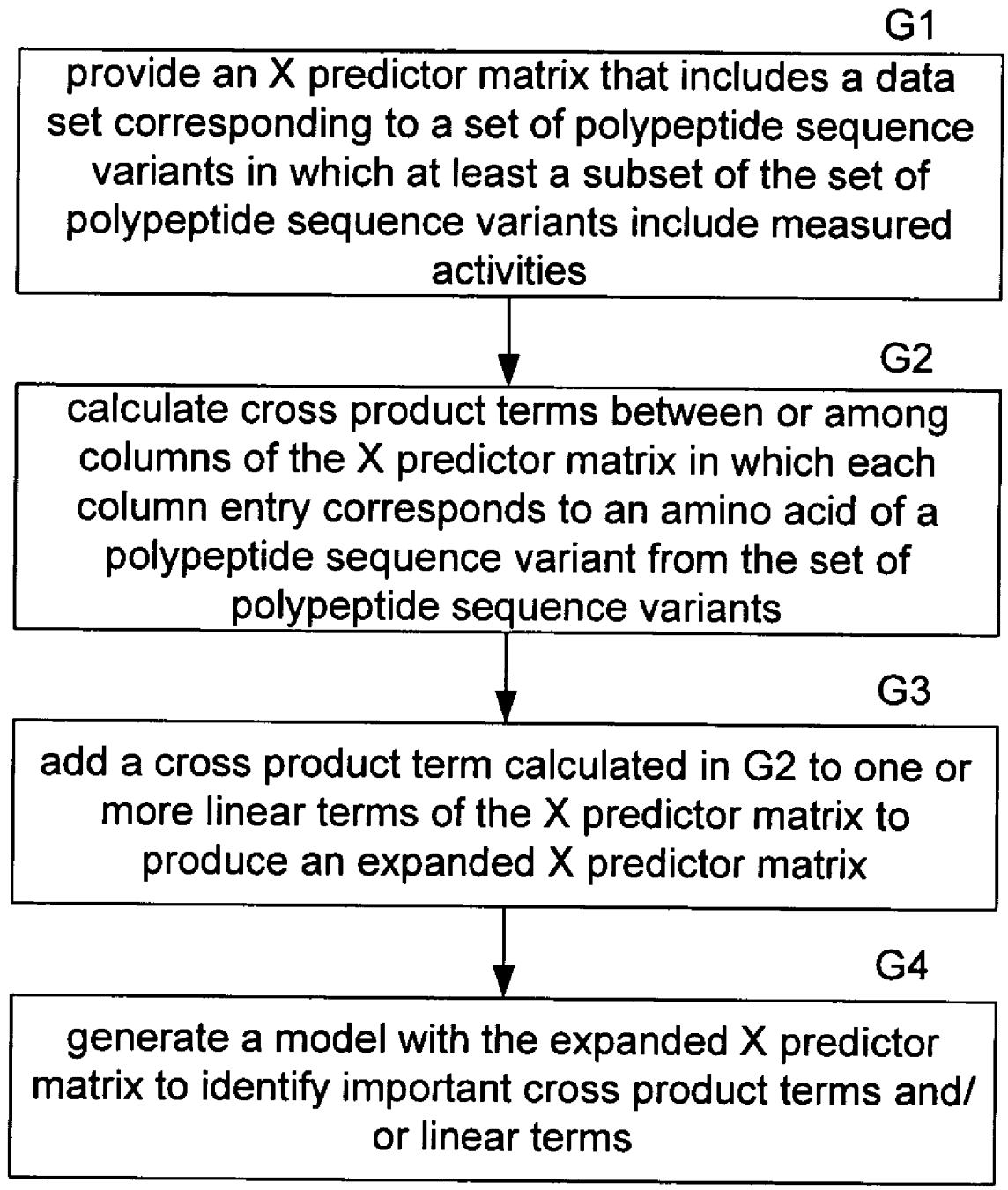
FIG. 10 is a chart that shows certain steps performed in an embodiment of a method of identifying amino acids in polypeptides that are important for a polypeptide sequence-activity relationship.

To further illustrate, FIG. 10 is a chart that shows certain steps performed in an embodiment of a method of identifying amino acids in polypeptides that are important for a polypeptide sequence-activity relationship. As shown in G1, the methods include providing an X predictor matrix that includes a data set corresponding to a set of polypeptide sequence variants in which at least a subset of the set of polypeptide sequence variants include one or more measured activities. The set of polypeptide sequence variants typically includes, e.g., a set of systematically varied polypeptide sequences or the like, e.g., produced by one or more diversity generating or artificial evolution procedures, such as any of those described herein. As further shown in G2, the methods also include calculating one or more cross product terms between or among columns of the X predictor matrix. Each column entry corresponds to an amino acid of a polypeptide sequence variant from the set of polypeptide sequence variants. In addition, the methods also include adding at least one of the one or more cross product terms calculated in step G2 to one or more linear terms of the X predictor matrix to produce an expanded X predictor matrix (G3). Cross product terms identify covarying amino acids in the polypeptides, whereas the linear terms correspond to amino acids in the polypeptide sequence variants. Thereafter, the methods include generating a model with the expanded X predictor matrix to identify important cross product terms and/or linear terms, thereby identifying the amino acids in the polypeptides that are important for the polypeptide sequence-activity relationship (G4).

Optionally, the heuristically-derived models are produced using one or more regression-based algorithms selected from, e.g., a partial least squares regression, a multiple linear regression, an inverse least squares regression, a principal component regression, a variable importance for projection, or the like. As an additional option, the model is produced using one or more pattern-based algorithm selected from, e.g., a neural network, a classification and regression tree, a multivariate adaptive regression spline, or the like.

Typically, the important cross product terms and/or linear terms identified in G4 are used to design one or more polypeptide libraries. As mentioned, in certain aspects, two or more linear terms individually may include unimportant terms for the polypeptide sequence-activity relationship. However, cross product terms calculated from the same two or more linear terms may be identified as important for the polypeptide sequence-activity relationship. Cross product terms typically correspond to interactions between or among amino acids in the polypeptide sequence variants. For example, the interactions include, e.g., secondary or tertiary interactions, direct interactions, indirect interactions, physicochemical interactions, interactions due to folding intermediates, translational effects, and/or the like. Sequence-activity information derived from covariation analysis (i.e., cross product terms) can be used in a method for characterizing the covariation in a polypeptide library by:

(a) identifying varying amino acid residues in a character string population that represents a population of homologous parental polypeptides;

(b) identifying amino acid residues in the character string population that covary with one another to produce a parental covariation data set;

(c) providing a set of overlapping synthetic oligonucleotides comprising members that encode one or more covarying amino acid residues identified in the character string population, wherein each synthetic oligonucleotides encodes at most one member of a set of amino acid residues that covary with each other;

(d) recombining the overlapping synthetic oligonucleotides to produce a set of recombined polynucleotides that encode progeny of the homologous parental polypeptides, (e) expressing at least a subset of the set of recombined polynucleotides to produce a set of progeny polypeptides;

(f) selecting or screening at least a subset of the progeny polypeptides for a desired property;

(g) sequencing one or more progeny polypeptides, or one or more recombined polynucleotides that encode the one or more progeny polypeptides, that comprise the desired property to produce a progeny sequence data set;

(h) identifying one or more pairs of amino acid residues in the progeny sequence data set that covary with one another to produce a progeny covariation data set; and (i) identifying differences between the parental and progeny covariation data sets, thereby characterizing the covariation in the population of homologous polypeptides.

These aspects of the invention are also embodied in a system for identifying amino acids in polypeptides that are important for a polypeptide sequence-activity relationship. The system includes (a) a computer that includes a database capable of storing at least one population of character string libraries, and (b) system software. The system software includes one or more logic instructions for (i) providing an X predictor matrix that includes a data set corresponding to a set of polypeptide sequence variants in which at least a subset of the set of polypeptide sequence variants include one or more measured activities, and (ii) calculating one or more cross product terms between or among columns of the X predictor matrix in which each column entry corresponds to an amino acid of a polypeptide sequence variant from the set of polypeptide sequence variants. The software also includes instructions for (iii) adding at least one of the one or more cross product terms calculated in step (ii) to one or more linear terms of the X predictor matrix to produce an expanded X predictor matrix, and (iv) generating a model with the expanded X predictor matrix to identify important cross product terms and/or linear terms. Additional details regarding the systems of the invention are described below.

The invention also provides a computer program product for identifying amino acids in polypeptides that are important for a polypeptide sequence-activity relationship. The computer program product includes a computer-readable medium having one or more logic instructions for (a) providing an X predictor matrix that includes a data set corresponding to a set of polypeptide sequence variants in which at least a subset of the set of polypeptide sequence variants include one or more measured activities, and (b) calculating one or more cross product terms between or among columns of the X predictor matrix in which each column entry corresponds to an amino acid of a polypeptide sequence variant from the set of polypeptide sequence variants. The program also includes instructions for (c) adding at least one of the one or more cross product terms calculated in (b) to one or more linear terms of the X predictor matrix to produce an expanded X predictor matrix, and (d) generating a model with the expanded X predictor matrix to identify important cross product terms and/or linear terms.

E. Protein Variant Library Design Incorporating Evolutionary Information

While it may be desirable to vary amino acid residues in a large number of positions in a single protein variant library, doing so may lead to a library with a large number of variants having little or no activity due to deleterious combinations of too many variable residues. The present invention provides an efficient way of optimizing a protein variant for a desired activity by making one or more protein variant libraries that incorporate only certain variable amino acid residue substitutions from a set of parental polypeptides. The set of variable amino acid residues are selected for incorporation into a protein variant library based on the evolutionary context of the variable amino acid residue Those substitutions that represent evolutionarily conservative substitutions are incorporated into protein variants of the library.

Amino acid changes allowed by evolution generally conserve fold and function of proteins. On relatively short evolutionary timescales, allowed changes tend to be context independent, that is, make an "additive" fitness contribution (and work well with other changes). Essentially infinite sources of homologues on any desired divergence timescale can be accessed by "allowed" amino acid changes for that timescale. There is also evidence that subtle perturbations in protein structure can have a huge impact on function (Kidokoro (1998) "Design of protein function by physical perturbation method," *Adv. Biophys.* 35:121-143, and Shimotohno et al. (2001) "Demonstration of the importance and usefulness of manipulating non-active-site residues in protein design," *J. Biochem.* (Tokyo) 129:943-948).

The present invention provides methods for searching sequence space by making evolutionarily conservative substitutions to generate diversity with high fitness levels. According to the methods, for example, parental sequences are aligned to determine which residues vary between parental sequences (i.e., are flexible), then an evolutionary substitution matrix is applied to identify a subset of the variable residues that represent conservative substitutions. A protein variant library is then generated that incorporates the conservative subset of variable amino acid residues into the sequences of the protein variants. Alternatively, other substitution matrices can be used to identify the subset of variable residues to incorporate into a protein variant library. Other suitable substitution matrices include those based on physicochemical properties or other parameters described herein. Optionally, the methods can be applied to single sequences by applying a user-defined filter or constraint, such as that cysteine, proline, and glycine residues remain unchanged (i.e., are less tolerant to change), and then apply a substitution matrix to the other residues.

Typically, a substitution matrix, such as Dayhoff's PAM matrices (for various PAM distances), site dependent matrices, BLOSUM matrices, JTT matrices, simply binary matrices that capture any amino acid classification, and the like can be used to create different timescales (see, e.g., Dayhoff and Eck (1968) "A model of evolutionary change in proteins," *Atlas of Protein Sequence and Structure* 3:33-41, and Henikoff and Henikoff (1992) "Amino acid substitution matrices from protein blocks," *Proc. Nat'l. Acad. Sci. USA* 89:10915-10919). Tuning the probability of transition from one amino acid to another can change the level of conservation. Both the probability cutoff and the matrix itself are parameters in the model. There are several other matrices that are also available. These matrices can be structure dependent, that is, the inside core of a protein has patterns of substitution that may differ from the external surface of the protein, helices can have different patterns from strands, and the like (Koshi and Goldstein (1997) "Mutation matrices and physical-chemical properties: correlations and implications," *Proteins* 27:336-344, and Koshi and Goldstein (1996) "Correlating structure-dependent mutation matrices with physical-chemical properties," *Pac. Symp. Biocomput.* 488-499). A physicochemical property-based matrix can also be used to select suitable substitutions. Additional details regarding substitution matrices suitable for use in the present invention are discussed further in, e.g., Durbin et al., *Biological Sequence Analysis: Probabilistic Models of Proteins and Amino Acids*, Cambridge University Press (1998). In using any of the above matrices, a library of variant polypeptides that incorporates conservative diversity and/or non-conservative diversity, can be made. For non-conservative libraries, substitutions that are less likely to happen under divergent evolution are typically selected.

When structures of the proteins of interest are available, regions/residues can be identified that will have the desired impact on protein function. This can be achieved by, e.g., simple modeling of changes in electrostatics around active sites or changes that lead to modified dynamics in the protein (Kidokoro, supra). Structural information can also be used to identify domain/modules that will have the most impact and one can limit their efforts only to that selected region of the proteins.

Algorithms of the present invention can be used to construct a series of libraries, for any given gene, with a continuum of median fitness, a continuum of genetic and phenotypic variance, and a high level of additive genetic variability. The algorithms are essentially "automatic" in the sense that they are implemented relatively independent of expert knowledge of the protein.

Figure 11:
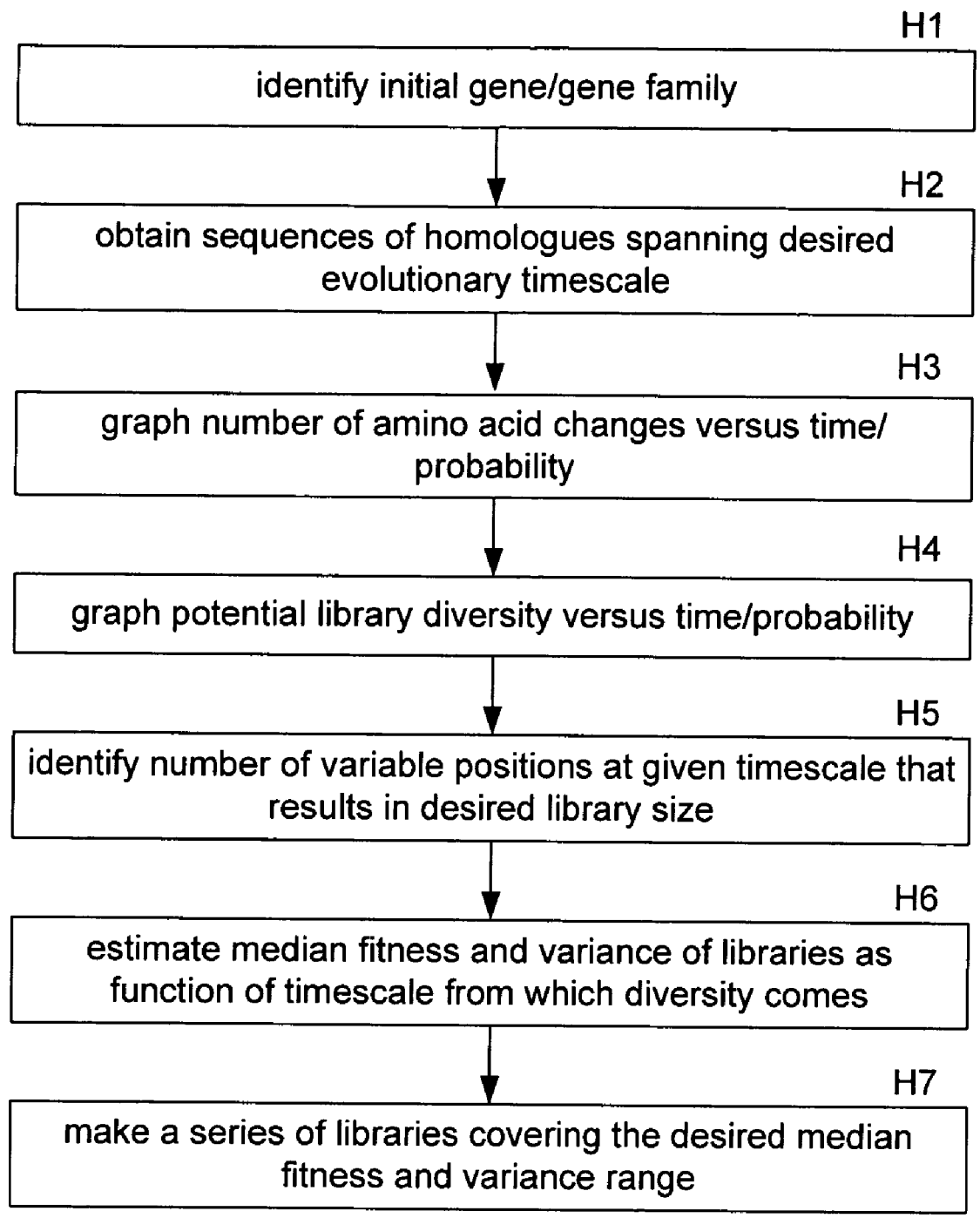
FIG. 11 is a chart that depicts certain steps performed in one embodiment of a method for efficiently searching sequence space.
Figure 12:
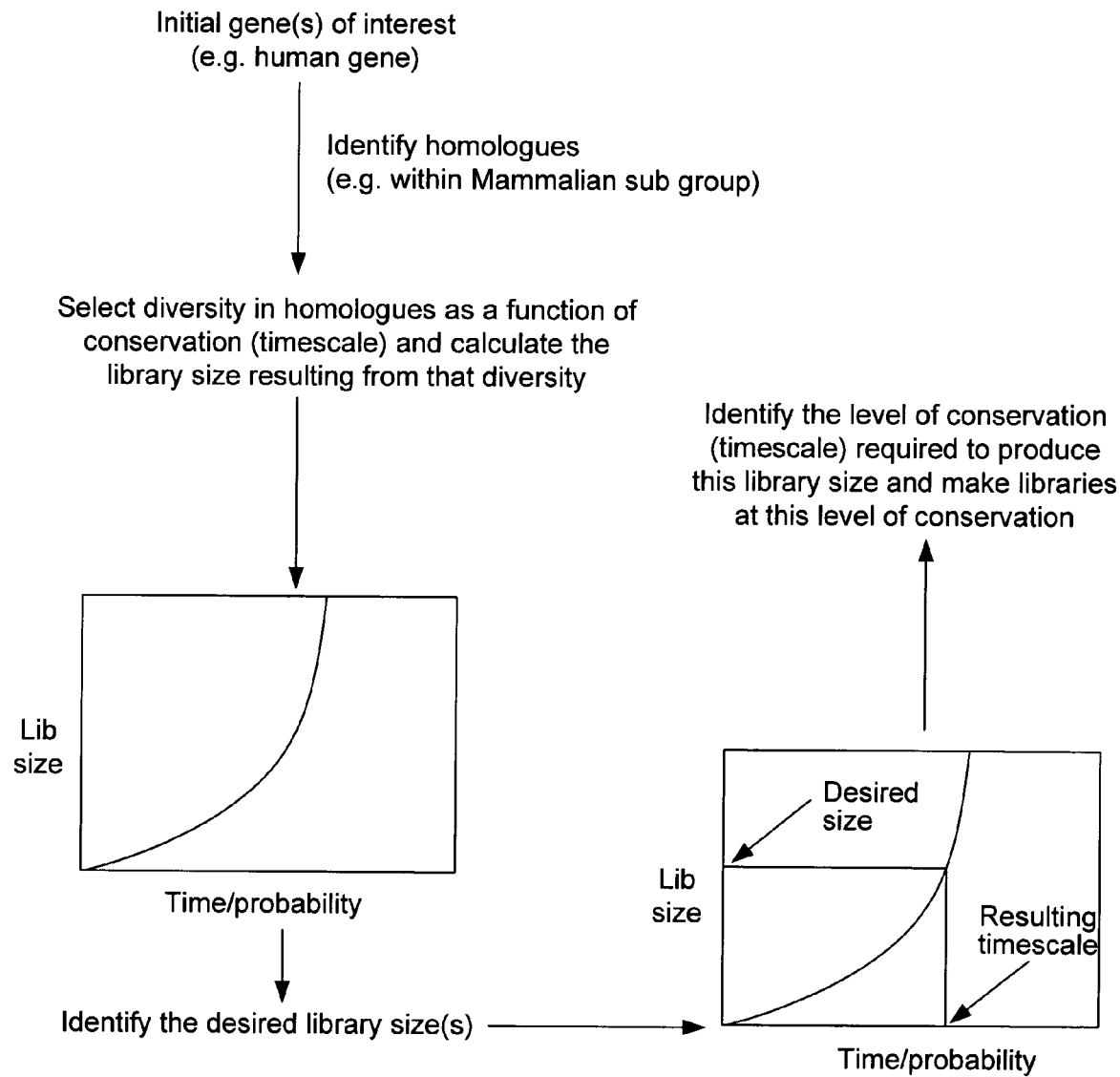
FIG. 12 is a chart that illustrates certain steps performed in one embodiment of a method for efficiently searching sequence space.

As an overview of these methods, FIG. 11 provides a chart that depicts certain steps performed in one method embodiment for efficiently searching sequence space. As shown, the method includes identifying an initial gene or gene family (i.e., gene of interest)(H1), obtaining sequences of homologues spanning a desired evolutionary timescale (H2), and evaluating the number and type of amino acid changes (e.g., with respect to the polypeptide encoded by the initial gene) that are identified as a function of time/probability (P) (i.e., indicated by timescale or probability of such mutation to occur in nature; level of conservation) (H3). The method also includes evaluating potential library diversity as a function of time/probability (H4), and identifying the number of variable positions at the given timescale that results in the desired library size (e.g., based upon the screening throughput and expected fitness of the new library) (H5). Further, the method include estimating median fitness and variance of libraries as a function of the timescale from which the diversity comes (H6), and making a series of libraries covering the desired median fitness and variance range (H7).

All of these methods can be implemented for an entire alignment and/or for a specific user defined set of residues or using structural information to make libraries of domains (modules, sub-domains, etc.). For diversity generation, these matrices-based approaches can be used in conjunction with other methods like PCA, PLS, PCR, MLR, or the like, where load information (e.g., site entropies) on specific sites of the protein can attach significance to substitution possibilities. Information from consensus sequences can be used to restrict or increase diversity in the library. Ancestral sequence reconstruction methods can reliably identify changes that took place in the set of proteins very early on in the evolutionary process, and changes that are adaptive in nature. This can be automatically used in the approaches described herein to make desired libraries.

These methods typicaily include various selection stringencies and libraries sizes. For example, assessments of the "fragility" of a protein are optionally made by estimations. Such estimations are typically governed by model studies of protein folding (e.g., already in the literature, etc.), empirical data (e.g., screen about 100-1000 hits per library, etc.), extrapolations from the rate of changes in evolution, size of library that can be screened, and/or the like. Libraries typically include between about $10^3$ and about $10^{12}$ members, depending upon the particular screening methods utilized. For example, one should consider the correlation of the screen with downstream higher complexity screens.

These methods for high efficiency sequence space searches provide many different advantages. In particular, the general approach becomes more powerful and refined as data on proteins/folds of interest accumulates. Also, desired sequence space can be automatically defined from phylogenetic data using a computer. In addition, phylogenetic information about "safe" steps (e.g., conservative residue substitutions) can be harnessed for subsequent analysis and development.

In certain aspects, the present invention provides a system for producing libraries of desired sizes. The system includes (a) at least one computer that includes a database capable of storing sets of biopolymer character strings, and (b) system software. The system software includes one or more logic instructions for: (i) identifying one or more homologues of at least one initial polypeptide sequence, (ii) comparing the sequences of the homologue(s) and the initial polypeptide; (iii) identifying variable amino acid residues, wherein variable amino acid residues differ with respect to amino acid residue type at corresponding positions in the sequences of the homologue(s) and the initial polypeptide sequence; (iv) identifying a set of evolutionarily conserved variable amino acid residues; and (v) generating a library of protein variants incorporating the set of evolutionarily conserved variable amino acid residues. The system software also includes instructions for (iv) identifying variable monomer positions in the at least one initial biopolymer character string from the selected evolutionary timescale that result in a desired library size, and (v) providing a series of libraries that comprise a selected median fitness and variance range.

The invention also includes a computer program product for producing libraries of desired sizes. The computer program product includes a computer readable medium having one or more logic instructions for: (a) identifying one or more homologues of at least one initial biopolymer character string from a selected evolutionary timescale, (b) plotting a number of monomer changes for the at least one initial biopolymer character string against a time/probability, and (c) plotting potential library size against the time/probability. The computer program product also includes instructions for (d) identifying variable monomer positions in the at least one initial biopolymer character string from the selected evolutionary timescale that result in a desired library size, and (e) providing a series of libraries that comprise a selected median fitness and variance range.

IV. Sequence Activity Predictions

A. Use of Neural Networks to Identify DNA or Protein Sequences with Improved Characteristics In the present invention neural networks are used to analyze data derived from various artificial evolution processes, including DNA shuffling, to predict sequences that have improved characteristics. In one example, such neural networks may be used in genetic algorithms to optimize sequences for further protein variant libraries. In brief, the methods include using data from each round of, e.g., a shuffling procedure as a training set for a neural network. Once a neural network has been trained, character string sequences can be "assayed" in silico using the trained network. Sequences which the network identifies as having improved characteristics are then typically added to subsequent rounds of shuffling, or synthesized de novo. Scoring systems used to rate these newly predicted character string sequences optionally take into account not only the neural network predicted score, but also a score of how many derivative character string sequences (e.g., character string variants of the newly predicted character string sequences) also have a high neural network score. For example, if character string sequence A was mutated into 1000 character string variants, and each variant was scored according to the network, the percentage of character string variants that score above a certain cutoff in the neural network are optionally counted. Further, this data may be combined with the neural network score of character string sequence A to produce a final score. Such a score would represent not only what the network predicted for that sequence, but also how probable that sequence is to mutate into as good or better sequences.

Figure 13:
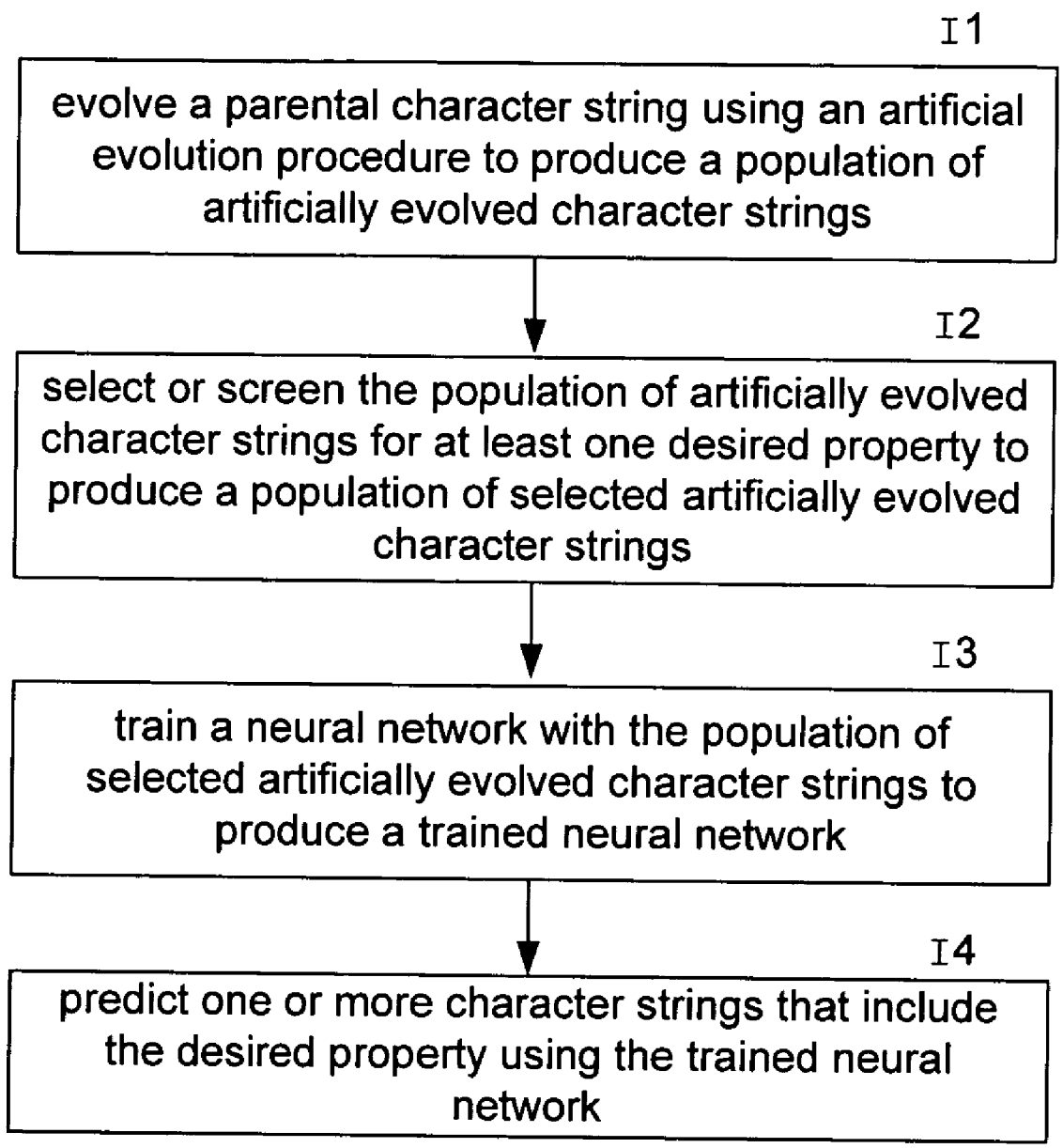
FIG. 13 is a chart that shows certain steps performed in an embodiment of a method of predicting character strings that include desired properties.

To further illustrate, FIG. 13 provides a chart that shows certain steps performed in an embodiment of a method of predicting character strings that include desired properties. As shown, the methods include evolving at least one parental character string (e.g., a plurality of parental character strings, etc.) using at least one artificial evolution procedure to produce at least one population of artificially evolved character strings (I1). Artificial evolution procedures carried out on character strings are typically performed reiteratively to produce multiple populations of artificially evolved character strings, which multiple populations of artificially evolved character strings are used to train the neural network. The methods also include selecting or screening the population of artificially evolved character strings for at least one desired property (e.g., a physical property, a catalytic property, or the like that is improved property relative to the parental character string) to produce a population of selected artificially evolved character strings (I2). The methods also include training a neural network with the population of selected artificially evolved character strings to produce a trained neural network (I3). Thereafter, the methods include predicting character strings that include, or are likely to include, the desired property using the trained neural network (I4). Additional details relating to neural networks are provided above.

In certain embodiments, the methods further include repeating steps I1 and I2 using the population of selected artificially evolved character strings in step I2 as the at least one parental character string in a repeated step I1. In these embodiments, the methods optionally further include using the population of selected artificially evolved character strings from at least one repeated step I2 to further train the neural network in step I3. Parental character strings typically corresponds to polynucleotides or polypeptides. In some embodiments, the methods optionally further include synthesizing polynucleotides or polypeptides that correspond to the character strings predicted in step I4. In other embodiments, the methods further include repeating steps I1-I4 using at least one of the character strings predicted in step I4 as a parental character string in a repeated step I4. Typically, the methods further include using the trained neural network as a filter to bias library production toward active library members.

In particular, step I4 typically includes scoring multiple character strings using a scoring system of the trained neural network to predict the character strings with the desired property. The scoring system generally ranks scored character strings. In addition, the scoring system typically accounts for a number of progeny character strings from each character string that includes a score above a selected score. For example, the number of progeny character strings typically includes, e.g., between about two and about $10^5$ progeny character strings. Generally, the scoring system combines each character string score with each corresponding progeny character string score to produce a final score. The final score provides a measure of a probability of the character strings mutating into progeny character strings that are improved relative to the character strings.

The artificial evolution procedures used in step I1 are optionally performed in silico and accordingly, typically include applying genetic operators to parental character strings to produce the population of artificially evolved character strings. Exemplary genetic operators optionally used in these methods include, e.g., a mutation of the at least one parental character string or substrings of the at least one parental character string, a multiplication of the at least one parental character string or substrings of the at least one parental character string, a fragmentation of the at least one parental character string into substrings, a crossover between parental character strings or substrings of the parental character strings, a ligation of parental character strings or substrings of the parental character strings, an elitism calculation, a calculation of sequence homology or sequence similarity of an alignment comprising parental character strings, a recursive use of at least one of the one or more genetic operators, an application of a randomness operator to the at least one parental character string or substrings of the at least one parental character string, a deletion mutation of one or more parental character strings or substrings of the one or more parental character strings, an insertion mutation into the at least one parental character string or substrings of the parental character string, a subtraction of parental character strings with inactive sequences, a selection of parental character strings with active sequences, a death of parental character strings or substrings of the parental character strings, or the like.

The invention also provides a computer system for predicting character strings that include desired properties. The system includes (a) a computer system that includes a neural network and a database capable of storing character strings, and (b) system software. The system software includes one or more logic instructions for (i) evolving at least one parental character string using at least one artificial evolution procedure to produce at least one population of artificially evolved character strings, and (ii) selecting or screening the population of artificially evolved character strings for at least one desired property to produce a population of selected artificially evolved character strings. The software also includes instructions for (iii) training the neural network with the population of selected artificially evolved character strings to produce a trained neural network, and (iv) predicting one or more character strings that comprise the at least one desired property using the trained neural network.

In another aspect, the invention relates to a computer program product for predicting character strings that include desired properties. The computer program product includes a computer readable medium having one or more logic instructions for (a) evolving at least one parental character string using at least one artificial evolution procedure to produce at least one population of artificially evolved character strings, and (b) selecting or screening the population of artificially evolved character strings for at least one desired property to produce a population of selected artificially evolved character strings. The product also includes instructions for (c) training a neural network with the population of selected artificially evolved character strings to produce a trained neural network, and (d) predicting one or more character strings that comprise the at least one desired property using the trained neural network. Systems and software are described further herein.

B. Use of Pattern or Motif Finding Algorithms to Analyze Sequence Space

There are many computer programs available for searching and finding and motifs within a group of sequences. Typically, these programs are limited to characterizing sequences as part of a broad protein family or not. In the present invention, motif finding programs are used to characterize and predict the activity of proteins, e.g., artificially evolved proteins. For example, positive sequences (e.g., those having a desired level of fitness), negative sequences (e.g., those lacking a desired level of fitness), and parents are optionally entered into pattern finding programs separately. However, all types of sequences are optionally entered into the pattern finding program together, e.g., to increase the sensitivity to finding any patterns. Due to the generally higher homology of positive sequences, motif finding programs typically find many motifs or patterns that exist within each sequence group. Patterns are optionally scored according to a frequency of occurrence in each group, to a frequency of absence from each sequence group, and/or the like. Additionally, detected patterns are also optionally entered into another pattern recognition algorithm such as a neural network. Once pattern recognition and scoring are complete, hypothetical sequences are scored in order to find additional sequences that will or are more likely to have the desired activity/property. Further, PCA analysis is optionally performed on pattern finding results to determine if there are combinations of motifs or patterns that are predictive of activity, which are then used to score additional protein sequences. These methods are typically implemented in web- or other software-based embodiments, and optionally coupled with additional bioinformatics analysis tools, such as crossover analysis, shuffling analysis, oligo creation, structural analysis, etc. in order to sell molecular biology kits for shuffling, selling oligos, or other bioinformatics software or services.

In certain embodiments, search trees are generated, which are, e.g., based on a scoring method in order to organize patterns, or groups of patterns in such a way to permit traversing the tree instead of trying all possible patterns, and combination of patterns. For example, patterns are optionally scored by how often they show up in positive/negative sequences. Instead of individual patterns, PCA analysis or the like is optionally performed to determine combinations of patterns for each of the nodes. To illustrate, the results of searching patterns on the positive and negative sequences are optionally analyzed using PCA. A load cutoff value is typically used for each principal component and a resulting pattern (e.g., a list of patterns) would then correspond to the nodes of the tree.

Figure 14:
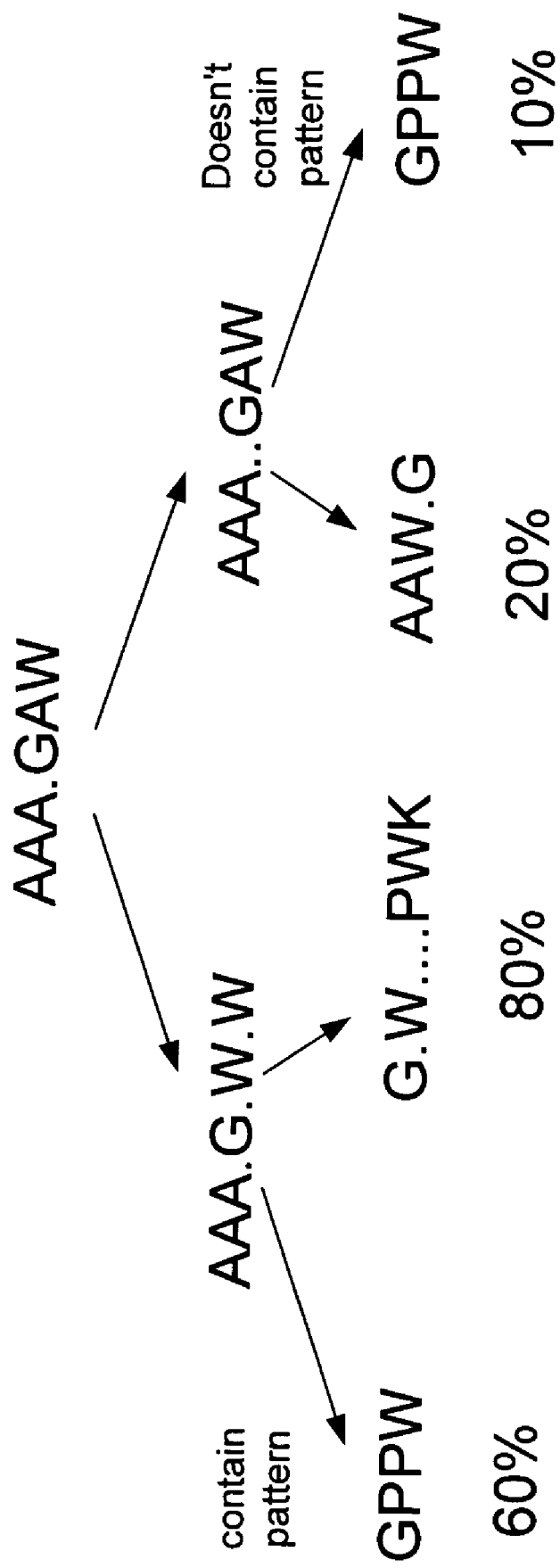
FIG. 14 schematically illustrates an example organizational tree according to one embodiment of the invention.

In addition, patterns are optionally scored with a value that relates, e.g., to relative information content, importance, fitness etc. as well as a value of predicted activity. These are optionally used again to train neural networks or to build a decision tree to rank or score hypothetical proteins or other biopolymers. For example, if the pattern AAA.GAW is found to be the most important, then hypothetical proteins are typically checked on the basis of whether they have the next most important pattern in that sub-branch. This process is optionally continued on with the next most important pattern given, e.g., that the first one was found or not found, and classify the sequence based on that sequence. The "contains" and "does not contain" sub-trees may include similar nodes (i.e., patterns), or they may not depending on how important a particular pattern is given its parent node lineage. To further illustrate, FIG. 14 schematically shows an example organizational tree. In the example, if a pattern has the three patterns AAA.GAW, AAA.G.W.W, and GPPW, then its probability of having the desired activity is 60%. Further, it might be based on the fact that 60% of the positive sequences have these three patterns.

Figure 15:
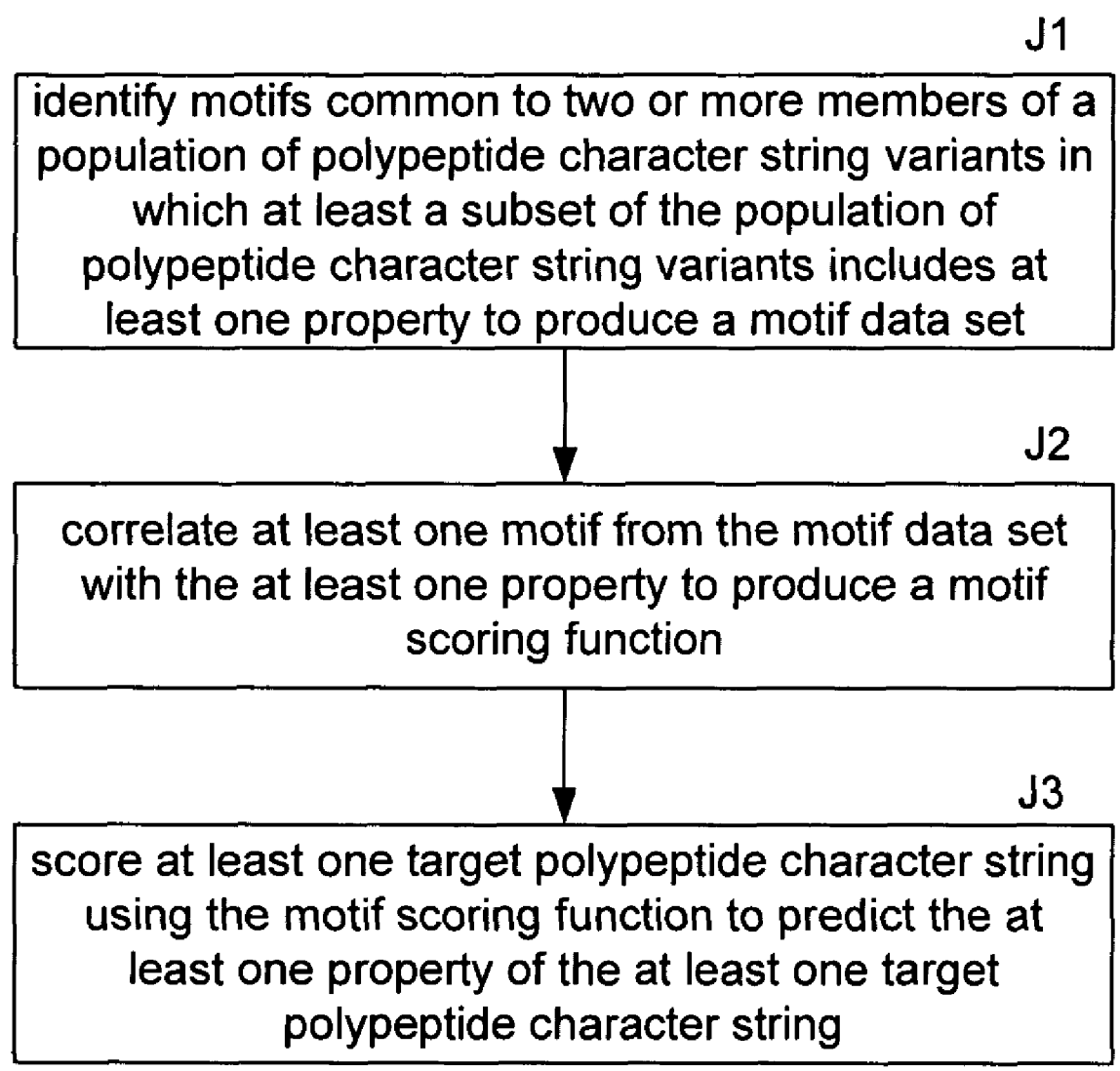
FIG. 15 is a chart that depicts certain steps performed in one embodiment of a method of predicting properties of target polypeptide character strings.

FIG. 15 is a chart that depicts certain steps performed in one embodiment of the methods of predicting properties of target polypeptide character strings (e.g., at least one hypothetical polypeptide character string, etc.). As shown, the methods include identifying one or more motifs common to two or more members of a population of polypeptide character string variants in which at least a subset of the population of polypeptide character string variants includes the at least one property (e.g., a functional property, a structural property, and/or the like), to produce a motif data set (J1). In certain embodiments, a phylogenetic family includes the polypeptide character string variants. At least one of the one or more motifs typically includes one or more character substrings. Typically, the at least one target polypeptide includes a population of target polypeptide character strings. In these embodiments, the population of target polypeptide character strings is generally produced by one or more artificial evolution procedures. The methods also include J2 correlating at least one motif from the motif data set with the at least one property to produce a motif scoring function, and J3 scoring the at least one target polypeptide character string using the motif scoring function to predict the at least one property of the at least one target polypeptide character string. At least one step of these methods is typically performed in a digital or web-based system. Optionally, the methods further include synthesizing a polypeptide corresponding to the target polypeptide character string. An additional option includes subjecting the polypeptide, or a polynucleotide that encodes the polypeptide, one or more artificial evolution procedures.

Motif scoring functions are produced using variations techniques. For example, step J2 optionally includes scoring the motifs or combinations of the motifs according frequencies of occurrence in positive polypeptide character string variants or negative polypeptide character string variants to produce the motif scoring function. In some embodiments, step J2 includes scoring the motifs, or combinations of the motifs, with a value relating to relative information content and/or relative fitness. In other embodiments, step J2 includes scoring the motifs, or combinations of the motifs, with values relating to relative predictive activity. In still other embodiments, step J2 includes determining a number of times the one or more motifs occur in or are absent from the two or more members of the population of polypeptide character string variants.

In certain embodiments, the population of polypeptide character string variants includes one or more polypeptide character string variant groups. Each polypeptide character string variant group optionally includes, e.g., positive polypeptide character string variants, negative polypeptide character string variants, and/or parental polypeptide character string variants. The polypeptide character string variants are typically produced by, or correspond to polypeptides produced by, one or more artificial evolution procedures. At least one (and typically more than one) step of the one or more artificial evolution techniques is generally performed in silico.

In preferred embodiments, at least step J1 is performed in at least one logic device that includes at least one first motif recognition algorithm, which first motif recognition algorithm identifies the one or more motifs. Typically, each method step is performed in the at least one logic device. Optionally, the methods further include producing at least one classification tree (e.g., at least one classification and regression tree (CART), etc.) to organize the motifs of the motif data set. For example, the at least one classification tree typically permits searching the motif data set without trying all of the motifs or combinations of motifs in the motif data set.

In some embodiments, the methods further include performing principal component analysis on the motif data set to identify one or more combinations of motifs that are predictive of the at least one desired property. Optionally, the methods further include performing a partial least squares analysis on the motif data set to identify one or more combinations of motifs that are predictive of the desired property. The one or more identified combinations of motifs are typically used to further refine the motif scoring function. In addition, the methods optionally further include producing at least one classification tree (e.g., at least one classification and regression tree, etc.) to organize the one or more combinations of motifs. In these embodiments, the one or more combinations of motifs typically include nodes in the at least one classification tree. Typically, the at least one classification tree permits searching the motif data set without trying all of the motifs or combinations of motifs in the motif data set. In certain other embodiments, the methods further include subjecting the motif data set to at least one second pattern recognition algorithm, which second pattern recognition algorithm identifies at least one additional motif common to at least two members of the population of polypeptide character string variants. For example, the second pattern recognition algorithm optionally includes a neural network. Neural networks are described further herein.

The invention also provides a system for predicting at least one property of at least one target polypeptide character string. The system includes (a) at least one computer that includes a database capable of storing character strings, and (b) system software. The system software includes one or more logic instructions for (i) identifying one or more motifs common to two or more members of a population of polypeptide character string variants, wherein at least a subset of the population of polypeptide character string variants comprises the at least one property, to produce a motif data set. The software also includes instructions for (ii) correlating at least one motif from the motif data set with the at least one property to produce a motif scoring function, and (iii) scoring the at least one target polypeptide character string using the motif scoring function to predict the at least one property of the at least one target polypeptide character string.

In addition, the invention also relates to a computer program product for predicting at least one property of at least one target polypeptide character string. The computer program product includes a computer readable medium having one or more logic instructions for (a) identifying one or more motifs common to two or more members of a population of polypeptide character string variants, wherein at least a subset of the population of polypeptide character string variants comprises the at least one property, to produce a motif data set. The computer program product also includes instructions for (b) correlating at least one motif from the motif data set with the at least one property to produce a motif scoring function, and (c) scoring the at least one target polypeptide character string using the motif scoring function to predict the at least one property of the at least one target polypeptide character string.

C. In Silico Directed Evolution with Functional Screening Using PCA and Neural Networks In certain embodiments, at least one member of the set of parental character strings is obtained from at least one database. In some of these embodiments, the at least one member includes substantially all character strings available from the database. Typically, at least one member of the set of parental character strings is produced by, or corresponds to at least one polynucleotide or at least one polypeptide produced by, one or more artificial evolution procedures. At least one step of the artificial evolution procedures is typically performed in silico. In some embodiments, the set of parental character strings corresponds to a set of parental polynucleotides or polypeptides.

The invention also provides a system for assigning an activity to a character string. The system includes (a) at least one computer that includes a database capable of storing character strings, and (b) system software. The system software includes one or more logic instructions for (i) selecting a set of parental character strings for at least one activity to produce a set of selected parental character strings, and (ii) subjecting the set of selected parental character strings to one or more artificial evolution procedures to produce a set of evolved character strings. The system software also includes instructions for (iii) selecting the set of evolved character strings for the at least one activity to produce a set of selected evolved character strings, (iv) providing a sequence-activity plot for the set of character string variants, and (v) predicting at least one activity of one or more character strings from the sequence-activity plot.

In addition, the invention provides a computer program product for predicting character string activities. The computer program product includes a computer readable medium having one or more logic instructions for (a) selecting a set of parental character strings for at least one activity to produce a set of selected parental character strings, and (b) subjecting the set of selected parental character strings to one or more artificial evolution procedures to produce a set of evolved character strings. The product also includes instructions for (c) selecting the set of evolved character strings for the at least one activity to produce a set of selected evolved character strings, (d) providing a sequence-activity plot for the set of character string variants, and (e) predicting at least one activity of one or more character strings from the sequence-activity plot.

V. Experimental Techniques

A. Protein Variant Libraries

Libraries of protein variants can be generated using any of a variety of methods that are well known to those having ordinary skill in the art. These libraries are typically prepared by expression, either in vivo or in vitro, of a library of diverse polynucleotides. Libraries of diverse polynucleotides can be generated by application of a "diversity generating procedure" to one or more "parental" polynucleotides.

As used herein, the term "diversity generating procedure" refers to a method that modifies the sequence of a parental polynucleotide, and concomitantly the polypeptide it encodes, thereby generating a library of polynucleotide variants that differ from each other with respect to sequence. Diversity generating procedures that are suitable for use in the practice of the present invention include either mutagenesis and recombination-based methods, or a combination of both. Expression of the resulting polynucleotide variant library thus generates a library of polypeptide variants.

Protein variant libraries employed in the practice of the present invention may be made in a "blind" fashion, where the protein variant molecules are generated without prior knowledge of their amino acid sequences (i.e., where the polynucleotide variant sequences are not known prior to expression into a protein variant library). Alternatively, the amino acid sequences encoding the protein variants may be designed a priori, followed by the step of actually making the physical molecules using methods known to those having ordinary skill in the art. These methods include expression of polynucleotides generated by, for example, gene synthesis via ligation and/or polymerase-mediated oligonucleotide assembly and mutagenesis of a parental polynucleotide, using methods known in the art. Suitable methods for designing amino acid sequences of systematically varied protein variants include design of experiment methods (DOE), described in more detail herein.

Polynucleotide mutagenesis is a suitable method for generating the protein variants employed in the practice of the present invention. Such methods include, for example, error prone polymerase chain reaction (PCR), site-specific mutagenesis, cassette-mutagenesis, in vivo mutagenesis methods, and the like. In error-prone PCR, PCR is performed under conditions where the copying fidelity of the DNA polymerase is low, such that a high rate of point mutations is obtained along the entire length of the PCR product. See e.g., Leung et al. (1989) *Technique* 1:11-15 and Caldwell et al. (1992) *PCR Methods Applic.* 2:28-33. Site-specific mutations can be introduced in a polynucleotide sequence of interest using oligonucleotide-directed mutagenesis. See Reidhaar-Olson et al. (1988) *Science,* 241:53-57. Similarly, cassette mutagenesis can be used in a process that replaces a small region of a double stranded DNA molecule with a synthetic oligonucleotide cassette that differs from the native sequence. In vivo mutagenesis can be used to generate random mutations in any cloned DNA of interest by propagating the DNA in a host cell strain prone to generating mutations, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Mutagenesis methods are generally well known to those having ordinary skill in the art and are extensively described elsewhere. See e.g., Kramer et al. (1984) *Cell* 38:879-887; Carter et al. (1985) *Nucl. Acids Res.* 13: 4431-4443; Carter (1987) *Methods in Enzymol.* 154: 382-403; Eghtedarzadeh & Henikoff(1986) *Nucl. Acids Res.* 14: 5115;Wells et al. (1986) *Phil. Trans. R. Soc. Lond. A* 317:

415-423; Nambiar et al. (1984) *Science* 223: 1299-1301; Sakamar and Khorana (1988) *Nucl. Acids Res.* 14: 6361-6372; Wells et al. (1985) *Gene* 34:315-323; Grundström et al. (1985) *Nucl. Acids Res.* 13: 3305-3316; Mandecki (1986) *Proc. Natl. Acad. Sci. USA,* 83:7177-7181; Arnold (1993) *Current Opinion in Biotechnology* 4:450-455); *Anal Biochem.* 254(2): 157-178; Dale et al. (1996) *Methods Mol. Biol.* 57:369-374; Smith (1985) *Ann. Rev. Genet.* 19:423-462; Botstein & Shortle (1985) *Science* 229:1193-1201; Carter (1986) *Biochem. J.* 237:1-7; Kunkel (1987) in *Nucleic Acids & Molecular Biology,* Eckstein, F. and Lilley, D. M. J. eds., Springer Verlag, Berlin; Kunkel (1985) *Proc. Natl. Acad. Sci. USA* 82:488-492; Kunkel et al. (1987) *Methods in Enzymol.* 154, 367-382; and Bass et al. (1988) *Science* 242:240-245; *Methods in Enzymol.* 100: 468-500 (1983); *Methods in Enzymol.* 154: 329-350 (1987); Zoller & Smith (1982) *Nucleic Acids Res.* 10:6487-6500; Zoller & Smith (1983) *Methods in Enzymol.* 100:468-500; and Zoller & Smith (1987) *Methods in Enzymol.* 154:329-350); Taylor et al. (1985) *Nucl. Acids Res.* 13: 8749-8764; Taylor et al. (1985) *Nucl. Acids Res.* 13: 8765-8787 (1985); Nakamaye & Eckstein (1986) *Nucl. Acids Res.* 14: 9679-9698; Sayers et al. (1988) *Nucl. Acids Res.* 16:791-802; Sayers et al. (1988) *Nucl. Acids Res.* 16: 803-814); Kramer et al. (1984) *Nucl. Acids Res.* 12: 9441-9456; Kramer & Fritz (1987) *Methods in Enzymol.* 154:350-367; Kramer et al. (1988) *Nucl. Acids Res.* 16: 7207; and Fritz et al. (1988) *Nucl. Acids Res.* 16: 6987-6999.

Kits for mutagenesis, library construction and other diversity generation methods are commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method referenced above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method referenced above), and Anglian Biotechnology Ltd. (e.g., using the Carter/Winter method referenced above).

Recombination-based methods are also suitable for generating a diverse library of polynucleotide variants that can be expressed to generate a protein variant library. These methods are also referred to as DNA shuffling. In these methods, polynucleotides are recombined, either in vitro or in vivo, to generate a library of polynucleotide variants. In recombination-based methods, DNA fragments, PCR amplicons, and/or synthetic oligonucleotides that collectively correspond in sequence to some or all of the sequence of one or more parental polynucleotides are recombined to generate a library of polynucleotide variants of the parental polynucleotide(s). The recombination process may be mediated by hybridization of the DNA fragments, PCR amplicons, and/or synthetic oligonucleotides to each other (e.g., as partially overlapping duplexes), or to a larger piece of DNA, such as a full-length template. Depending on the recombination format employed, ligase and/or polymerase may be used to facilitate the construction of a full-length polynucleotide. PCR cycling is typically used in formats employing only a polymerase. These methods are generally known to those having ordinary skill in the art and are described extensively elsewhere. See e.g., Soong, N. et al. (2000) *Nat. Genet.* 25(4):436-439; Stemmer, et al. (1999) *Tumor Targeting* 4:1-4; Ness et al. (1999) *Nature Biotechnology* 17:893-896; Chang et al. (1999) *Nature Biotechnology* 17:793-797; Minshull and Stemmer (1999) *Current Opinion in Chemical Biology* 3:284-290; Christians et al. (1999) *Nature Biotechnology* 17:259-264; Crameri et al. (1998) *Nature* 391:288-291; Crameri et al. (1997) *Nature Biotechnology* 15:436-438; Zhang et al. (1997) *Proc. Natl. Acad. Sci. USA* 94:4504-4509; Patten et al. (1997) *Current Opinion in Biotechnology* 8:724-733; Crameri et al. (1996) *Nature Medicine* 2:100-103; Crameri et al. (1996) *Nature Biotechnology* 14:315-319; Gates et al. (1996) *Journal of Molecular Biology* 255:373-386; Stemmer (1996) In: *The Encyclopedia of Molecular Biology*. VCH Publishers, New York. pp.447-457; Crameri and Stemmer (1995) *BioTechniques* 18:194-195; Stemmer et al., (1995) *Gene,* 164:49-53; Stemmer (1995) "The Evolution of Molecular Computation" *Science* 270: 1510; Stemmer (1995) *Bio/Technology* 13:549-553; Stemmer (1994) *Nature* 370:389-391; and Stemmer (1994) *Proc. Natl. Acad. Sci. USA* 91:10747-10751; Giver and Arnold (1998) Current Opinion in Chemical Biology 2:335-338; Zhao et al. (1998) *Nature Biotechnology* 16:258-261; Coco et al. (2001) *Nature Biotechnology* 19:354-359; U.S. Pat. Nos. 5,605,793, 5,811,238, 5,830,721, 5,834,252, 5,837,458, WO 95/22625, WO 96/33207, WO 97/20078, WO 97/35966, WO 99/41402, WO 99/41383, WO 99/41369, WO 99/41368, WO 99/23107, WO 99/21979, WO 98/31837, WO 98/27230, WO 98/27230, WO 00/00632, WO 00/09679, WO 98/42832, WO 99/29902, WO 98/41653, WO 98/41622, and WO 98/42727, WO 00/18906, WO 00/04190, WO 00/42561, WO 00/42559, WO 00/42560, WO 01/23401, WO 00/20573, WO 01/29211, WO 00/46344, and WO 01/29212.

Parental polynucleotides employed in the recombination processes reference above may be either wildtype polynucleotides or non-naturally occurring polynucleotides. In one embodiment of the present invention, protein variants having systematically varied sequences are prepared by recombination of two or more parental polynucleotides followed by expression. In some embodiments, the parental polynucleotides are members of a single gene family. As used herein, the term "gene family" refers to a set of genes that encode polypeptides which exhibit the same type, although not necessarily the same degree, of an activity.

Polynucleic acids can be recombined in vitro by any of a variety of techniques, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described, e.g., in Stemmer (1994) *Proc. Natl. Acad. Sci. USA* 91:10747-10751.

Synthetic recombination methods can also be used, in which oligonucleotides corresponding to targets of interest are chemically synthesized and reassembled in PCR or ligation reactions which include oligonucleotides that correspond to more than one parental polynucleotide, thereby generating new recombined polynucleotides. Oligonucleotides can be made by standard nucleotide addition methods, or can be made, e.g., by tri-nucleotide synthetic approaches. Details regarding such approaches are found in the references noted above, e.g., WO 00/42561 by Crameri et al., "Olgonucleotide Mediated Nucleic Acid Recombination;" WO 01/23401 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

Polynucleotides can also be recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references cited herein.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. These methods can be used in physical systems or can be performed in computer systems according to specific embodiments of the invention. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, WO 01/64864.

Methods of recombination can also be performed digitally on an information processing system. For example, algorithms can be used in a computer to recombine sequence strings that correspond to homologous (or even non-homologous) bio-molecules. According to specific embodiments of the invention, after processing in a computer system, the resulting sequence strings can be converted into nucleic acids by synthesis of nucleic acids which correspond to the recombined sequences, e.g., in concert with oligonucleotide synthesis/gene reassembly techniques. This approach can generate random, partially random, or designed variants. Many details regarding various embodiments of computer enabled recombination, including the use of various algorithms, operators and the like in computer systems, as well as combinations of designed nucleic acids and/or proteins (e.g., based on cross-over site selection) as well as designed, pseudo-random or random recombination methods are described in WO 00/42560 by Selifonov et al., "Methods for Making Character Strings, Polynucleotides and Polypeptides Having Desired Characteristics," WO 01/75767 by Gustafsson et al., "In Silico Cross-Over Site Selection," and WO 00/42559 by Selifonov and Stemmer "Methods of Populating Data Structures for Use in Evolutionary Simulations."

B. Directed Evolution

Directed evolution (or alternatively "artificial evolution") can be carried out by practicing one or more diversity generating methods in a reiterative fashion coupled with screening (described in more detail elsewhere herein) to generate a further set of recombinant nucleic acids. Thus, directed or artificial evolution can be carried out by repeated cycles of mutagenesis and/or recombination and screening. For example, mutagenesis and/or recombination can be carried out on parental polynucleotides to generate a library of variant polynucleotides that are then expressed to generate a protein variant library that is screen for a desired activity. One or more variant proteins may be identified from the protein variant library as exhibiting improvement in the desired activity. The identified proteins can be reverse translated to ascertain one or more polynucleotide sequences that encode the identified protein variants, which in turn can be mutated or recombined in a subsequent round of diversity generation and screening.

Directed evolution using recombination-based formats of diversity generation is described extensively in the references cited herein. Directed evolution using mutagenesis as the basis for diversity generation is also well known in the art. For example, recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811-7815. Similarly, exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548-1552.

Structure-activity models of the present invention are useful in optimizing the directed evolution process regardless of the diversity generating procedure employed. Information derived from application of the invention models can be used to more intelligently design libraries made in a directed evolution process. For example, where it is desired to toggle or fix residues at certain amino acid residue positions, synthetic oligonucleotides incorporating the codons encoding those desired amino acid residues can be used in one of the recombination formats referred to herein to generate a polynucleotide variant library that can then be expressed. Alternatively, the desired residues can be incorporated using one of the various mutagenesis methods described herein. In any event, the resulting protein variant library will thus contain protein variants that incorporate what are believed to be beneficial residues or potentially beneficial residues. This process can be repeated until a protein variant having the desired activity is identified.

C. Screening/Selection for Activity

Polynucleotides generated in connection with methods of the present invention are optionally cloned into cells for activity screening (or used in vitro transcription reactions to make products which are screened). Furthermore, the nucleic acids can be enriched, sequenced, expressed, amplified in vitro or treated in any other common recombinant method.

General texts that describe molecular biological techniques useful herein, including cloning, mutagenesis, library construction, screening assays, cell culture and the like include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 (Sambrook) and *Current Protocols in Molecular Biology*, F. M. Ausubel et al., eds., Current Protocols, a joint venture between Greene Publishing Associates, Inc. and John Wiley & Sons, Inc., New York (supplemented through 2000)

(Ausubel)). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016-1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

Examples of techniques sufficient to direct persons of skill through in vitro amplification methods, useful e.g., for amplifying oligonucleotide recombined nucleic acids including polymerase chain reactions (PCR), ligase chain reactions (LCR), Qβ-replicase amplifications and other RNA polymerase mediated techniques (e.g., NASBA). These techniques are found in Berger, Sambrook, and Ausubel, supra, as well as in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

In one preferred method, reassembled sequences are checked for incorporation of family-based recombination oligonucleotides. This can be done by cloning and sequencing the nucleic acids, and/or by restriction digestion, e.g., as essentially taught in Sambrook, Berger and Ausubel, supra. In addition, sequences can be PCR amplified and sequenced directly. Thus, in addition to, e.g., Sambrook, Berger, Ausubel and Innis (supra), additional PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611-1617). In the methods, four PCR reactions on a template are performed, in each of which one of the nucleotide triphosphates in the PCR reaction mixture is partially substituted with a 2'deoxy-nucleoside 5'-[P-borano]-triphosphate. The boronated nucleotide is stochastically incorporated into PCR products at varying positions along the PCR amplicon in a nested set of PCR fragments of the template. An exonuclease that is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons.

Synthetic genes are amenable to conventional cloning and expression approaches; thus, properties of the genes and proteins they encode can readily be examined after their expression in a host cell. Synthetic genes can also be used to generate polypeptide products by in vitro (cell-free) transcription and translation. Polynucleotides and polypeptides can thus be examined for their ability to bind a variety of predetermined ligands, small molecules and ions, or polymeric and heteropolymeric substances, including other proteins and polypeptide epitopes, as well as microbial cell walls, viral particles, surfaces and membranes.

For example, many physical methods can be used for detecting polynucleotides encoding phenotypes associated with catalysis of chemical reactions by either polynucleotides directly, or by encoded polypeptides. Solely for the purpose of illustration, and depending on the specifics of particular pre-determined chemical reactions of interest, these methods may include a multitude of techniques well known in the art which account for a physical difference between substrate(s) and product(s), or for changes in the reaction media associated with chemical reaction (e.g. changes in electromagnetic emissions, adsorption, dissipation, and fluorescence, whether UV, visible or infrared (heat)). These methods also can be selected from any combination of the following: mass-spectrometry; nuclear magnetic resonance; isotopically labeled materials, partitioning and spectral methods accounting for isotope distribution or labeled product formation; spectral and chemical methods to detect accompanying changes in ion or elemental compositions of reaction product(s) (including changes in pH, inorganic and organic ions and the like). Other methods of physical assays, suitable for use in the methods herein, can be based on the use of biosensors specific for reaction product(s), including those comprising antibodies with reporter properties, or those based on in vivo affinity recognition coupled with expression and activity of a reporter gene. Enzyme-coupled assays for reaction product detection and cell life-death-growth selections in vivo can also be used where appropriate. Regardless of the specific nature of the physical assays, they all are used to select a desired activity, or combination of desired activities, provided or encoded by a biomolecule of interest.

The specific assay used for the selection will depend on the application. Many assays for proteins, receptors, ligands and the like are known. Formats include binding to immobilized components, cell or organismal viability, production of reporter compositions, and the like.

High throughput assays are particularly suitable for screening libraries employed in the present invention. In high throughput assays, it is possible to screen up to several thousand different variants in a single day. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000-20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.) which can provide very high throughput microfluidic assay methods.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for various high throughput screening assays. Thus, for example, Zymark Corp. provides technical bulletins describing screening systems for detecting the modulation of gene transcription, ligand binding, and the like.

A variety of commercially available peripheral equipment and software is available for digitizing, storing and analyzing a digitized video or digitized optical or other assay images, e.g., using PC (Intel x86 or pentium chip-compatible DOS™, OS2™, WINDOWS™, or WINDOWS NT™ based machines), MACINTOSH™, or UNIX based (e.g., SUN™ work station) computers.

Systems for analysis typically include a digital computer with software for directing one or more step of one or more of the methods herein, and, optionally, also include, e.g., high-throughput liquid control software, image analysis software, data interpretation software, a robotic liquid control armature for transferring solutions from a source to a destination operably linked to the digital computer, an input device (e.g., a computer keyboard) for entering data to the digital computer to control operations or high throughput liquid transfer by the robotic liquid control armature and, optionally, an image scanner for digitizing label signals from labeled assay components. The image scanner can interface with image analysis software to provide a measurement of probe label intensity. Typically, the probe label intensity measurement is interpreted by the data interpretation software to show whether the labeled probe hybridizes to the DNA on the solid support.

Computational hardware and software resources are available that can be employed in the invention methods described herein (for hardware, any mid-range priced Unix system (e.g., for Sun Microsystems) or even higher end Macintosh or PCs will suffice).

In some embodiments, cells, viral plaques, spores or the like, comprising in vitro oligonucleotide-mediated recombination products or physical embodiments of in silico recombined nucleic acids, can be separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each parameter can be controlled and optimized.

The uniform process of automated colony picking such as the Q-bot decreases human handling error and increases the rate of establishing cultures (roughly 10,000/4 hours). These cultures are optionally shaken in a temperature and humidity controlled incubator. Optional glass balls in the microtiter plates act to promote uniform aeration of cells and the dispersal of cellular (e.g., mycelial) fragments similar to the blades of a fermentor. Clones from cultures of interest can be isolated by limiting dilution. As also described supra, plaques or cells constituting libraries can also be screened directly for the production of proteins, either by detecting hybridization, protein activity, protein binding to antibodies, or the like. To increase the chances of identifying a pool of sufficient size, a prescreen that increases the number of mutants processed by 10-fold can be used. The goal of the primary screen is to quickly identify mutants having equal or better product titers than the parent strain(s) and to move only these mutants forward to liquid cell culture for subsequent analysis.

One approach to screening diverse libraries is to use a massively parallel solid-phase procedure to screen cells expressing polynucleotide variants, e.g., polynucleotides that encode enzyme variants. Massively parallel solid-phase screening apparatus using absorption, fluorescence, or FRET are available. See, e.g., U.S. Pat. No. 5,914,245 to Bylina, et al. (1999); see also, http://www.kairos-scientific.com/; Youvan et al. (1999) "Fluorescence Imaging Micro-Spectrophotometer (FIMS)" *Biotechnology et alia*, <www.et-al.com> 1:1-16; Yang et al. (1998) "High Resolution Imaging Microscope (HIRIM)" *Biotechnology et alia*, <www.et-al.com> 4:1-20; and Youvan et al. (1999) "Calibration of Fluorescence Resonance Energy Transfer in Microscopy Using Genetically Engineered GFP Derivatives on Nickel Chelating Beads" posted at www.kairos-scientific.com. Following screening by these techniques, molecules of interest are typically isolated, and optionally sequenced using methods that are well known in the art. The sequence information is then used as set forth herein to design a new protein variant library.

Similarly, a number of well-known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual synthetic operations performed by a scientist. Any of the above devices are suitable for use with the present invention, e.g., for high-throughput screening of molecules encoded by nucleic acids evolved as described herein. The nature and implementation of modifications to these devices (if any) so that they can operate as discussed herein will be apparent to persons skilled in the relevant art.

VII. Digital Apparatus and Systems

As should be apparent, embodiments of the present invention employ processes acting under control of instructions and/or data stored in or transferred through one or more computer systems. Embodiments of the present invention also relate to apparatus for performing these operations. Such apparatus may be specially designed and/or constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein. In some cases, however, it may be more convenient to construct a specialized apparatus to perform the required method operations. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, magnetic tape; optical media such as CD-ROM devices and holographic devices; magneto-optical media; semiconductor memory devices, and hardware devices that are specially configured to store and perform program instructions, such as read-only memory devices (ROM) and random access memory (RAM), and sometimes application-specific integrated circuits (ASICs), programmable logic devices (PLDs) and signal transmission media for delivering computer-readable instructions, such as local area networks, wide area networks, and the Internet. The data and program instructions of this invention may also be embodied on a carrier wave or other transport medium (e.g., optical lines, electrical lines, and/or airwaves).

Examples of program instructions include both low-level code, such as produced by a compiler, and files containing higher level code that may be executed by the computer using an interpreter. Further, the program instructions include machine code, source code and any other code that directly or indirectly controls operation of a computing machine in accordance with this invention. The code may specify input, output, calculations, conditionals, branches, iterative loops, etc.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting one or more character strings into the software which is loaded into the memory of a digital system, and performing an operation as noted herein on the character string. For example, systems can include the foregoing software having the appropriate character string information, e.g., used in conjunction with a user interface (e.g., a GUI in a standard operating system such as a Windows, Macintosh or LINUX system) to manipulate strings of characters. Specialized alignment programs such as PILEUP and BLAST can also be incorporated into the systems of the invention, e.g., for alignment of nucleic acids or proteins (or corresponding character strings) as a preparatory step to performing an operation on any aligned sequences. Software for performing PCA (e.g., as is commercially available from Partek) or other statistical operations can also be included in the digital system.

Systems typically include, e.g., a digital computer with software for aligning and manipulating sequences according to the operations noted herein, or for performing PCA, neural network analysis or the like, as well as data sets entered into the software system comprising sequences or other data to be mapped or manipulated. The computer can be, e.g., a PC (Intel x86 or Pentium chip-compatible DOS™, OS2™, WINDOWS™, WINDOWS NT™, WINDOWS95™, WINDOWS98™, LINUX, Apple-compatible, MACINTOSH™ compatible, Power PC compatible, or a UNIX compatible (e.g., SUN™ work station or machine) or other common commercially available computer which is known to one of skill. Software for aligning or otherwise manipulating sequences can be constructed by one of skill using a standard programming language such as VisualBasic, Fortran, Basic, Java, or the like, according to the methods herein.

Any controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operation. For example, in addition to performing statistical manipulations of data space, a digital system can instruct an oligonucleotide synthesizer to synthesize oligonucleotides for gene reconstruction, or even to order oligonucleotides from commercial sources (e.g., by printing appropriate order forms or by linking to an order form on the internet).

The digital system can also include output elements for controlling nucleic acid synthesis (e.g., based upon a sequence or an alignment of a sequences herein), i.e., an integrated system of the invention optionally includes an oligonucleotide synthesizer or an oligonucleotide synthesis controller. The system can include other operations which occur downstream from an alignment or other operation performed using a character string corresponding to a sequence herein, e.g., as noted above with reference to assays.

Figure 16:
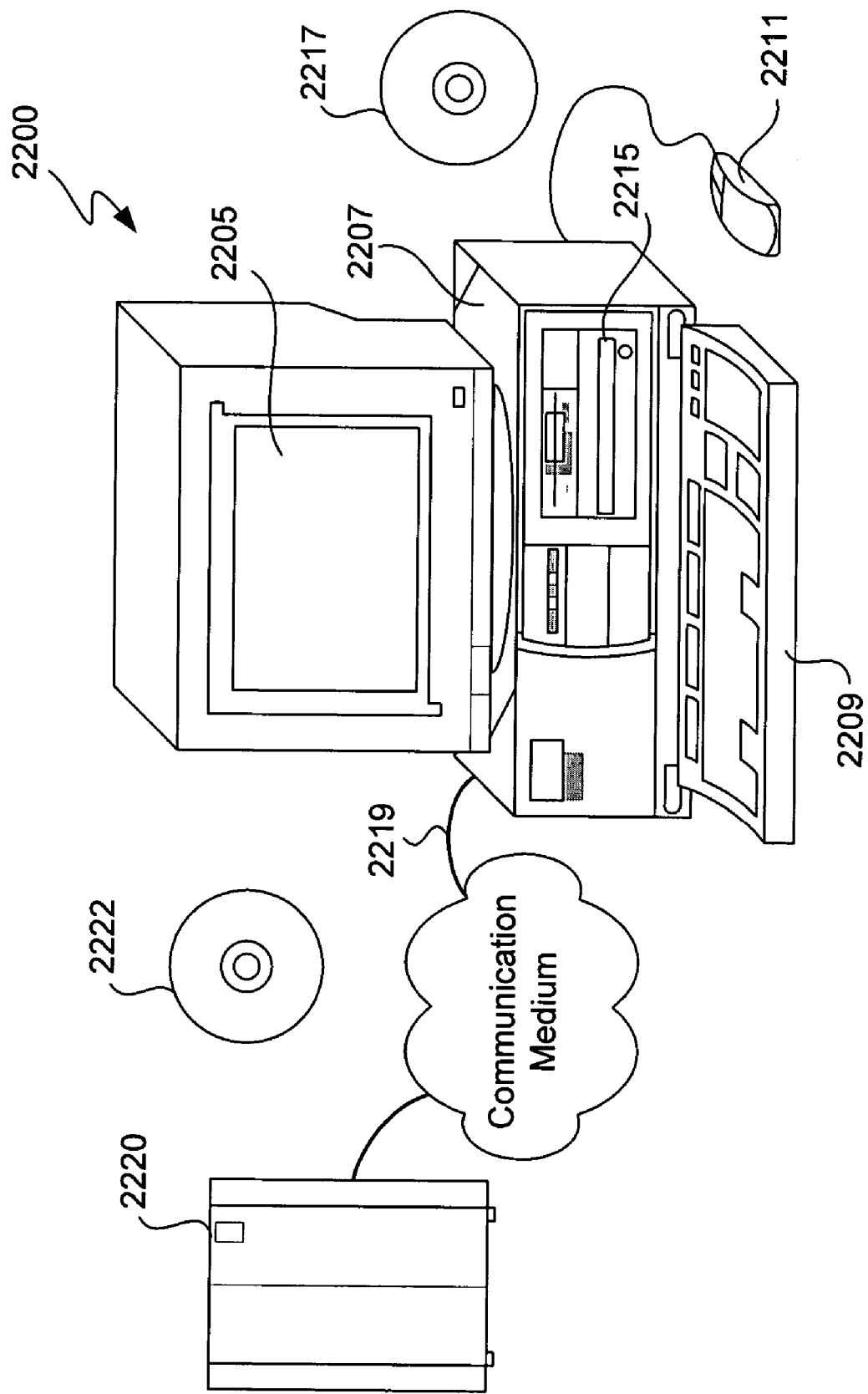
FIG. 16 is a schematic of an example digital device.

In one example, code embodying methods of the invention are embodied in a fixed media or transmissible program component containing logic instructions and/or data that when loaded into an appropriately configured computing device causes the device to perform a genetic operator on one or more character string. FIG. 16 shows an example digital device 2200 that should be understood to be a logical apparatus that can read instructions from media 2217, network port 2219, user input keyboard 2209, user input 2211 or other inputting means. Apparatus 2200 can thereafter use those instructions to direct statistical operations in data space, e.g., to construct one or more data set (e.g., to determine a plurality of representative members of the data space). One type of logical apparatus that can embody the invention is a computer system as in computer system 2200 comprising CPU 2207, optional user input devices keyboard 2209, and GUI pointing device 2211, as well as peripheral components such as disk drives 2215 and monitor 2205 (which displays GO modified character strings and provides for simplified selection of subsets of such character strings by a user. Fixed media 2217 is optionally used to program the overall system and can include, e.g., a disk-type optical or magnetic media or other electronic memory storage element. Communication port 2219 can be used to program the system and can represent any type of communication connection.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

In one preferred aspect, the digital system comprises a learning component where the outcomes of physical oligonucleotide assembly schemes (compositions, abundance of products, different processes) are monitored in conjunction with physical assays, and correlations are established. Successful and unsuccessful combinations are documented in a database to provide justification/preferences for user-base or digital system based selection of sets of parameters for subsequent processes described herein involving the same set of parental character strings/nucleic acids/proteins (or even unrelated sequences, where the information provides process improvement information). The correlations are used to modify subsequent processes of the invention, e.g., to optimize the particular process. This cycle of physical synthesis, selection and correlation is optionally repeated to optimize the system. For example, a learning neural network can be used to optimize outcomes.

VIII. Embodiments in Websites

The Internet includes computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages.

Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces, that information appliances use to communicate with remote information appliances or servers without necessarily displaying information to a user.

The Internet is especially conducive to providing information services to one or more remote customers. Services can include items (e.g., music or stock quotes) that are delivered electronically to a purchaser over the Internet. Services can also include handling orders for items (e.g., groceries, books, or chemical or biologic compounds, etc.) that may be delivered through conventional distribution channels (e.g., a common carrier). Services may also include handling orders for items, such as airline or theater reservations, that a purchaser accesses at a later time. A server computer system may provide an electronic version of an interface that lists items or services that are available. A user or a potential purchaser may access the interface using a browser and select various items of interest. When the user has completed selecting the items desired, the server computer system may then prompt the user for information needed to complete the service. This transaction-specific order information may include the purchaser's name or other identification, an identification for payment (such as a corporate purchase order number or account number), or additional information needed to complete the service, such as flight information.

NCBI Databases and Software

Among services of particular interest that can be provided over the internet and over other networks are biological data and biological databases. Such services include a variety of services provided by the National Center for Biotechnology Information (NCBI) of the National Institutes of Health (NIH). NCBI is charged with creating automated systems for storing and analyzing knowledge about molecular biology, biochemistry, and genetics; facilitating the use of such databases and software by the research and medical community; coordinating efforts to gather biotechnology information both nationally and internationally; and performing research into advanced methods of computer-based information processing for analyzing the structure and function of biologically important molecules.

NCBI holds responsibility for the GenBank® DNA sequence database. The database has been constructed from sequences submitted by individual laboratories and by data exchange with the international nucleotide sequence databases, the European Molecular Biology Laboratory (EMBL) and the DNA Database of Japan (DDBJ), and includes patent sequence data submitted to the U.S. Patent and Trademark Office. In addition to GenBank®, NCBI supports and distributes a variety of databases for the medical and scientific communities. These include the Online Mendelian Inheritance in Man (OMIM), the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute. Entrez is NCBI's search and retrieval system that provides users with integrated access to sequence, mapping, taxonomy, and structural data. Entrez also provides graphical views of sequences and chromosome maps. A feature of Entrez is the ability to retrieve related sequences, structures, and references. BLAST, as described herein, is a program for sequence similarity searching developed at NCBI for identifying genes and genetic features that can execute sequence searches against the entire DNA database. Additional software tools provided by NCBI include: Open Reading Frame Finder (ORF Finder), Electronic PCR, and the sequence submission tools, Sequin and Banklt. NCBI's various databases and software tools are available from the WWW or by FTP or by e-mail servers. Further information is available at ncbi.nlm.nih.gov.

Some biological data available over the internet is data that is generally viewed with a special browser "plug-in" or other executable code. One example of such a system is CHIME, a browser plug-in that allows an interactive virtual 3-dimensional display of molecular structures, including biological molecular structures. Further information regarding CHIME is available at mdlchime.com/chime/.

Online Oligos, Gene, or Protein Ordering

A variety of companies and institutions provide online systems for ordering biological compounds. Examples of such systems can be found at genosys.com/oligo_custinfo.cfm or genomictechnologies.com/Qbrowser2_FP.html. Typically, these systems accept some descriptor of a desired biological compound (such as an oligonucleotide, DNA strand, RNA strand, amino acid sequence, etc.) and then the requested compound is manufactured and is shipped to the customer in a liquid solution or other appropriate form.

To further illustrate, the methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an Intranet or an Internet.

In one internet embodiment, a client system typically executes a Web browser and is coupled to a server computer executing a Web server. The Web browser is typically a program such as IBM's Web Explorer, Microsoft's Internet explorer, NetScape, Opera, or Mosaic. The Web server is typically, but not necessarily, a program such as IBM's HTTP Daemon or other www daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

As mentioned, a user of a client connected to the Intranet or Internet may cause the client to request resources that are part of the web site(s) hosting the application(s) providing an implementation of the methods of this invention. Server program(s) then process the request to return the specified resources (assuming they are currently available). The standard naming convention (i.e., Uniform Resource Locator ("URL")) encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

The software implementing the method(s) of this invention can run locally on the server hosting the website in a true client-server architecture. Thus, the client computer posts requests to the host server which runs the requested process(es) locally and then downloads the results back to the client. Alternatively, the methods of this invention can be implemented in a "multi-tier" format in which a component of the method(s) are performed locally by the client. This can be implemented by software downloaded from the server on request by the client (e.g. a Java application) or it can be implemented by software "permanently" installed on the client.

In one embodiment the application(s) implementing the methods of this invention are divided into frames. In this paradigm, it is helpful to view an application not so much as a collection of features or functionality but, instead, as a collection of discrete frames or views. A typical application, for instance, generally includes a set of menu items, each of with invokes a particular frame—that is, a form which manifest certain functionality of the application. With this perspective, an application is viewed not as a monolithic body of code but as a collection of applets, or bundles of functionality. In this manner from within a browser, a user would select a Web page link which would, in turn, invoke a particular frame of the application (i.e., a sub-application). Thus, for example, one or more frames may provide functionality for inputting and/or encoding biological molecule(s) into one or more data spaces, while another frame provides tools for refining a model of the data space.

In certain embodiments, the methods of this invention are implemented as one or more frames providing, e.g., the following functionalit(ies). Function(s) to encode two or more biological molecules into character strings to provide a collection of two or more different initial character strings wherein each of said biological molecules comprises a selected set of subunits; functions to select at least two substrings from the character strings; functions to concatenate the substrings to form one or more product strings about the same length as one or more of the initial character strings; functions to add (place) the product strings to a collection of strings, and functions to implement any feature set forth herein.

The functions to distribute two or more biological molecules into data space can provide one or more windows wherein the user can insert representation(s) of biological molecules. In addition, the encoding function also, optionally, provides access to private and/or public databases accessible through a local network and/or the intranet whereby one or more sequences contained in the databases can be input into the methods of this invention. Thus, for example, in one embodiment, where the end user inputs a nucleic acid sequenced into the encoding function, the user can, optionally, have the ability to request a search of GenBank® and input one or more of the sequences returned by such a search into the encoding and/or diversity generating function.

Methods of implementing Intranet and/or Intranet embodiments of computational and/or data access processes are well known to those of skill in the art and are documented in great detail (see, e.g., Cluer et al. (1992) "A General Framework for the Optimization of Object-Oriented Queries," Proc SIGMOD International Conference on Management of Data, San Diego, Calif., Jun. 2-5, 1992, SIGMOD Record, vol. 21, Issue 2, June, 1992; Stonebraker, M., Editor; ACM Press, pp. 383-392; ISO-ANSI, Working Draft, "Information Technology-Database Language SQL," Jim Melton, Editor, International Organization for Standardization and American National Standards Institute, July 1992; Microsoft Corporation, "ODBC 2.0 Programmer's Reference and SDK Guide. The Microsoft Open Database Standard for Microsoft Windows.™ and Windows NT™, Microsoft Open Database Connectivity.TM. Software Development Kit," 1992, 1993, 1994 Microsoft Press, pp. 3-30 and 41-56; ISO Working Draft, "Database Language SQL-Part 2:Foundation (SQL/Foundation)," CD9075-2:199.chi.SQL, Sep. 11, 1997, and the like). Additional relevant details regarding web-based applications are found in WO 00/42559, entitled "METHODS OF POPULATING DATA STRUCTURES FOR USE IN EVOLUTIONARY SIMULATIONS," by Selifonov and Stemmer.

IX. Examples—Identifying Functional Constraints in Proteins by Synthetic DNA Shuffling The following non-limiting example is offered only by way of illustration.

Protein evolution is manifested by amino acid changes in the coding sequence. These amino acid changes are constrained by continuous selective pressure for function, resulting in independent and correlated changes in a protein's descendents. This section presents a method for differentiating covariation between amino acids reflecting functional selection, from covariation that simply results from a common ancestral origin.

Functional screening and sequencing of sequences suggests that most of the covariation observed in naturally occurring sequences results from phylogenetic descent, rather than functional constraints. The functional covariations that are identified are mainly in local structural elements, but there is also some covariation occurring over longer distances in genes/proteins. In general, genes and proteins are very plastic and have evolved to minimize the interdependence of allowed amino acid changes to facilitate adaptation.

During divergent evolution, protein sequences change while the biochemical function of the protein is generally retained. Correlated change between functionally linked residues in a protein provide for the preservation of protein structure and function throughout the evolutionary process. The functional link between the covarying residues can be due, e.g., to structural contact or an indirect effect through interactions with substrates, products, cofactors or other proteins. Independent mutations among functionally linked residues are often disadvantageous, but two simultaneous mutations may allow the protein to retain function. Alternatively, two or more residues may covary simply due to a common ancestral origin. Current analytical tools are limited in the ability to separate the functional from the phylogenetic (ancestral) covariation in a family of orthologous proteins. Statistical tools are limited both by the amount of data to infer covariation and also limited by the evolutionary models to explain the data. See, Wollenberg, K. R. & Atchley, W. R. Separation of phylogenetic and functional associations in biological sequences by using the parametric bootstrap. *Proc. Nat'l Acad. Sci* 97, 3288-91. (2000); Gaucher, E. A., Miyamoto, M. M. & Benner, S. A. Function-structure analysis of proteins using covarion-based evolutionary approaches: Elongation factors. *Proc. Nat'l Acad. Sci* 98, 548-552 (2001); Larson, S. M., Di Nardo, A. A. & Davidson, A. R. Analysis of covariation in an SH3 domain sequence alignment: applications in tertiary contact prediction and the design of compensating hydrophobic core substitutions. *J Mol Biol* 303, 433-46. (2000); Pollock, D. D., Taylor, W. R. & Goldman, N. Coevolving protein residues: maximum likelihood identification and relationship to structure. *J Mol Biol* 287, 187-98. (1999; and Atchley, W. R., Wollenberg, K. R., Fitch, W. M., Terhalle, W. & Dress, A. W. Correlations among amino acid sites in bHLH protein domains: an information theoretic analysis. *Mol Biol Evol* 17, 164-78. (2000).

If sequential point mutations are the primary mechanism for divergent evolution, most amino acid changes should occur independently: two simultaneous mutations will be extremely rare (e.g., at the rate of one mutation per 109 base pairs for a single cell division in *E. coli*).

Here an experiment is described in which all amino acids in a family of proteins are deliberately uncoupledby synthetic DNA shuffling (i.e., recombination of synthetic oligonucleotides that collectively correspond in sequence to a set of parental polynucleotides). By allowing all residues to vary independent of context and then screening for function, any covariation derived from common ancestral origin is eliminated and only covariation that contributes to function is retained. Functional variants are analyzed using mutual information theory to assess covariation between residues. Most of the covariation observed among the parental sequences is not preserved in functional chimeric proteins, indicating that it is primarily a measure of common ancestral descent. The methods also identify covarying residues that are not seen among the parents due to sampling effects.

Synthetic shuffling can be performed in a homology independent method that allows an essentially equal probability of each allowed residue at any given position to be incorporated into the final product. See, e.g., WO 00/42561 by Crameri et al., "Oligonucleotide Mediated Nucleic Acid Recombination" and Ness, J., Minshull, J. & Kim, S. Synthetic Shuffling. *Nature Biotech* Submitted (2001)). This is in contrast to many other recombination formats where the distribution of any single residue is dependent on its abundance and context among the parental genes. Synthetic shuffling results in a library of sequences that are completely chimeric on the single residue level and rich in natural diversity.

Despite the vast total size of libraries which can be generated by synthetic shuffling, characterization of only a small subset of the library is sufficient to test a significant number of covarying residue pairs for correlation with function. Any pair of covarying amino acid residues is sampled many times over among the fully characterized variants. Libraries generated through synthetic shuffling are an excellent unbiased source of data to analyze the relative importance of covariance and its distribution in a biological system.

Characterizing the distribution of a pre-screened library allows one to normalize the covariation found among the active variants to the inherent distribution of covariance the library. Any spurious artifactual mutual information derived from an imperfect library (for example oligonucleotide degeneracy biases produced during synthesis) can be eliminated. In general, there is no, or very little, difference in the sequence diversity distribution between pre-screened and active variants. In both cases, the variants are evenly distributed, suggesting no significant bias towards diversity originating from any given parent or cluster of parents. This shows that new regions of sequence space can be explored for functional activity by distributing the characterized variants evenly across the same sequence space covered by parental genes. Sequence distance traversed using classic directed evolution techniques such as random mutagenesis is usually limited to 1-3 amino acid residues per gene per round. Most of the solutions found through synthetic shuffling are consequently inaccessible by random mutagenesis.

Covariation between residues inferred from biological sequence data can be attributed to either functional constraints or phylogenetic relationships. Since one generally does not know the historical origin of the sequences at issue (at least where the sequences are naturally occurring), one cannot de-convolute the covariant nature of residues involved. This issue has typically been addressed either through collecting as many sequences as possible under a given node in a phylogenetic tree, or by computer simulations of possible evolutionary paths using a model for sequence evolution. Both approaches have significant complications and drawbacks. An inherent complication of the first type of covariation analysis is the inclusion of sequences having diverged not only in neutral mutations, but also in function. The divergence can be small, as in evolving to a slightly different pH optimum, or large as in evolving to catalyze a related but different reaction. No single orthologous enzyme pair has truly evolved for the exact same physiological conditions. Including sequences in the covariation analysis that have diverged in function adds noise to the correlations, as they are subjected to different selective pressures. Another, perhaps more serious concern, is the inability to ever gather all sequences under a phylogenetic node to ensure that the distribution in the data set is unbiased due to sampling effects. In a library produced by synthetic shuffling, all inherent covariation is removed and amino acid diversity occurring in any one position has an equal probability of occurring in any variant. Screening such a library (e.g., in vitro) for a defined biochemical function, identifies all covariation derived from functional constraints required for the assayed biological activity of the enzyme. The remainder of the covariation found among the parental genes, but not present among the functional progeny, is consequently the result of common ancestral origin.

The covariation among a set of variants from the library can be assessed and visualized by aligning the sequences and removing residues that are conserved throughout the alignment. The mutual information between each varying residue pairs is plotted in a two-dimensional matrix. Each row/column represents one of the varying residue positions for a protein and each cell in the matrix represents a possible residue pair. A filled cell of the matrix corresponds to highly covarying residues. Each parental sequence has evolved independently through natural selection and their phylogenetic distribution is highly clustered. Displaying every residue pair for the parental genes identifies many residue pairs that covary. The mutual information distribution is normalized to have a mean of 0 and variance of 1. Covariation here is defined as residue pairs with mutual information higher than 2 deviations for that alignment.

After making the synthetic library, but before exposing the variants to any selective pressure, variants are isolated. These unscreened variants are characterized for covariation in the same way as the parental genes. In most cases, the distribution of the varying residues is uniform, with all varying residues exist in conjunction with all other varying residues. To the extent that there is covariation, that covariation is not the result of functional constraints (i.e., the variants have not been exposed to selection). This in effect, is a control of the question of whether the covariation is a result of functional constraints. After synthetic shuffling and selection for function, covarying residue pairs that are identified are the result of functional constraints. The covariation found among the parental genes and not among the functionally active library variants could also reflect a selective pressure for indirect effects on the organism. Indirect effects could potentially be any trait, such as sequestering of cofactors or cellular localization, etc. that is not specifically related to the screening criteria of the selection assay.

1. Mutual Information Analysis

In a protein alignment, the entropy measure for each position in the alignment indicates the degree of variability and preference for each amino acid. The following equation is used to quantify site-entropy (Shannon, C. E. The mathematical theory of communication. 1963. *MD Comput* 14, 306-17. (1997)).

$$I_i = \Sigma k P(A^k_i) \log P(A^k_i) \tag{1}$$

Where the sum is over all k amino acids $\{A^k_i\}$ occurring at position i in the alignment. $P(A^k_i)$ is the probability of amino acid k at position i. Likewise, covariance between amino acids can be measured by using the mutual information content between pairs of sites.

$$MI_{ij} = \sum_k \sum_l P(A^k_i \text{ and } A^l_j) \log \frac{P(A^k_i \text{ and } A^l_j)}{P(A^k_i) P(A^l_j)} \tag{2}$$

The double summation is over all possible pairs of amino acids $\{A^k_i\}$ and $\{A^l_j\}$ at positions i and j respectively. $P(A^k_i)$ is the probability of amino acid k at position i and $P(A^k_i$ and $A^l_j)$ is combined probability of amino acid k at position i and amino acid l at position j.

The MI values are normalized for each group of variants to have the same mean of 0.0 and standard deviation of 1.0. The degree of co-variation among any residue pair is identified by the deviation of the MI for the given pair from the expected mutual information content.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for identifying nucleotides for variation in nucleic acids encoding a protein variant library in order to impact a desired activity, said method comprising:
   (a) receiving data characterizing a training set of a protein variant library, wherein the data comprises activity and a nucleotide sequence for each protein variant in the training set;
   (b) from the data, developing a sequence activity model for predicting activity as a function of independent variables each specifying the presence or absence of a nucleotide, identity of said nucleotide, and position of said nucleotide in a nucleotide sequence;
   (c) using the sequence activity model to rank positions in a reference nucleotide sequence and nucleotide types at the ranked positions in the reference nucleotide sequence in order of impact on the desired activity;
   (d) using the ranking to identify one or more nucleotides, in the reference nucleotide sequence, that are to be varied or fixed in order to impact the desired activity, wherein the nucleotides to be varied include codons encoding particular amino acids;
   (e) generating a new protein variant library containing one or more new protein variants having amino acid sequences encoded by nucleic acids in which the identified nucleotides are varied or fixed in order to impact the desired activity;
   (f) assaying the new protein variant library to provide an updated training set comprising sequence and activity information for members of the new protein variant library to develop a new sequence activity model; and
   (g) using the new sequence activity model to identify one or more nucleotides in a new reference nucleotide sequence that are to be varied or fixed in order to impact the desired activity.

2. The method of claim 1, wherein the activity is a function of expression of nucleic acids.

3. A computer program product comprising a tangible machine readable medium on which is provided program instructions for identifying nucleotides for variation in nucleic acids encoding a protein variant library in order to impact a desired activity, said instructions comprising:
   (a) code for receiving data characterizing a training set of a protein variant library, wherein the data comprises activity and a nucleotide sequence for each protein variant in the training set;
   (b) code for using the data to develop a sequence activity model for predicting activity as a function of independent variables each specifying the presence or absence of a nucleotide, identity of said nucleotide, and position of said nucleotide in a nucleotide sequence corresponding;
   (c) code for using the sequence activity model to rank positions in a reference nucleotide sequence and nucleotide types at the ranked positions in the reference nucleotide sequence in order of impact on the desired activity;
   (d) code for generating a ranked list of the nucleotide positions and the nucleotide types at the ranked positions in the reference nucleotide sequence;
   (e) code for using the ranking to identify one or more nucleotides, in the reference nucleotide sequence, that are to be varied or fixed in order to impact the desired activity, wherein the nucleotides to be varied include codons encoding particular amino acids;
   (f) code for receiving activity data characterizing a new protein variant library containing one or more protein variants having sequences in which the identified nucleotides were varied or fixed in order to impact the desired activity;
   (g) code for using the activity data characterizing the new protein variant library to provide an updated training set comprising sequence and activity information for members of the new protein variant library to develop a new sequence activity model;
   (h) code for using the new sequence activity model to identify one or more nucleotides in a new reference nucleotide sequence that are to be varied or fixed in order to impact the desired activity; and
   (i) code for outputting information, in a user readable format, identifying members of the new protein variant library.

4. The computer program product of claim 3, wherein the activity is a function of expression of nucleic acids.

5. The method of claim 1, wherein (e) comprises expressing the new protein variant library from polynucleotides encoding members of the new protein variant library and wherein the polynucleotides are prepared by gene synthesis.

6. The method of claim 1, wherein (e) comprises expressing the new protein variant library from polynucleotides encoding members of the new protein variant library and wherein the polynucleotides are prepared by mutagenesis.

7. The method of claim 1, wherein (e) comprises expressing the new protein variant library from polynucleotides encoding members of the new protein variant library and wherein the polynucleotides are prepared by performing a recombination-based diversity generation mechanism.

8. The method of claim 1, wherein (f) comprises screening the new protein variant library to identify protein variants having the desired activity.

9. The method of claim 8, further comprising sequencing the identified protein variants having the desired activity.

10. The method of claim 9, further comprising repeating (a)-(c) using the activity and sequence data from protein variants in the new protein variant library.

11. The method of claim 1, wherein the members of the new protein variant library comprise the same amino acid sequence encoded by different nucleotide sequences.

12. The method of claim 1, wherein developing the new sequence activity model comprises performing a regression analysis.

13. The method of claim 12, wherein the regression analysis is based on a partial least square regression.

14. The method of claim 12, wherein the regression analysis is based on a principal component regression.

15. The computer program product of claim 3, wherein the code for developing the new sequence activity model comprises code for performing a regression analysis.

16. The computer program product of claim 15, wherein the code for performing the regression analysis comprises code for performing a partial least squares regression.

17. The computer program product of claim 15, wherein the code for performing the regression analysis comprises code for performing a principal component regression.

18. The method of claim 1, wherein the presence or absence of a nucleotide, as specified by an independent variable, is represented by a bit value.

19. The method of claim 1, wherein the independent variables have associated coefficients specifying a magnitude of contribution of independent nucleotides at their corresponding positions to said activity.

20. The computer program products of claim 3, wherein the presence or absence of a nucleotide, as specified by an independent variable, is represented by a bit value.

21. The computer program products of claim 3, wherein the independent variables have associated coefficients specifying a magnitude of contribution of independent nucleotides at their corresponding positions to said activity.

* * * * *